(12) United States Patent
Mason et al.

(10) Patent No.: US 10,697,010 B2
(45) Date of Patent: Jun. 30, 2020

(54) HIGH-THROUGHPUT SINGLE-CELL ANALYSIS COMBINING PROTEOMIC AND GENOMIC INFORMATION

(71) Applicant: Becton, Dickinson and Company, Franklin Lakes, NJ (US)

(72) Inventors: Clark Mason, Franklin Lakes, NJ (US); Liping Yu, San Jose, CA (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 51 days.

(21) Appl. No.: 15/046,225

(22) Filed: Feb. 17, 2016

(65) Prior Publication Data

US 2016/0244828 A1    Aug. 25, 2016

Related U.S. Application Data

(60) Provisional application No. 62/118,412, filed on Feb. 19, 2015.

(51) Int. Cl.
| | |
|---|---|
| C12Q 1/6874 | (2018.01) |
| C12Q 1/6806 | (2018.01) |
| G01N 15/14 | (2006.01) |
| C12Q 1/6804 | (2018.01) |
| C12Q 1/6886 | (2018.01) |
| G01N 15/10 | (2006.01) |

(52) U.S. Cl.
CPC ......... *C12Q 1/6874* (2013.01); *C12Q 1/6804* (2013.01); *C12Q 1/6806* (2013.01); *C12Q 1/6886* (2013.01); *G01N 15/1404* (2013.01); *G01N 15/1459* (2013.01); *C12Q 2600/118* (2013.01); *C12Q 2600/158* (2013.01); *G01N 2015/1006* (2013.01); *G01N 2015/1402* (2013.01); *G01N 2015/149* (2013.01)

(58) Field of Classification Search
CPC .................................................. C12Q 1/6874
USPC .................................................. 506/9
See application file for complete search history.

(56) References Cited

U.S. PATENT DOCUMENTS

| | | |
|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchik et al. |
| 5,962,272 A | 10/1999 | Chenchik et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'Neill et al. |
| 6,138,077 A | 10/2000 | Brenner |
| 6,140,489 A | 10/2000 | Brenner |

(Continued)

FOREIGN PATENT DOCUMENTS

| | | |
|---|---|---|
| DE | 102008025656 | 12/2009 |
| EP | 0 799 897 | 10/1997 |

(Continued)

OTHER PUBLICATIONS

Ozkumur et al. (Sci Transl Med, Apr. 3, 2013, 5(179), pp. 1-20) (Year: 2013).*
Song et al. (Journal of Chromatography A, 1302, 2013, pp. 191-196). (Year: 2013).*
Bogdanova et al., Jan. 2008, Normalization of full-length enriched cDNA, Molecular Biosystems, 4(3):205.
Patanjali et al., Mar. 1991, Construction of a uniform-abundance (normalized) CNDA library, Proceedings of the National Academy of Sciences, 88(5):1943-1947.

(Continued)

*Primary Examiner* — Karla A Dines
(74) *Attorney, Agent, or Firm* — Kathleen Y. Rao; Bret E. Field; Bozicevic, Field & Francis LLP

(57) ABSTRACT

Disclosed herein are methods for single-cell sequencing. In some examples, the methods include enriching a sample comprising a plurality of cells for cells of interest to produce an enriched cell sample; isolating one or more cells of interest in the enriched cell sample; and obtaining sequence information of one or more polynucleotides from each of the one or more isolated cells. Obtaining sequence information may include generating a molecularly indexed polynucleotide library from the one or more isolated cells. Enriching the sample may include focusing cells of interest in the sample using acoustic focusing.

31 Claims, 41 Drawing Sheets

(56) References Cited

U.S. PATENT DOCUMENTS

| | | |
|---|---|---|
| 6,172,214 B1 | 1/2001 | Brenner |
| 6,197,506 B1 | 3/2001 | Fodor et al. |
| 6,197,554 B1 | 3/2001 | Lin et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,284,485 B1 | 9/2001 | Boyle |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Travis |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'Neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1 | 12/2006 | Sloge |
| 7,393,665 B2 | 7/2008 | Brenner |
| 7,424,368 B2 | 9/2008 | Huang et al. |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,228,229 B2 | 1/2016 | Olson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,905,005 B2 | 2/2018 | Fu et al. |
| 9,951,386 B2 | 4/2018 | Hindson et al. |
| 2002/0065609 A1 | 5/2002 | Ashby |
| 2002/0072058 A1 | 6/2002 | Voelker et al. |
| 2002/0168665 A1 | 11/2002 | Okawa |
| 2002/0187480 A1 | 12/2002 | Brandon |
| 2003/0003490 A1 | 1/2003 | Fan et al. |
| 2003/0049616 A1 | 3/2003 | Brenner et al. |
| 2003/0082818 A1 | 5/2003 | Bahnson et al. |
| 2003/0104436 A1 | 6/2003 | Morris et al. |
| 2003/0175908 A1 | 9/2003 | Linnarson |
| 2003/0186251 A1 | 10/2003 | Dunn et al. |
| 2003/0207300 A1 | 11/2003 | Matray et al. |
| 2004/0047769 A1 | 3/2004 | Tanaami |
| 2004/0096368 A1 | 5/2004 | Davis |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0053952 A1 | 3/2005 | Hong et al. |
| 2005/0105077 A1* | 5/2005 | Padmanabhan .... G01N 15/1484 356/39 |
| 2005/0170373 A1 | 8/2005 | Monforte |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0073506 A1 | 4/2006 | Christians et al. |
| 2006/0211030 A1 | 9/2006 | Brenner |
| 2006/0263709 A1 | 11/2006 | Matsumura et al. |
| 2006/0263789 A1 | 11/2006 | Kincaid |
| 2006/0280352 A1 | 12/2006 | Muschler |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0105090 A1 | 5/2007 | Cassidy et al. |
| 2007/0117121 A1 | 5/2007 | Hutchison |
| 2007/0117134 A1 | 5/2007 | Kou |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0061513 A1 | 3/2009 | Andersson et al. |
| 2009/0105959 A1 | 4/2009 | Braverman et al. |
| 2009/0137407 A1 | 5/2009 | Church et al. |
| 2009/0220385 A1 | 9/2009 | Brown |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal |
| 2009/0298709 A1 | 12/2009 | Ma |
| 2010/0069250 A1 | 3/2010 | White, III |
| 2010/0105049 A1 | 4/2010 | Ehrich et al. |
| 2010/0105886 A1 | 4/2010 | Woudenberg et al. |
| 2010/0120630 A1 | 5/2010 | Huang et al. |
| 2010/0159533 A1 | 6/2010 | Lipson et al. |
| 2010/0255471 A1 | 10/2010 | Clarke |
| 2010/0267028 A1* | 10/2010 | Pasche ................ C12Q 1/6886 435/6.12 |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |

(56) References Cited

U.S. PATENT DOCUMENTS

| | | |
|---|---|---|
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0014977 A1 | 1/2012 | Furihata et al. |
| 2012/0034607 A1 | 2/2012 | Rothberg |
| 2012/0040843 A1 | 2/2012 | Ducree et al. |
| 2012/0045844 A1 | 2/2012 | Rothberg et al. |
| 2012/0065081 A1 | 3/2012 | Chee |
| 2012/0071331 A1 | 3/2012 | Casbon |
| 2012/0149603 A1 | 6/2012 | Cooney |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0220022 A1 | 8/2012 | Ehrlich et al. |
| 2012/0220494 A1 | 8/2012 | Samuels |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0190206 A1 | 7/2013 | Leonard |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0057799 A1 | 2/2014 | Johnson et al. |
| 2014/0147860 A1* | 5/2014 | Kaduchak ........ G01N 33/56966 435/7.21 |
| 2014/0155274 A1* | 6/2014 | Xie ..................... C12Q 1/6853 506/2 |
| 2014/0155295 A1 | 6/2014 | Hindson et al. |
| 2014/0178438 A1 | 6/2014 | Sahin et al. |
| 2014/0206079 A1 | 7/2014 | Malinoski |
| 2014/0206547 A1 | 7/2014 | Wang |
| 2014/0216128 A1 | 8/2014 | Neat |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1 | 1/2015 | Hindson et al. |
| 2015/0066385 A1 | 3/2015 | Schnall-Levin et al. |
| 2015/0099673 A1 | 4/2015 | Fodor et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0225778 A1 | 8/2015 | Hindson et al. |
| 2015/0247182 A1 | 9/2015 | Faham et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0376609 A1 | 12/2015 | Hindson et al. |
| 2016/0010151 A1 | 1/2016 | Fan et al. |
| 2016/0026758 A1 | 1/2016 | Jabara et al. |
| 2016/0055632 A1 | 2/2016 | Fu et al. |
| 2016/0122753 A1* | 5/2016 | Mikkelsen ......... C12N 15/1065 506/4 |
| 2016/0145683 A1 | 5/2016 | Fan et al. |
| 2016/0208322 A1 | 7/2016 | Anderson et al. |
| 2016/0222378 A1 | 8/2016 | Fodor et al. |
| 2016/0253584 A1 | 9/2016 | Fodor et al. |
| 2016/0257993 A1 | 9/2016 | Fu et al. |
| 2016/0258012 A2* | 9/2016 | Fan ..................... C12Q 1/6874 |
| 2016/0265069 A1 | 9/2016 | Fan et al. |
| 2016/0289669 A1 | 10/2016 | Fan et al. |
| 2016/0289740 A1 | 10/2016 | Fu et al. |
| 2016/0312276 A1 | 10/2016 | Fu et al. |
| 2016/0320720 A1 | 11/2016 | Fan et al. |
| 2016/0326584 A1 | 11/2016 | Fodor et al. |
| 2016/0376583 A1 | 12/2016 | Fodor et al. |
| 2016/0376648 A1 | 12/2016 | Fodor et al. |
| 2017/0073730 A1 | 3/2017 | Betts et al. |
| 2017/0154421 A1 | 6/2017 | Fu et al. |
| 2017/0314067 A1 | 11/2017 | Shum et al. |
| 2017/0337459 A1 | 11/2017 | Fodor et al. |
| 2017/0342405 A1 | 11/2017 | Fu et al. |
| 2017/0342465 A1 | 11/2017 | Shum et al. |
| 2017/0344866 A1 | 11/2017 | Fan et al. |
| 2018/0002764 A1 | 1/2018 | Fan et al. |
| 2018/0037942 A1 | 2/2018 | Fu et al. |
| 2018/0258500 A1 | 9/2018 | Fan et al. |
| 2018/0291470 A1 | 10/2018 | Fan et al. |

FOREIGN PATENT DOCUMENTS

| | | |
|---|---|---|
| EP | 1 473 080 | 11/2004 |
| EP | 1 647 600 | 4/2006 |
| EP | 1 845 160 | 10/2007 |
| EP | 2 623 613 | 8/2013 |
| EP | 2 805 769 | 11/2014 |
| JP | 2005-233974 | 9/2005 |
| JP | 2008-256428 | 10/2008 |
| JP | 2013-039275 | 2/2013 |
| WO | WO 89/01050 | 2/1989 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO 02/056014 | 7/2002 |
| WO | WO 02/059355 | 8/2002 |
| WO | WO 02/070684 | 9/2002 |
| WO | WO 04/017374 | 2/2004 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO 06/071776 | 7/2006 |
| WO | WO 06/102264 | 9/2006 |
| WO | WO 07/087310 | 8/2007 |
| WO | WO 07/087312 | 8/2007 |
| WO | WO 07/147079 | 12/2007 |
| WO | WO 08/096318 | 8/2008 |
| WO | WO 08/122051 | 10/2008 |
| WO | WO 08/147428 | 12/2008 |
| WO | WO 08/150432 | 12/2008 |
| WO | WO 09/148560 | 12/2009 |
| WO | WO 09/152928 | 12/2009 |
| WO | WO 10/117620 | 10/2010 |
| WO | WO 11/123246 | 10/2011 |
| WO | WO 11/143659 | 11/2011 |
| WO | WO 11/155833 | 12/2011 |

(56) References Cited

FOREIGN PATENT DOCUMENTS

| | | |
|---|---|---|
| WO | WO 12/038839 | 3/2012 |
| WO | WO 12/042374 | 4/2012 |
| WO | WO 12/047297 | 4/2012 |
| WO | WO 12/048341 | 4/2012 |
| WO | WO 12/083225 | 6/2012 |
| WO | WO 12/108864 | 8/2012 |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/162267 | 11/2012 |
| WO | WO 13/019075 | 2/2013 |
| WO | WO 13/117595 | 8/2013 |
| WO | WO 13/130674 | 9/2013 |
| WO | WO 13/148525 | 10/2013 |
| WO | WO 13/173394 | 11/2013 |
| WO | WO 13/176767 | 11/2013 |
| WO | WO 13/177206 | 11/2013 |
| WO | WO 13/188831 | 12/2013 |
| WO | WO 13/188872 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO 14/028537 | 2/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO 14/144495 | 9/2014 |
| WO | WO 14/201273 | 12/2014 |
| WO | WO 14/210353 | 12/2014 |
| WO | WO 15/002908 | 1/2015 |
| WO | WO 15/031691 | 3/2015 |
| WO | WO 15/035087 | 3/2015 |
| WO | WO 15/044428 | 4/2015 |
| WO | WO 15/047186 | 4/2015 |
| WO | WO 14/071361 | 5/2015 |
| WO | WO 15/103339 | 7/2015 |
| WO | WO 15/134787 | 9/2015 |
| WO | WO 15/200869 | 12/2015 |
| WO | WO 16/138500 | 9/2016 |

OTHER PUBLICATIONS

Office Action dated Feb. 13, 2017 in U.S. Appl. No. 14/381,488.
Third Office Action dated Dec. 27, 2016 in Chinese Patent Application No. 201380022187.9.
Official Action dated Dec. 28, 2016 in Japanese Patent Application No. 2014-558975.
Combined Search and Examination Report dated Feb. 21, 2017 in GB Patent Application No. 1609740.4.
Office Action dated Jan. 19, 2017 in U.S. Appl. No. 15/055,445.
International Search Report and Written Opinion dated Dec. 5, 2016 in PCT/US16/024783.
International Search Report and Written Opinion dated Jan. 31, 2017 in PCT/US16/050694.
Cai, Mar. 2013, Turning single cells in microarrays by super-resolution bar-coding, Brief Funct Genomics, 12(2):75-80.
Castellarnau et al., Jan. 2015, Stochastic particle barcoding for single-cell tracking and multiparametric analysis, Small, 11(4):489-498.
Dalerba et al., 2011, Single-cell dissection of transcriptional heterogeneity in human colon tumors, Nat Biotechnol., 29(12):1120-1127 and Supplementary Material.
Fan, Nov. 2010, Molecular counting: from noninvasive prenatal diagnostics to whole-genome haplotyping, doctoral dissertation, Stanford University, 185 pp.
Haff, 1994, Improved quantitative PCR using nested primers, PCR Methods and Applications, 3:332-337.

Kebschull et al., Jul. 17, 2015, Sources of PCR-induced distortions in high-throughput sequencing data sets, Nucleic Acids Research, 15 pp.
Kim et al., Jun. 8, 2007, Polony multiplex analysis of gene expression (PMAGE) in mouse hypertrophic cardiomyopathy, Science, 316(5830):1481-1484.
Kotake et al., 1996, A simple nested RT-PCR method for quantitation of the relative amounts of multiple cytokine mRNAs in small tissue samples, Journal of Immunological Methods, 199:193-203.
Kurimoto et al., Mar. 17 2006, An improved single-cell cDNA amplification method for efficient high-density oligonucleotide microarray analysis, Nucleic Acids Res., 34(5):e42.
Picelli et al., Jul. 30, 2014, Tn5 transposase and tagmentation procedures for massively scaled sequencing projects, Genome Research 24(12):2033-2040.
Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.
Speicher et al., Oct. 2005, The new cytogenetics: blurring the boundaries with molecular biology, Nature Reviews Genetics, 6(10):782-792.
Takahashi et al., Mar. 2006, Novel technique of quantitative nested real-time PCR assay for *Mycobacterium tuberculosis* DNA, Journal of Clinical Microbiology, 44(3):1029-1039.
Wang et al., May 21, 2015, Advances and applications of single-cell sequencing technologies, Molecular Cell, 58(4):598-609.
Ward et al., Jan. 1, 2009, Fundamentals of acoustic cytometry, Current Protocols in Cytometry, Supplement 49:1.22.1-1.22.12.
Zheng et al., Feb. 2016, Haplotyping germline and cancer genomes with high-throughput linked-read sequencing, Nature Biotechnology, 34(3):303-311.
International Search Report and Written Opinion dated May 3, 2016 in PCT/US16/018354.
Office action dated Jul. 20, 2016 for U.S. Appl. No. 14/281,706.
Office Action dated May 10, 2016 in U.S. Appl. No. 14/381,488.
Second Office Action dated Jun. 6, 2016 in Chinese patent application No. 201380022187.9.
Examination report dated Jul. 12, 2016 in European patent application No. 13755319.4.
Search and Examination Report dated Jan. 27, 2016 in GB patent application No. 1408829.8.
Examination Report dated Jun. 8, 2016 in GB patent application No. 1408829.8.
Examination Report dated Jun. 15, 2016 in Great Britain patent application No. GB1511591.8.
Office Action dated May 13, 2016 in U.S. Appl. No. 14/508,911.
International Search Report and Written Opinion dated Jun. 20, 2016 in PCT/US16/14612.
International Search Report and Written Opinion dated Jun. 17, 2016 in PCT/US16/019962.
Written Opinion dated Jul. 5, 2016 in PCT/US16/019962.
Invitation to Pay Additional Search Fees dated Jun. 2, 2016 in PCT/US16/019971.
International Search Report and Written Opinion dated Jun. 9, 2016 in PCT/US16/022712.
Achim et al., May 2015, High-throughput spatial mapping of single-cell RNA-seq data to tissue of origin. Nature Biotechnology, 33(5):503-511.
Alkan et al., Oct. 2009, Personalized copy Number and segmental duplication maps using next-generation sequencing. Nat Genet., 41(10):1061-1067.
Ansorge, 2009, Next-generation DNA sequencing techniques. New Biotechnology, 25(4):195-203.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Bendall et al., May 6, 2011, Single-cell mass cytometry of differential immune and drug responses across a human hematopoietic continuum. Science, 332(6030):687-696.

(56) References Cited

OTHER PUBLICATIONS

Bionumbers, Aug. 21, 2010, Useful fundamental Numbers in molecular biology, http://bionumbers.hms.harvard.edu/KeyNumbers/aspx, 4 pp.
Blainey, May 2013, The future is now: single-cell genomics of bacteria and archaea, FEMS Microbiol Rev., 37(3):407-427.
Bonaldo et al., Sep. 1996, Normalization and subtraction: two approaches to facilitate gene discovery. Genome Res., 6(9):791-806.
Braha et al., 2000, Simultaneous stochastic sensing of divalent metal ions. Nature Biotechnology, 18:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brodin et al., 2015, Challenges with using primer IDs to improve accuracy of next generation sequencing, 19(3):1-12.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castle et al., Apr. 16, 2010, DNA copy number, including telomeres and mitochondria, assayed using next-generation sequencing. BMC Genomics, 11:244. doi: 10.1186/1471-2164-11-244.
Chamberlain et al., Dec. 9, 1988, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Sciencexpress, pp. 1-21.
Church et al., 1988, Multiplex DNA sequencing. Science, 240:185-188.
Costello et al., Apr. 1, 2013, Discovery and characterization of artifactual mutations in deep coverage targeted capture sequencing data due to oxidative DNA damage during sample preparation. Nucleic Acids Res, 41(6):e67.
Cox. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Sciencexpress, pp. 1-9.
Daines et al., Aug. 2009, High-throughput multiplex sequencing to discover copy number variants in *Drosophila*. Genetics, 182(4):935-941.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.
De Saizieu et al., 1998, Bacterial transcript imaging by hybridization of total RNA to oligonucleotide arrays. Nature Biotechnology, 16:45-48.
Dirks et al., Oct. 26, 2004, Triggered amplification by hybridization chain reaction.,Proc Natl Acad Sci U S A, 101(43),15275-15278.
Fan et al., Feb. 6, 2015, Expression profiling. Combinatorial labeling of single cells for gene expression cytometry. Science, 347(6222):1258367.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Jul. 19, 2012, Non-invasive prenatal measurement of the fetal genome. Nature, 487(7407):320-324.
Feldhaus et al., Jan. 15, 2000, Oligonucleotide-conjugated beads for transdominant genetic experiments, Nucleic Acids Res., 28(2):534-543.
Fox-Walsh et al., Oct. 2011, A multiplex RNA-seq strategy to profile poly(A+) RNA: application to analysis of transcription response and 3' end formation.,Genomics, 98(4),266-721.
Fu et al., Mar. 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.
Gundry et al., Mar. 2012, Direct, genome-wide assessment of DNA mutations in single cells. Nucleic Acids Res., 40(5):2032-40.
Hacia et al., 1999, Determination of ancestral alleles for human single-nucleotide polymorphisms using high-density oligonucleotide arrays. Nature Genetics, 22:164-167.
Hamady et al., Mar. 2008, Error-correcting barcoded primers for pyrosequencing hundreds of samples in multiplex. Nat Methods, 5(3):235-237.
Harrington et al.,2009, Cross-sectional characterization of HIV-1 env compartmentalization in cerebrospinal fluid over the full disease course, AIDS, 23(8) 907-915.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.
Hug et al., 2003, Measure of the Number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.

(56) References Cited

OTHER PUBLICATIONS

Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.

Kanagawa, 2003, Bias and artifacts in multitemplate polymerase chain reactions (PCR), Journal of Bioscience and Bioengineering, 96(4):317-323.

Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.

Kinde et al., Jun. 7, 2011, Detection and quantification of rare mutations with massively parallel sequencing, Proc. Natl Acad Sci, 108(23):9530-0535.

Kivioja et al., Jan. 2012, Counting absolute numbers of molecules using unique molecular identifiers. Nature Methods, 9(1):72-76.

Koboldt et al., Sep. 1, 2009, VarScan: variant detection in massively parallel sequencing of individual and pooled samples. Bioinformatics. 25(17):2283-2285.

Konig et al., Jul. 2010, iCLIP reveals the function of hnRNAP particles in splicing at individual nucleotide resolution, Nature Structural & Molecular Biology, 17(7):909-916.

Larson et al., Nov. 2009, A single molecule view of of gene expression. Trends Cell Biol. 19(11):630-637.

Leamon et al., Nov. 2003, A massively parallel PicoTiterPlate based platform for discrete picoliter-scale polymerase chain reactions, Electrophoresis, 24(21):3769-3777.

Lee et al., Mar. 21, 2014, Highly multiplexed subcellular RNA sequencing in situ. Science. 343(6177):1360-1363.

Lizardi et al., Jul. 1998, Mutation detection and single-molecule counting using isothermal rolling-circle amplification. Nat Genet. 19(3):225-32.

Lockhart et al., 1996, Expression monitoring by hybridization to high-density oligonucleotide arrays. Nature Biotechnology, 14:1675-1680.

Lovatt et al., Feb. 2014, Transcriptome in vivo analysis (TIVA) of spatially defined single cells in live tissue. Nat Methods. 11(2):190-196.

Lucito et al., 1996, Representational Oligonucleotide Microarray Analysis: A High-Resolution Method to Detect Genome Copy Number Variation. Genome Research, 13: 2291-2305.

Maamar et al., 2007, Noise in Gene Expression Determines Cell Fate in Bacillus subtilis. Science, 317:526-529.

Macaulay et al., 2015, G&T-seq: parallel sequencing of single-cell genomes and transcriptomes. Nature Methods, pp. 1-7.

Macosko et al., 2015, Highly parallel genome-wide expression profiling of individual cells using nanoliter droplets, Cell 161:1202-1214 (and supplemental information).

Makrigiorgos et al., Sep. 2002, A PCR-Based amplification method retaining quantative difference between two complex genomes. Nature Biotech, 20(9):936-939.

Marqulies et al., Sep. 15, 2005 Genome sequencing in microfabricated high-density picolitre reactors, Nature, 437:376-380.

Mccloskey et al., Dec. 2007, Encoding PCR products with batch-stamps and barcodes. Biochem Genet. 45(11-12):761-767.

Medvedev et al., Nov. 2010, Detecting copy number variation with mated short reads. Genome Res. 20(11):1613-1622.

Mei et al., Mar. 22, 2010, Identification of recurrent regions of Copy-Number Variants across multiple individuals. BMC Bioinformatics. 11:147.

Merriam-Webster, definition of associate,: http://www.merriam-webster.com/dictionary/associate, accessed Apr. 5, 2016.

Miller et al., 2006, Directed evolution by in vitro compartmentalization, Nature Methods, 3:561-570.

Miner et al., 2004, Molecular barcodes detect redundancy and contamination in hairpin-bisulfite PCR, Nucleic Acids Research, 32(17):e135.

Mortazavi et al., 2008, Mapping and quantifying mammalian transcriptomes by RNA-Seq. Nat. Methods. 5:621-628.

Newell et al., Jan. 27, 2012, Cytometry by time-of-flight shows combinatorial cytokine expression and virus-specific cell niches within a continuum of CD8+ T cell phenotypes. Immunity. 36(1):142-152.

Novak et al., Jan. 20, 2011, Single-cell multiplex gene detection and sequencing with microfluidically generated agarose emulsions, Angew Chem Int Ed Engl., 50(2):390-395.

Ogino et al., Nov. 2002, Quantification of PCR bias caused by a single nucleotide polymorphism in SMN gene dosage analysis, Journal of Molecular Diagnostics, 4(4):185-190.

Ogino et al., Nov. 2002, Quantification of PCR bias caused by a single nucleotide polymorphism in SMN gene dosage analysis. J Mol Diagn. 4(4):185-190.

Parameswaran et al., 2007, A pyrosequencing-tailored nucleotide barcode design unveils opportunities for large-scale sample multiplexing. Nucleic Acids Res. 35(19):e130.

Park et al., May 2010, Discovery of common Asian copy number variants using integrated high-resolution array CGH and massively parallel DNA sequencing. Nat Genet. 42(5):400-405.

Pihlak et al., 2008, Rapid genome sequencing with short universal tiling probes. Nature Biotechnology, 26:676-684.

Pinkel et al., 2005, Comparative Genomic Hybridization. Annual Review of Genomics and Human Genetics, 6:331-354.

Pleasance et al., Jan. 14, 2010, A small-cell lung cancer genome with complex signatures of tobacco exposure. Nature. 463(7278):184-190.

Plessy et al., Feb. 2013, Population transcriptomics with single-cell resolution: a new field made possible by microfluidics: a technology for high throughput transcript counting and data-driven definition of cell types, Bioessays, 35(2):131-140.

Qiu et al., Oct. 2003, DNA sequence-based "bar codes" for tracking the origins of expressed sequence tags from a maize cDNA library constructed using multiple mRNA sources. Plant Physiol. 133(2):475-481.

Roche Diagnostics GmbH, 2006, Genome Sequencer 20 System: First to the Finish (product brochure), 40 pp.

Sasagawa et al., 2013, Quartz-Seq: a highly reproducible and sensitive single-cell RNA sequencing method, reveals non-genetic gene-expression heterogeneity. Genome Biology, 14: R31.

Sasuga et al., Dec. 2008, Single-cell chemical lysis method for analyses of intracellular molecules using an array of picoliter-scale microwells, Anal Chem, 80(23):9141-9149.

Satija et al., May 2015, Spatial reconstruction of single-cell gene expression data. Nature Biotechnology, 33(5):495-508.

Schmitt et al., Sep. 4, 2012, Detection of ultra-rare mutations by next-generation sequencing. Proc Natl Acad Sci U S A. 109(36):14508-14513.

Sebat et al., 2004, Large-Scale Copy Number Polymorphism in the Human Genome. Science, 305:525-528.

Shalek et al., Jun. 13, 2013, Single-cell transcriptomics reveals bimodality in expression and splicing in immune cells. Nature. 498(7453):236-240.

Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.

Shoemaker et al., 1996, Quantitative phenotypic analysis of yeast deletion mutants using a highly parallel molecular bar-coding strategy. Nature Genetics, 14:450-456.

Simpson et al., Feb. 15, 2010, Copy Number variant detection in inbred strains from short read sequence data. Bioinformatics. 26(4):565-567.

Smith et al., 2010, Highly-multiplexed barcode sequencing: an efficient method for parallel analysis of pooled samples. Nucleic Acids Research, 38(13):e142.

Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.

(56) References Cited

OTHER PUBLICATIONS

Taudien et al., Apr. 19, 2010, Haplotyping and copy number estimation of the highly polymorphic human beta-defensin locus on 8p23 by 454 amplicon sequencing. BMC Genomics. 11:252.
The Tibbs Times, UNC bioscience newsletter, Apr. 2010, 17 pages.
Tomaz et al., Aug. 2010, Differential methylation as a cause of allele dropout at the imprinted GNAS locus. Genet Test Mol Biomarkers. 14(4):455-460.
Treutlein et al., May 15, 2014, Reconstructing lineage hierarchies of the distal lung epithelium using single-cell RNA-seq. Nature. 509(7500):371-375.
Velculescu et al., 1995, Serial Analysis of Gene Expression. Science, 270:484-487.
Velculescu et al., 1997, Characterization of the Yeast Transcriptome. Cell, 88:243-251.
Vogelstein et al., 1999, Digital PCR. Proc. Natl. Acad. Sci., 96(16):9236-9241.
Walker et al., Jan. 1, 1992, Isothermal in vitro amplification of DNA by a restriction enzyme/DNA polymerase system. Proc Natl Acad Sci U S A., 89(1):392-396.
Walsh et al., Jul. 13, 2010, Detection of inherited mutations for breast and ovarian cancer using genomic capture and massively parallel sequencing. Proc Natl Acad Sci U S A. 107(28):12629-12633.
Wang et al., 2009, RNA-Seq: a revolutionary tool for transcriptomics. Nature Reviews Genetics, 10:57-63.
Wang et al., Oct. 2010, iCLIP predicts the dual splicing effects of TIA-RNA interactions, PLoS Biol, 8(10):e1000530.
Weber et al., Sep. 15, 2003, A real-time polymerase chain reaction assay for quantification of allele ratios and correction of amplification bias. Anal Biochem. 320(2):252-258.
Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nanogram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage. Genome Res. 19(9):1586-1592.
Zhang et al., Jun. 19, 2012, DNA-based hybridization chain reaction for amplified bioelectronic signal and ultrasensitive detection of proteins.,Anal Chem., 84(12),5392-5399.
Zhang et al., Mar. 20, 2011, The impact of next-generation sequencing on genomics. J Genet Genomics. 38(3):95-109.
Zhao et al., 2005, Homozygous Deletions and Chromosome Amplifications in Human Lung Carcinomas Revealed by Single Nucleotide Polymorphism Array Analysis. Cancer Research, 65:5561-5570.
Zhou et al., 2001, Counting alleles reveals a connection between chromosome 18q loss and vascular invasion. Nature Biotechnology, 19:78-81.
Office action dated Oct. 3, 2013 for U.S. Appl. No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
International Search Report and Written Opinion dated Jun. 6, 2012 in PCT/US11/065291.
Restriction Requirement dated Mar. 15, 2016 in U.S. Appl. No. 14/381,488.
International Search Report and Written Opinion dated Sep. 6, 2013 in PCT/US13/028103.
European search report and search opinion dated Jul. 17, 2015 for EP Application No. 13755319.4.
Search and Examination Report dated Aug. 6, 2014 for GB Patent Application No. 1408829.8.
Search Report and Written Opinion dated Mar. 1, 2016 in Singapore patent application No. 1120140527W.
International search report and written opinion dated Aug. 16, 2013 for PCT/US2013/027891.
Extended European Search Report dated Dec. 15, 2015 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
International Search Report and Written Opinion dated Feb. 3, 2015 in PCT/US/14/053301.
Search and Examination Report dated Aug. 26, 2015 in GB Patent Application No. 1511591.8.
Examination Report dated Feb. 19, 2016 in Great Britain patent application No. GB1511591.8.
International search report and written opinion dated Dec. 19, 2014 for PCT Application No. US2014/059542.
International search report and written opinion dated May 7, 2012 for PCT/IB2011/003160.
Notice of opposition dated Jul. 22, 2015 for EP Application No. 11810645.9.
Notice of opposition dated Jul. 9, 2015 for EP Application No. 11810645.9.
BD Biosciences, 2013, BD FACSJazz™, product brochure, 16 pages.
BD Biosciences, 2014, BD FACSJazz™ Cell Sorter: Filter Guide, 4 pages.
BD Biosciences, 2013, BD FACSJazz™ Technical Specifications, 4 pages.
BD Biosciences, Getting Started Guide for Using BD FACSJazz™ Cell Sorters with BD FACS™ Software Sorter Software, 14 pages, date not available, downloaded from internet on Mar. 30, 2016.
Anderson, Feb. 11, 2014, Study describes RNA sequencing applications for molecular indexing methods, genomeweb.com, 5 pp.
Bioscribe, Feb. 5, 2015, Massively parallel sequencing technology for single-cell gene expression published (press release), 3 pp.
Brisco et al., Jun. 25, 2012, Quantification of RNA integrity and its use for measurement of transcript number, Nucleic Acids Research, 40(18):e144.
Butkus, Feb. 6, 2014, Cellular research set to launch first gene expression platform using 'molecular indexing' technology, genomeweb.com, 5 pp.

(56) References Cited

OTHER PUBLICATIONS

Gong et al., 2010, Massively parallel detection of gene expression in single cells using subnanolitre wells, Lab Chip, 10:2334-2337.
Dunker et al., May 21, 2015, Single-cell transcriptomics enters the age of mass production, Molecular Cell, 58:563-564.
Klein et al., May 21, 2015, Droplet barcoding for single-cell transcriptomics applied to embryonic stem cells, Cell, 161:1187-1201.
Kolodziejczyk et al., May 21, 2015, The technology and biology of single-cell RNA sequencing, Molecular Cell, 58:610-620.
Lamble et al., Nov. 20, 2013, Improved workflows for high throughput library preparation using the transposome-based nextera system, BMC Biotechnology, 13(1):104.
Lee et al., 2010, Large-scale arrays of picolitre chambers for single-cell analysis of large cell populations, Lab Chip, 10:2952-2958.
Liu et al., Single-cell transcriptome sequencing: recent advances and remaining challenges, F1000Research 2016, 5(F1000 Faculty Rev):182, 9 pp.
Marcus et a., 2006, Microfluidic single-cell mRNA isolation and analysis, Ana. Chem. 78:3084-3089.
Martinez et al., Jul. 2012, A microfluidic approach to encapsulate living cells in uniform alginate hydrogel microparticles, Macromol. Biosci, 12(7):946-951.
Nadai et al., 2008, Protocol for nearly full-length sequencing of HIV-1 RNA from plasma, PLoS ONE, 3(1):e1420.
Nagai et al., 2001, Development of a microchamber array for picoleter PCR, Anal. Chem., 73:1043-1047.
Navin et al., 2015, The first five years of single-cell cancer genomics and beyond, Genome Research, 25(10):1499-1507.
Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.
Rajeevan et al., Oct. 2003, Global amplification of sense RNA: a novel method to replicate and archive mRNA for gene expression analysis, Genomics, 82(4):491-497.
Stratagene 1998 Catalog, Gene Characterization Kits, p. 39.
Vandesompele et al., Jun. 18, 2002, Accurate normalization of real-time quantitative RT-PCR data by geometric averaging of multiple internal control genes, Genome Biology, 3(7).
Warren et al., Nov. 21, 2006, Transcription factor profiling in individual hematopoietic progenitors by digital RT-PCR, PNAS, 103(47):17807-17812.
Weiner et al., Apr. 2008, Kits and their unique role in molecular biology: a brief retrospective, BioTechniques, 44:701-704.
White et al., Aug. 23, 2011, High-throughput microfluidic single-cell RT-qPCR, PNAS, 108(34):13999-14004.
Office Action dated Oct. 11, 2016 in U.S. Appl. No. 15/224,460.
Office Action dated Aug. 12, 2016 in U.S. Appl. No. 14/381,488.
Office action dated Aug. 17, 2016 for U.S. Appl. No. 14/800,526.
Office Action dated Oct. 25, 2015 in U.S. Appl. No. 14/872,337.
Office action dated Sep. 26, 2016 in U.S. Appl. No. 15/167,807.
Written Opinion dated Sep. 27, 2016 in PCT/US16/019962.
International Search Report and Written Opinion dated Aug. 9, 2016 in PCT/US16/019971.
International Search Report and Written Opinion dated Sep. 28, 2016 in PCT/US16/028694.
International Search Report and Written Opinion dated Sep. 27, 2016 in PCT/US16/034473.
Algae, Wikipedia.org, accessed Mar. 4, 2016, 20 pp.
Archaea, Wikipedia.org, accessed May 11, 2016, 26 pp.
Buschmann et al., Aug. 7, 2014, Enhancing the detection of barcoded reads in high throughput DNA sequencing DNA by controlling the false discovery rate, BMC Bioinformatics, 15(1):264.
Custom Antibody Services, Precision Antibody, accessed Apr. 16, 2014, 2 pp.
Fish, Wikipedia.org, accessed Nov. 2, 2014, 11 pp.
Fungus, Wikipedia.org, accessed Jun. 3, 2013, 28 pp.
How many species of bacteria are there? Wisegeek.org, accessed Jan. 21, 2014, 2 pp.
Jabara et al., Dec. 3, 2011, Accurate sampling and deep sequencing of the HIV-1 protease gene using a Primer ID, Supporting Information, 10.1073/pnas.111004108.
List of sequenced bacterial genomes, Wikipedia.org, accessed Jan. 24, 2014, 57 pp.
Mammal, Wikipedia.org, accessed Sep. 22, 2011, 16 pp.
Murinae, Wikipedia.org, accessed Mar. 18, 2013, 21 pp.
Peng et al., Mar. 11, 2016, Reducing amplification artifacts in high multiplex amplicon sequencing by using molecular barcodes, BMC Genomics, retrieved from the internet: url:http://bmcgenomics.biomedcentral.com/articles/0.1186/s12864-015-1806-8, 14 pp.
Plant, Wikipedia.org, accessed Aug. 28, 2015, 14 pp.
Protozoa, Wikipedia.org, accessed May 11, 2016, 10 pp.
Sommer et al., Nov. 16, 1989, Minimal homology requirements for PCR primers, Nucleic Acids Research, 17(16):6749.
Virus, Wikipedia.org, accessed Nov. 24, 2012, 34 pp.
Office Action dated May 8, 2017 in U.S. Appl. No. 15/224,460.
Office Action dated Jul. 28, 2017 in U.S. Appl. No. 14/975,441.
Office Action dated Jun. 7, 2017 in U.S. Appl. No. 14/381,488.
Office Action dated Nov. 16, 2017 in U.S. Appl. No. 14/381,488.
Examination Report dated Oct. 24, 2017 in Australian patent application No. 2013226081.
Office Action dated Feb. 17, 2017 in Canadian patent application No. 2,865,575.
Office Action dated Jul. 14, 2017 in Chinese patent application No. 201380022187.9.
Final Decision dated Aug. 30, 2017 in Japanese patent application No. 2014-558975.
Written Opinion dated May 26, 2017 in Singapore patent application No. 11201405274W.
Examination Report dated Apr. 10, 2017 in European patent application No. 14761937.3.
Examination Report dated Oct. 10, 2017 in European patent application No. 14761937.3.
Office Action dated Mar. 24, 2017 in U.S. Appl. No. 15/409,355.
Office Action dated Oct. 16, 2017 in U.S. Appl. No. 15/409,355.
Office Action dated Nov. 9, 2017 in U.S. Appl. No. 15/004,618.
Office Action dated Nov. 1, 2017 in U.S. Appl. No. 15/667,125.
Office Action dated Sep. 8, 2017 in U.S. Appl. No. 15/134,967.
International Search Report and Written Opinion dated Sep. 8, 2017 in PCT/US2017/030097.
International Search Report and Written Opinion dated Aug. 7, 2017 in PCT/US2017/034576.
Applied Biosystems, Apr. 2008, SOLiD™ System Barcoding, Application Note, 4 pp.
Bontoux et al, "Integrating whole transcriptome assays on a lab-on-a-chip for single cell gene profiling", Lab on a Chip, (2008) vol. 8, No. 3, pp. 443-450.
Brady et al., "Construction of cDNA libraries form single cells", Methods in Enzymology, Academic Press, US, (1993) vol. 225, doi:10.1016/0076-6879(93)25039-5, ISSN 0076-6879, pp. 611-623.
Clontech Laboratories, Inc., May 15, 2007, Super SMART™ PCR cDNA Synthesis Kit User Manual, 39 pp.
Cloonan et al., "Stem cell transcriptome profiling via massive-scale mRNA sequencing", Nature Methods, (Jul. 2008) vol. 5, No. 7, pp. 613-619.
Costa et al., Aug. 22, 2012, Single-tube nested real-time PCR as a new highly sensitive approach to trace hazelnut, J. Agric Food Chem, 60(33):8103-8110.
Di Carlo et al., Dec. 1, 2008. Dynamic single-cell analysis for quantitative biology, Analytical Chemistry, 78(23):7918-7925.
Eberwine et al., "Analysis of gene expression in single live neurons", Proc. Natl, Acad. Sci. USA, (Apr. 1992) vol. 89, No. 7, pp. 3010-3014
Harbers, "The current status of cDNA cloning", Genomics, (2008) vol. 91, No. 3, pp. 232-242.
Hartmann, "Gene expression profiling of single cells on large-scale oligonucleotide arrays", Nucleic Acids Research, (Oct. 2006) vol. 34, No. 21, p. e143.

(56) References Cited

OTHER PUBLICATIONS

Islam et al, "Highly multiplexed and strand specific single-cell RNA 5' end sequencing", Nature Protocols, (2012) vol. 7, No. 5, pp. 813-828.
Karrer et al., "In situ isolation of mRNA from individual plant cells: creation of cell-specific cDNA libraries.", Proc. Natl. Acad. Sci. USA, (Apr. 1995) vol. 92, No. 9, pp. 3814-3818.
Ko et al., "RNA-conjugated template-switching RT-PCR method for generating an *Escherichia coli* cDNA library for small RNAs", Journal of Microbiological Methods, (2006) vol. 64, No. 3, pp. 297-304.
Kurimoto et al, "Global single-cell cDNA amplification to provide a template for representative high-density oligonucleotide microarray analysis", Nature Protocols, (2007) vol. 2, No. 3, pp. 739-752.
Maeda et al., "Development of a DNA barcode tagging method for monitoring dynamic changes in gene expression by using an ultra high-throughput sequencer", BioTechniques, (Jul. 2008), vol. 45, No. 1, pp. 95-97.
Mardis, "Next-generation DNA sequencing methods", Annu. Rev. Genomics Hum. Genet., (2008) vol. 9, pp. 387-402.
Marguerat et al, "Next-generation sequencing: applications beyond genomes", Biochemical Society Transactions, (2008) vol. 36, No. 5, pp. 1091-1096.
Meyer et al., "Parallel tagged sequencing on the 454 platform", Nature Protocols, (2008) vol. 3, No. 2, pp. 267-278
Shendure et al., "Next-generation DNA sequencing", Nature Biotechnology, (Oct. 2008) vol. 26, No. 10, pp. 1135-1145.
Subkhankulova et al., "Comparative evaluation of linear and exponential amplification techniques for expression profiling at the single cell level", Genome Biology, (Mar. 2006) vol. 7, No. R18, pp. 1-16.
Tang et al, "RNA-Seq analysis to capture the transcriptorne landscape of a single cell", Nature Protocols, (2010) vol. 5, No. 3, pp. 516-535.
Zhu et al., "Reverse transcriptase template switching: a SMART approach for full-length cDNA library construction.", BioTechniques, (Apr. 2001) vol. 30, No. 4, pp. 892-897.
Examination report dated Sep. 5, 2018 in European patent application No. 16710357.1.
Office action dated Jan. 9, 2018 in U.S. Appl. No. 15/217,896.
Office action dated Jan. 12, 2018 in U.S. Appl. No. 15/217,886.
Office action dated Jul. 20, 2018 in U.S. Appl. No. 15/217,886.
Office Action dated May 10, 2018 in U.S. Appl. No. 14/381,488.
Office Action dated Feb. 15, 2018 in Canadian patent application No. 2,865,575.
Extended European Search Report dated Feb. 8, 2018 in patent application No. 17202409.3.
Notice of Reasons for Rejection dated Apr. 2, 2018 in Japanese patent application No. 2014-558975.
Examination Report dated Mar. 16, 2018 in European patent application No. 13754428.4.
Pre-interview communication dated Oct. 15, 2018 in U.S. Appl. No. 15/987,851.
Examination Report No. 1 for standard patent application, dated Jul. 20, 2018 Australian patent application No. 2014312208.
Examination Report dated Jan. 3, 2018 in GB patent application No. 1609740.4.
Third Party Observation dated Jun. 14, 2018 in Japanese patent application No. 2016-537867.
Official Action dated Jul. 30, 2018 in Japanese patent application No. 2016-537867.
First Office Action dated Dec. 19, 2017 in Chinese patent application No. 201480061859.1.
Notice of Reasons for Rejection dated Aug. 31, 2018 in Japanese patent application No. 2016-520632.
Office Action dated Jul. 25, 2018 in U.S. Appl. No. 15/108,268.
Office Action dated Jul. 5. 2018 in U.S. Appl. No. 15/004,618.
Extended European Search Report dated Jun. 11, 2018 in European patent application No. 16740872.3.
Examination report dated Sep. 26, 2018 in European patent application No. 16714081.3.
Office Action dated Mar. 8, 2018 in U.S. Appl. No. 15/608,780.
Statement of Opposition of Strawman Limited filed against European Patent No. EP2414548B1 on Jul. 19, 2016.
Statement of Opposition flied against European Patent No. EP2414548B1 on Jul. 26, 2016.
Statement of Opposition filed against European Patent No. EP2414548B1 on Jul. 21, 2016.
Submission dated Jan. 15, 2018 by Strawman Limited in preparation for upcoming oral proceedings in opposition against European Patent No. EP2414548B1.
Submission dated Jan. 15, 2018 by Vossius & Partner in preparation for upcoming oral proceedings in opposition against European Patent No. EP2414548B1.
Third-Party Pre-Issuance Submission filed on Jun. 16, 2018 for U.S. Appl. No. 15/847,752.
Third-Party Pre-Issuance Submission filed on Jun. 6, 2018 for U.S. Appl. No. 15/847,752.
Thirf-Party Pre-Issuance Submission filed on May 21, 218 for U.S. Appl. No. 15/847,752.

\* cited by examiner

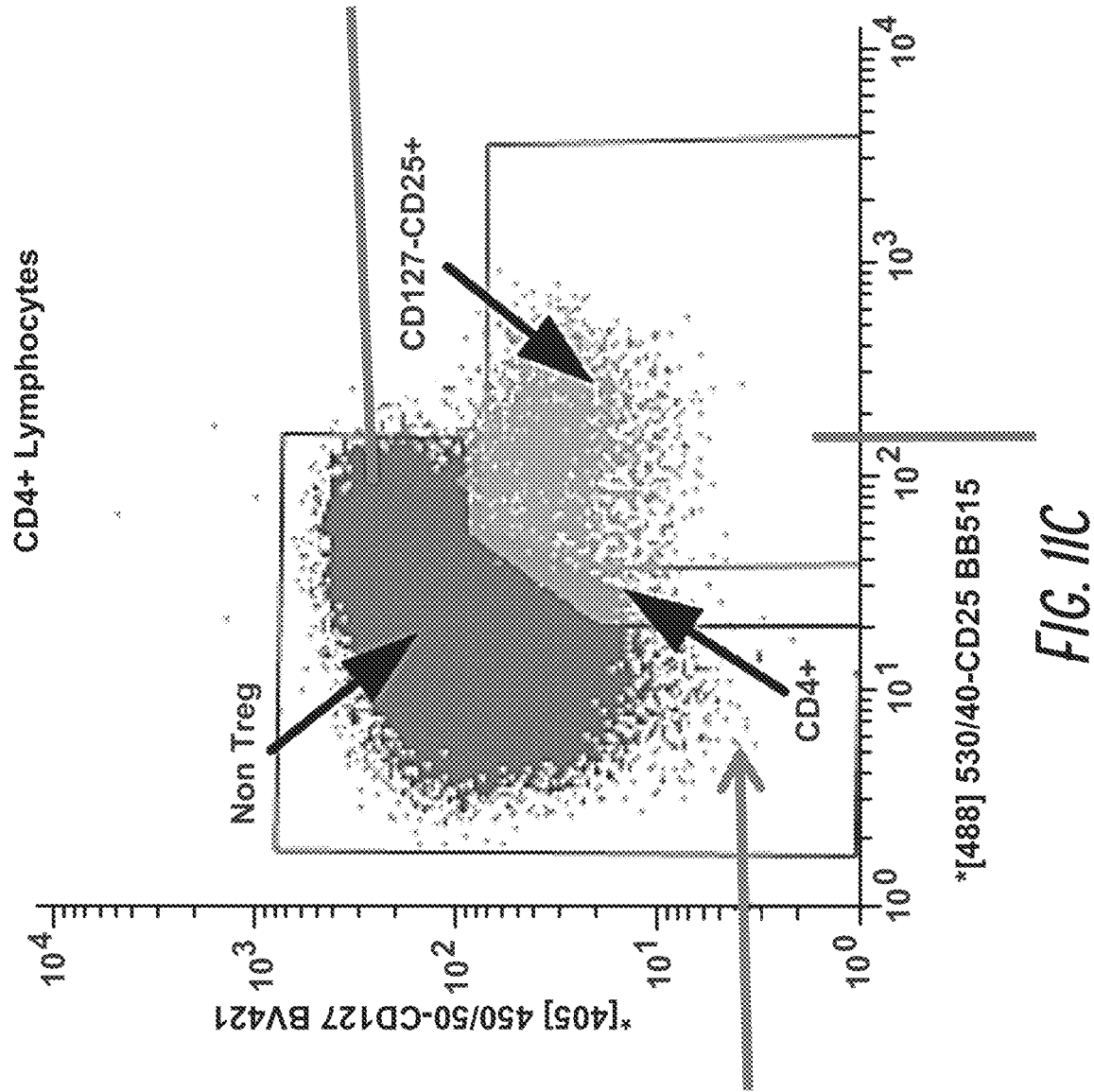

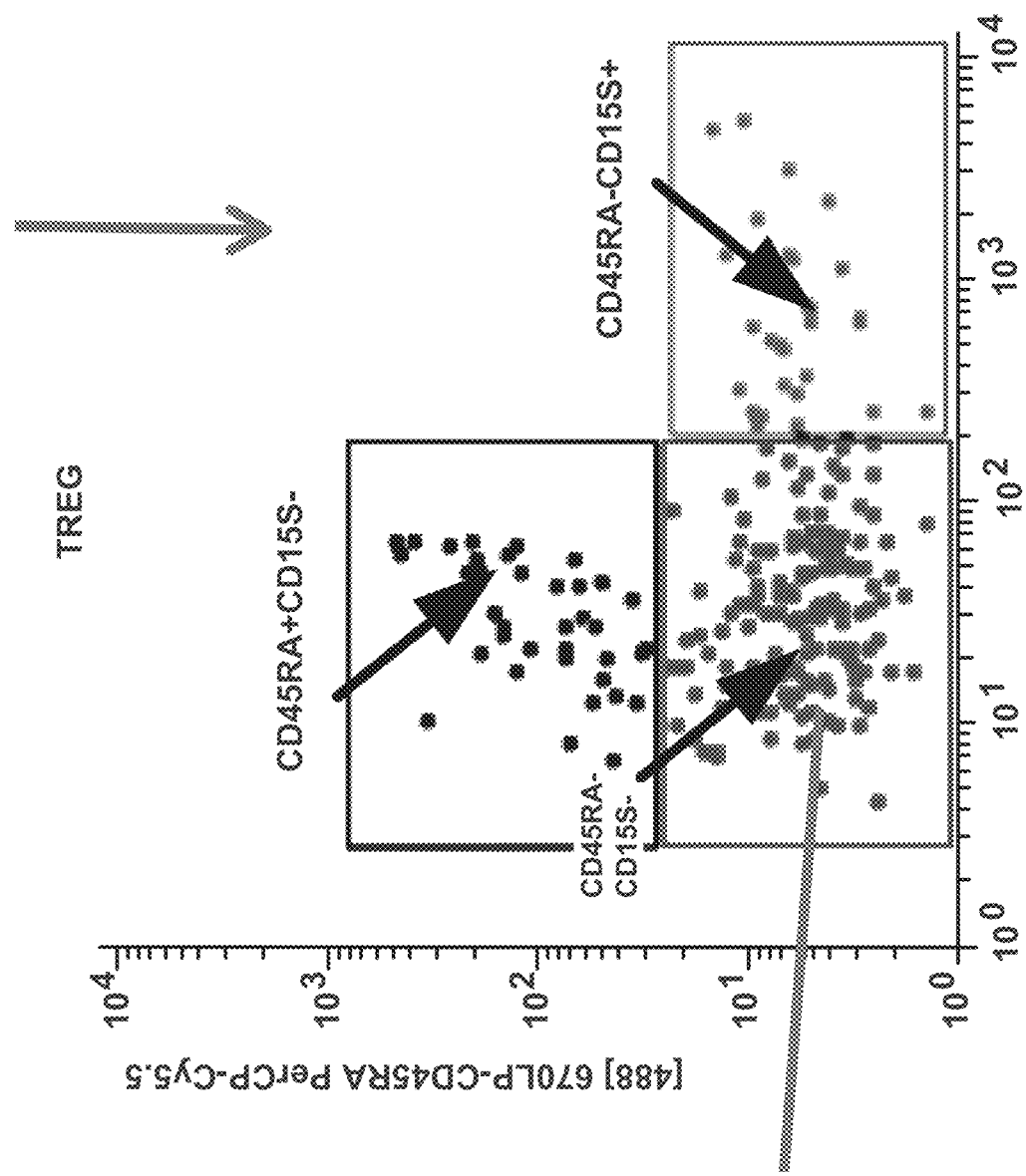

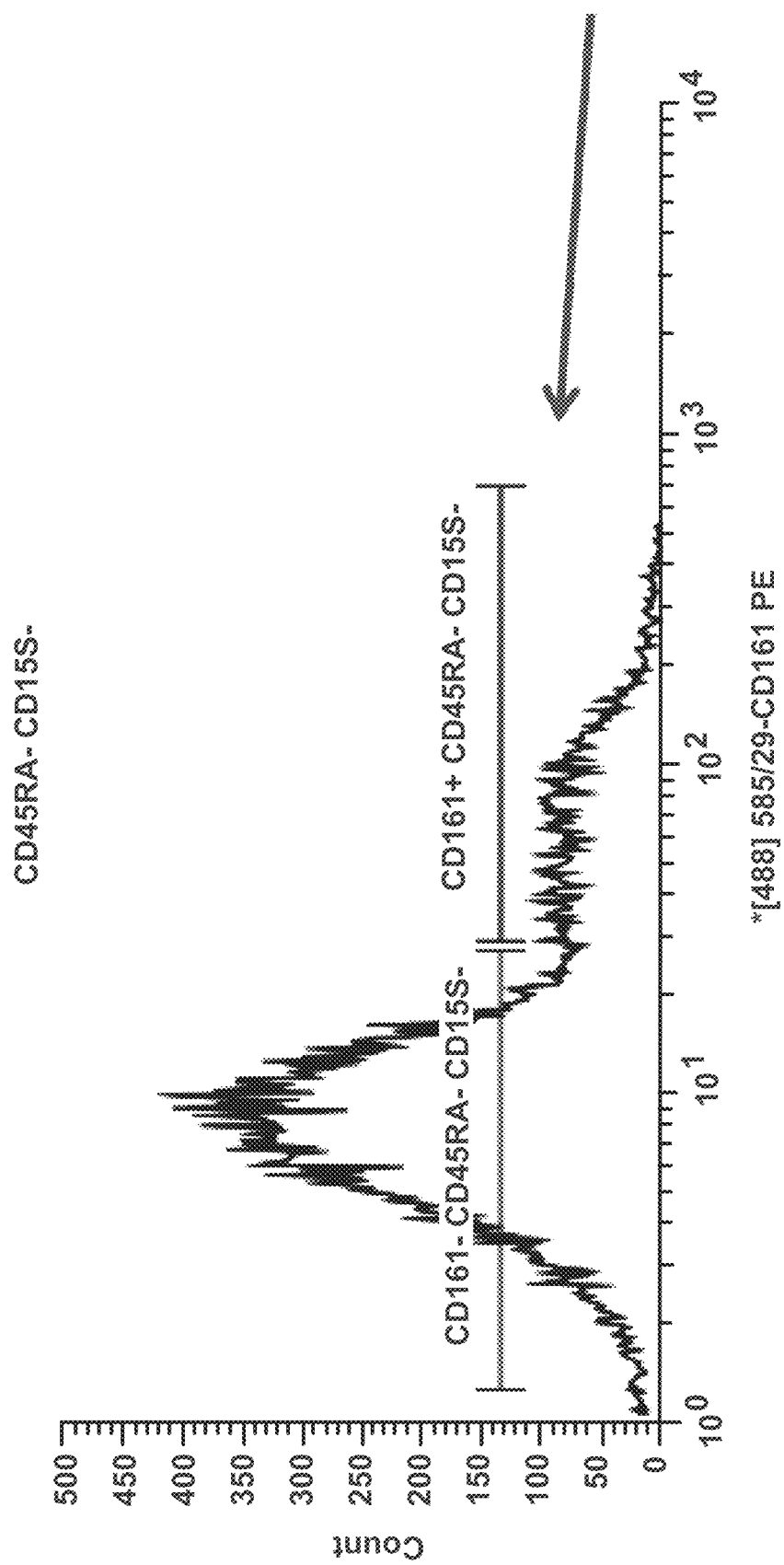

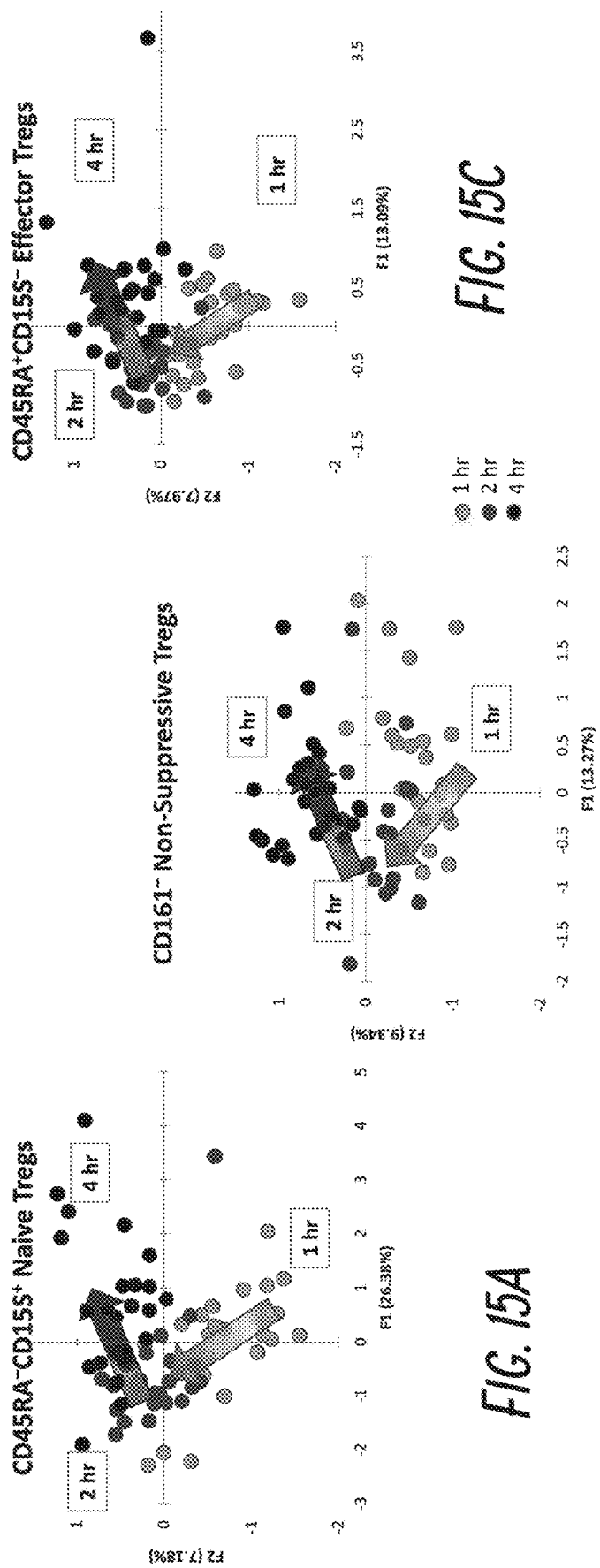

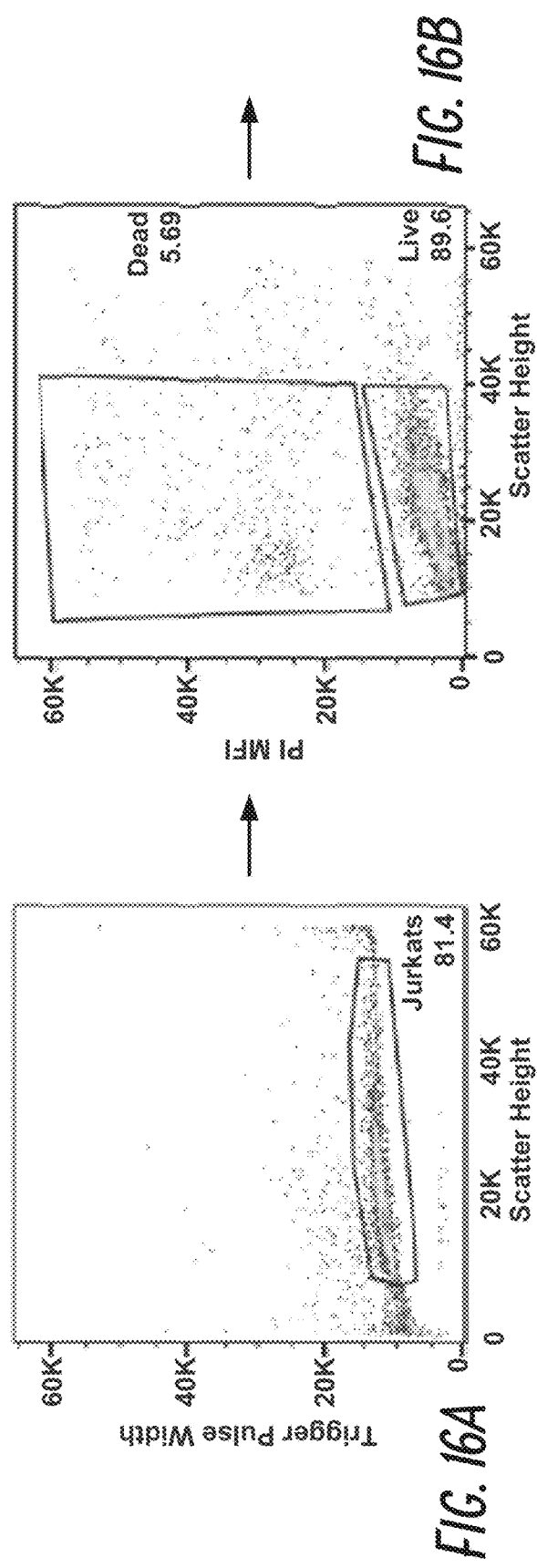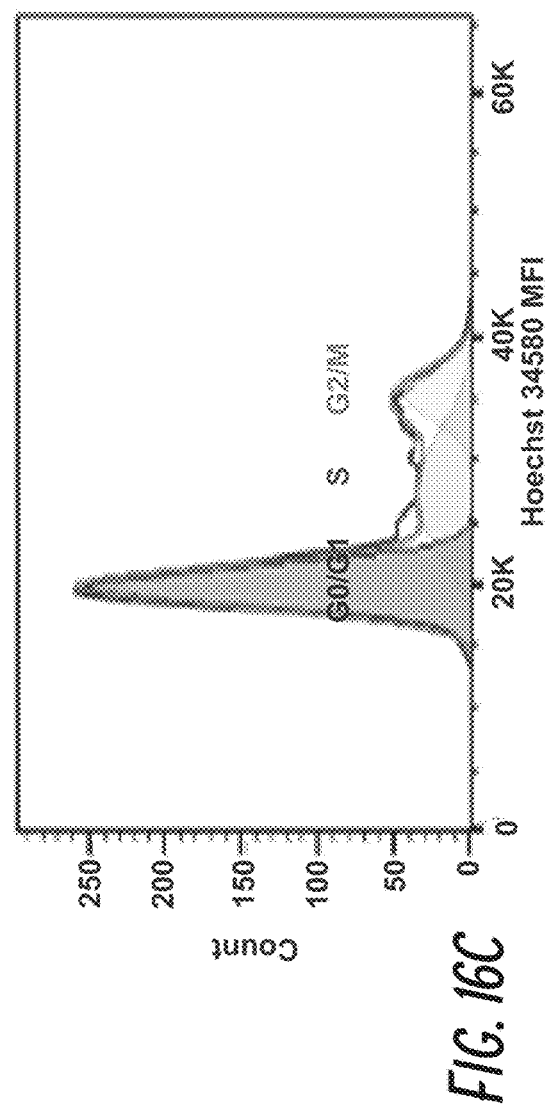
FIG. 16A   FIG. 16B   FIG. 16C

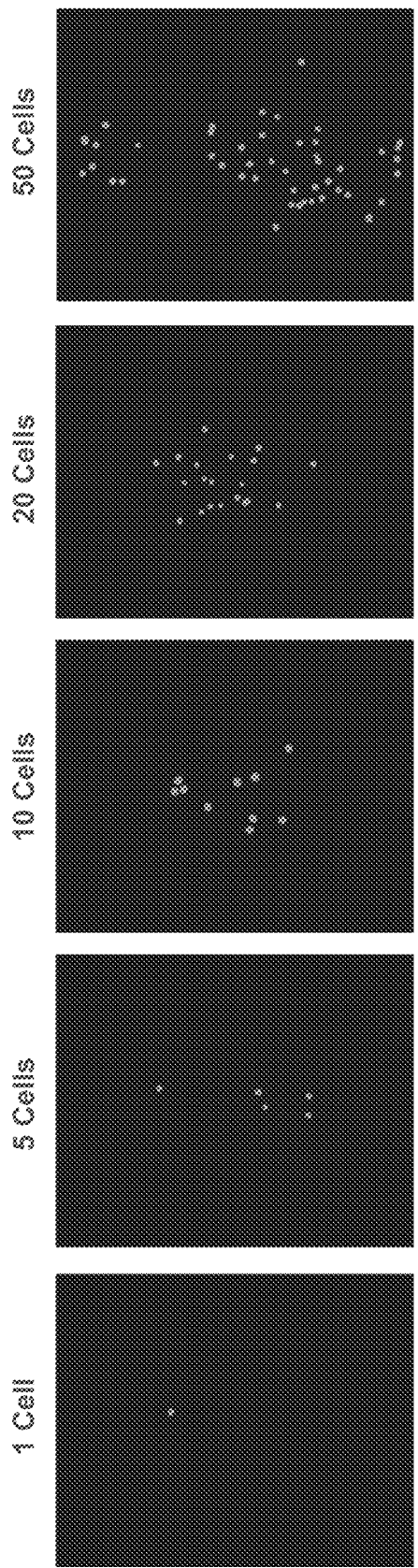
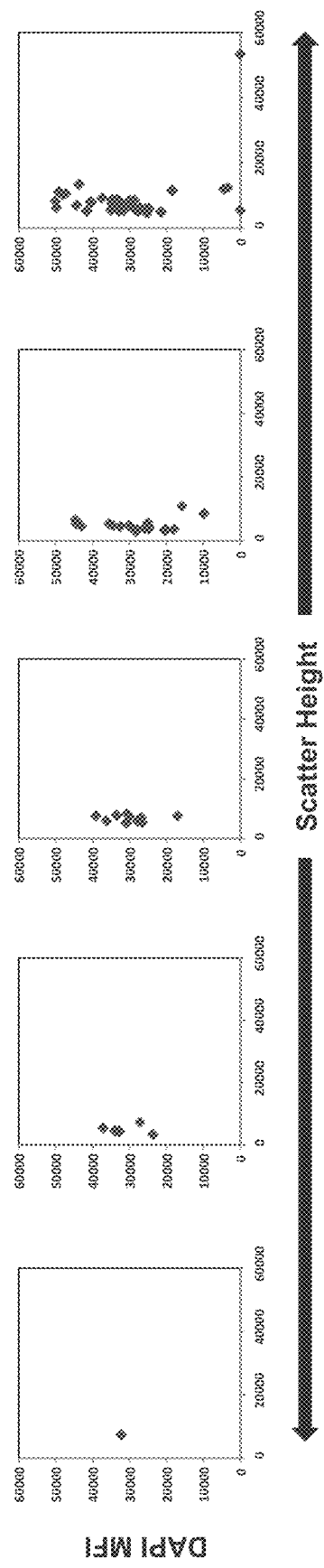
FIG. 17A
FIG. 17B

| Gene | Other Name | Category | RefSeq# | Gene | Other Name | Category | RefSeq# |
|---|---|---|---|---|---|---|---|
| ABCB1 | CD243/ MDR-1 | ATP pump | NM_000927 | MAPK1 | ERK2 | Kinase | NM_002745 |
| ABCG2 | CD338 | ATP pump | NM_004827 | MAPK3 | ERK1 | Kinase | NM_002746 |
| ADAM23 | MDC-3 | Mem GP | NM_003812 | MAPK8 | JNK1 | Kinase | NM_002750 |
| AKT1 | PKB alpha | Kinase | NM_005163 | MGMT | EC 2.1.1.63 | Protein Coding | NM_002412 |
| APC | Activated Protein C | Protease | NM_000038 | MKI67 | Antigen KI-67 | Protein Coding | NM_002417 |
| AR | DHTR | Hormone Recep | NM_000044 | MLH1 | COCA2 | Protein Coding | NM_000249 |
| ATM | ATD/ATA/AT Protein | Kinase | NM_000051 | MMP2 | CLG4A | MMP Family | NM_004530 |
| BAD | BCL2L8/BBC2 | Kinase | NM_004322 | MMP9 | CLG4B | MMP Family | NM_004994 |
| BCL2 | IGSM | Kinase | NM_000633 | MUC1 | PUM/Episialin | Mucin Family | NM_001018016 |
| BIRC5 | API4/EPR-1 | Apop Inhibitor | NM_001168 | MYB | C-Myb/Efg | Trans. Factor | NM_001130173 |
| BRCA1 | BRCC1/PSCP | Tumor Sup | NM_007294 | MYC | C-Myc/MRTL | Trans. Factor | NM_002467 |
| BRCA2 | FAD/FAD1/BRCC2 | Tumor Sup | NM_000059 | NME1 | NDP Kinase A | Kinase | NM_000269 |
| C4A | C4A2/C4AD/CO4 | Compliment | NM_001252204 | NOTCH1 | TAN1/HN1 | Notch Family | NM_017617 |
| CA12 | CA-XII | C Anhydrases | NM_001218 | NR3C1 | GRL/GCR | Trans. Factor | NM_000176 |
| CCNA1 | Cyclin A1/CT146 | Cyclin | NM_003914 | PGR | PR/NR3C3 | Hormone | NM_000926 |
| CCND1 | BCL1/PRAD1 | Cyclin | NM_053056 | PLAU | UPA/QPD | Protease | NM_002658 |
| CCND2 | MPPH3 | Cyclin | NM_001759 | PRDM2 | RIZ/MTB-ZF | Tumor Sup. | NM_015866 |
| CCNE1 | Cyclin E1 | Cyclin | NM_001238 | PSMB2 | HC7-I | Proteasome | NM_002796 |
| CDH1 | CD324/LCAM | Cadherins | NM_004360 | PSMB4 | HN3/PROS-26 | Proteasome | NM_002796 |
| CDH13 | T-cad/CDHH | Cadherins | NM_001257 | PTEN | MMAC1/TEP1 | Tumor Sup. | NM_000314 |
| CDK2 | Cdk1 | Kinase | NM_001798 | PTGS2 | COX-2 | Cyclooxygenase | NM_000963 |
| CD326 | EPCAM | Cell Adhesion | NM_002354 | PYCARD | TMS1/ASC | Adaptor Protein | NM_013258 |
| CDKN1A | CIP1/WAF1 | Tumor Sup | NM_000389 | RAB7A | CMT2B | Oncogene | NM_004637 |
| CDKN1C | BWCR/KIP2 | Tumor Sup | NM_000076 | RARA | RAR-Alpha | Trans. Regulator | NM_000964 |
| CDKN2A | ARF/INK4 | Tumor Sup | NM_000077 | RARB | RAR-Beta | Trans. Regulator | NM_000965 |
| CSF1 | MCSF | Cytokine | NM_000757 | RASSF1 | RDA32 | Tumor Sup. | NM_007182 |
| CST6 | Cystatin E/M | Cystatin | NM_001323 | RB1 | PRb/RB | Tumor Sup. | NM_000321 |
| CTNNB1 | beta-catenin | Adheren | NM_001904 | REEP5 | C5orf19 | GPCR | NM_005669 |
| CTSD | CLN10/CPSD | Protease | NM_001909 | RNB6 | EVL | Protein Coding | NM_016337 |
| EGF | HOMG4/URG | Growth Factor | NM_001963 | SERPINE1 | PLANH1 | Proteinase | NM_000602 |
| EGFR | mENA/ERBB | Growth Factor | NM_005228 | SFN | Stratifin | Adaptor Protein | NM_006142 |
| EMAP-2 | AIMP1 | Cytokine | NM_001193268 | SFRP1 | SARP2 | SFRP | NM_003012 |
| ERBB2 | HER2/NEU | EGFR | NM_004448 | SLC39A6 | ZIP-6/LIV-1 | Zinc Transporter | NM_012319 |
| ERBB3 | HER3 | EGFR | NM_001982 | SLIT2 | SLIL3 | Cell Migration | NM_004787 |
| ESR1 | ER/ESR/ESTRR | Hormone Recep | NM_000125 | SNAI2 | SLUG/WS2D | Trans. Factor | NM_003068 |
| ESR2 | ErB/ESRB | Hormone Recep | NM_001437 | SRC | SRC1/ASV | Proto-oncogene | NM_005417 |
| FOXA1 | HNF3A/TCF3A | DNA Bind. Prot. | NM_004496 | TBC1D9 | MDR1 | GRAM Domain | NM_015130 |
| GATA3 | HDR/HDRS | Trans. Factor | NM_003051 | TCTN1 | TECT1 | Transmem. Prot. | NM_001173975 |
| GLI1 | GLI | Trans. Factor | NM_005269 | TFF3 | ITF/HP1.B | Trefoil Family | NM_003226 |
| GPI | G-6-P Isomerase | Isomerase | NM_000175 | TGFB1 | TGF-beta-1 | Cytokine | NM_000660 |
| GRB7 | B47 | GFR | NM_005310 | THBS1 | TSP1/TSP | Mem GP | NM_003246 |
| GSTP1 | GST3 | Protein Coding | NM_000852 | TP73 | P73 | Trans. Factor | NM_005427 |
| HIC1 | ZBRB29 | Tumor Repress. | NM_006497 | TWIST1 | H-Twist/CRS1 | Trans. Factor | NM_000474 |
| HPRT1 | HPRT/HGPRTase | Transferase | NM_000194 | VEGFA | VPF/VEGF | Growth Factor | NM_003376 |
| ID1 | BHLHb24/ID | Trans. Factor | NM_002165 | XBP1 | TREB-5 | Trans. Factor | NM_005080 |
| IGF1 | MGF/IBP1 | Growth Factor | NM_000618 | CD30 | CD3_Delta | Mem GP | NM_000732 * |
| IGF1R | IGF1-Receptor | GFR | NM_000875 | CD3E | CD3_Epsilon | Mem GP | NM_000733 * |
| IGFBP3 | IGF-Binding Prot. | Growth Factor | NM_000598 | CD3G | CD3-Gamma | Mem GP | NM_000073_ALT * |
| IL6 | IFNB2/HSF | Cytokine | NM_000600 | TCF7 | HMG-Box | Trans. Factor | NM_003202 * |
| JUN | P39/AP1 | Oncogene | NM_002228 | ALCAM | CD166 | Mem GP | NM_001627 * |
| KRT18 | Cytokeratin-18 | Keratin | NM_000224 | CD25 | NA | Mem GP | NM_013230 * |
| KRT19 | Cytokeratin-19 | Keratin | NM_002276 | ITGA6 | CD49f | Mem GP | NM_000210 * |
| KRT5 | Cytokeratin-5 | Keratin | NM_000424 | THY1 | CD90 | Mem GP | NM_006288 * |
| KRT8 | Cytokeratin-8 | Keratin | NM_002273 | PROM1 | CD133 | Mem GP | NM_006017 * |
| LAMP1 | CD107a | Mem GP | NM_005561 | CXCR4 | CD184 | Mem GP | NM_003467.2 * |

*supplemental additions

FIG. 22

HIGH-THROUGHPUT SINGLE-CELL ANALYSIS COMBINING PROTEOMIC AND GENOMIC INFORMATION

RELATED APPLICATIONS

The present application claims priority under 35 U.S.C. § 119(e) to U.S. Provisional Application No. 62/118,412, filed on Feb. 19, 2015. The content of this related application is herein expressly incorporated by reference in its entirety.

BACKGROUND

Field

The present disclosure relates generally to the field of molecular biology, and more particularly to high-throughput single-cell analysis.

Description of the Related Art

Methods and techniques for flow cytometry are useful in cell analysis, in particular deciphering expression profiles of cell surface proteins to determine the states of cells. Methods and techniques for mRNA sequencing are useful in cell analysis, in particular deciphering gene expression profiles to determine the states of cells using, for example, next generation sequencing ("NGS"). When performed on samples of both cells of interest and cells not of interest, these methods and techniques determine the average states of the cells in the samples. However, cell-to-cell variations can exist among different cells, thus these methods and techniques can have poor signal-to-noise ratios for cells of interest. Also, the gene expression profiles of cells may not be accurate proxies of the protein expression profiles of cells. Thus, there is a need for improved low cost methods of isolating and sequencing single cells, including cells of interest, as well as methods capable of efficiently and effectively combining genomic and proteomic information for cell analysis.

SUMMARY

The present disclosure provides methods for single-cell sequencing. In some embodiments, the methods include enriching a sample comprising a plurality of cells for cells of interest to produce an enriched cell sample; isolating one or more cells of interest in the enriched cell sample; and obtaining sequence information of one or more polynucleotides from each of the one or more isolated cells, wherein obtaining sequence information includes generating a molecularly indexed polynucleotide library from the one or more isolated cells. In some embodiments, the methods include enriching a sample comprising a plurality of cells for cells of interest to produce an enriched cell sample, wherein enriching the sample includes focusing cells of interest in the sample using acoustic focusing; isolating one or more cells of interest in the enriched cell sample; and obtaining sequence information of one or more polynucleotides from each of the one or more isolated cells.

In some embodiments, enriching the sample includes one or more of focusing cells of interest in the sample and depleting cells not of interest in the sample. Focusing the cells of interest can include focusing the cells of interest in the sample into a core stream of cells using, for example, acoustic focusing. Focusing the cells of interest in the sample can include focusing the cells of interest in the sample based on cell size. For example, focusing the cells of interest comprises focusing cells each having a size within a predetermined range. In some embodiments, depleting cells not of interest in the sample comprises depleting cells having a size that does not fall into the predetermined range. Acoustic focusing can include: suspending the plurality of cells in the sample in an elongated fluid-filled channel; and exposing said channel to an axial acoustic standing wave field parallel to the direction of flow, wherein said axial acoustic standing wave field drives the plurality of cells to positions of potential force minimum along the center axis of said channel to result in uniformly spaced cells. In some embodiments, focusing cells of interest includes hydrodynamic focusing, magnetic field focusing, electric field focusing, gravitational field focusing, optical field focusing, or a combination thereof. The method can, in some embodiments, include depleting one or more of interfering cells and debris in the sample.

In some embodiments, isolating the one or more cells of interest from the enriched cell sample includes sorting cells in the enriched cell sample with a flow cytometer. The flow cytometer can utilize fluorescence-activated cell sorting. Isolating the one or more cells of interest in the sample can include depositing the one or more cells of interest in the sample into one or more microtiter plates. Each of the one or more microtiter plates can have, for example, at least 96 wells.

In some embodiments, the one or more polynucleotides include RNA, such as mRNA, and can be obtained from exosome. The sequence information can, for example, include transcript counts of at least 10 genes, for example, CD4, FOX01, CD45RO, MYC, IL1R2, PRF1, GZMK, LGALS1, IL17F, IL23R, LYNX1, PRDM1, SELL, SMAD4, ICOS, IKZF5, RORC, AHRR, CTLA4, ITGB7, ENTPD1, CCR8, TSHR, TGFB2, IL12A, IL7R, HLA-DMA, CCR5, TIAF1, BCL6, BHLHE40, CXCR4, CD307c, CD3D, GSTP1, TCF7, CD3E, RNB6, RB1, MYB, CD3G, KRT8, CDH1, ERBB3, ERBB2, TCTN1, ESR1, CDKN1A, TFF3, ABCB1, ABCG2, ADAM23, AKT1, APC, AR, ATM, BAD, BCL2, BIRC5, BRCA1, BRCA2, C4A, CAl2, CCNA1, CCND1, CCND2, CCNE1, CDH1, CDH13, CDK2, CD326, CDKN1A, CDKN1C, CDKN2A, CSF1, CST6, CTNNB1, CTSD, EGF, EGFR, EMAP-2, ERBB2, ERBB3, ESR1, ESR2, FOXA1, GATA3, GLI1, GPI, GRB7, GSTP1, HIC1, HPRT1, ID1, IGF1, IGF1R, IGFBP3, IL6, JUN, KRT18, KRT19, KRT5, KRT8, LAMP1, MAPK1, MAPK3, MAPK8, MGMT, MKI67, MLH1, MMP2, MMP9, MUC1, MYB, MYC, NME1, NOTCH1, NR3C1, PGR, PLAU, PRDM2, PSMB2, PSMB4, PTEN, PTGS2, PYCARD, RAB7A, RARA, RARB, RASSF1, RB1, REEP5, RNB6, SERPINE1, SFN, SFRP1, SLC39A6, SLIT2, SNAI2, SRC, TBC1D9. TCTN1, TFF3, TGFB1, THBS1, TP73, TWIST1, VEGFA, XBP1, CD3E, CD3G, CD3G, TCF7, ALCAM, CD25, ITGA6, THY1, PROM1, and CXCR4. In some embodiments, no more than 500 cells can be isolated from the enriched cell sample.

In some embodiments, obtaining sequence information includes sequencing the molecularly indexed polynucleotide library and possibly deconvoluting the sequencing result from sequencing the library. Deconvoluting the sequencing result, in some embodiments, includes using a software-as-a-service platform.

In some embodiments, the sample can include, or be, a biological sample, a clinical sample, an environmental sample, or a combination thereof. In some embodiments, the sample can include one or more of a biological fluid, tissue and cell from a patient. In some embodiments, the sample can include blood, urine, cerebrospinal fluid, pleural fluid, amniotic fluid, semen, saliva, bone marrow, a biopsy sample, or a combination thereof.

In some embodiments, the cells of interest in the sample include stem cells, cancer cells, blood cells, peripheral blood mononuclear cells, circulating tumor cells, breast cancer cells, cells at a cell cycle phase of desire, or a combination thereof. The methods can, in some embodiments, include one or more of determining genotype of the patient based on the obtained sequence information; determining phenotype of the patient based on the obtained sequence information; determining one or more genetic mutation of the patient based on the obtained sequence information; and predicting susceptibility of a patient to one or more diseases. At least one of the one or more diseases can be, for example, cancer or a hereditary disease. In some embodiments, less than 10%, 1%, 0.1%, or 0.01% of total number of cells in the sample are the cells of interest.

BRIEF DESCRIPTION OF THE DRAWINGS

FIG. 4A shows a schematic of labeling target molecules with a pool of labels. FIG. 4B shows a schematic of detection of labeled targets on an array having features that are label specific and target specific.

FIGS. 15A-C are PCA single-cell plots of CD45RA⁻CD15S⁺, CD161⁻non-suppressiveTregs, and CD45RA⁺CD15S⁻ effector Tregs across time points.

FIGS. 16A-C are plots showing cell cycle analysis of single cells.

FIGS. 17A-B are plots showing accurate delivery of single cells and small numbers of cells.

FIG. 19A is a PCA plot showing clustering of Jurkat cells and T47D cells into two clusters. FIGS. 19B-C are bar charts showing gene expression profiles in cluster 1 of Jurkat cells and cluster 2 of T47D cells.

FIG. 22 is a table showing the breast cancer genes analyzed with molecular indexing

DETAILED DESCRIPTION

Figure 1B:
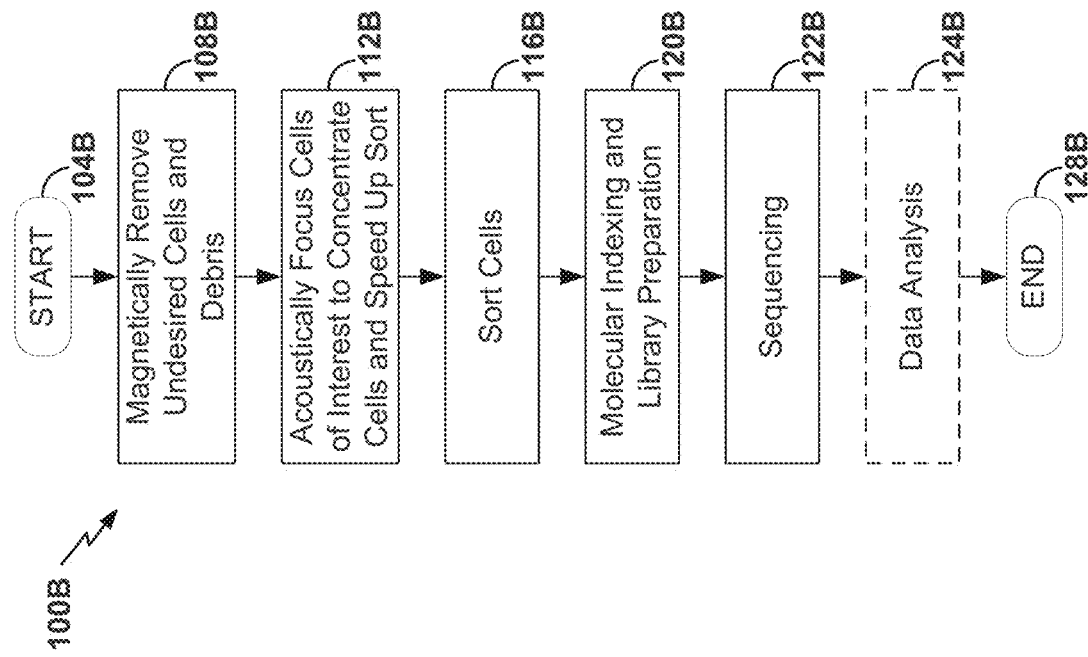
FIGS. 1A-B are flowcharts showing non-limiting exemplary workflows of cell analysis, including, for example, cell enrichment and sorting, molecular indexing, library preparation, sequencing, and data analysis.

In the following Detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated and made part of the disclosure herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

As used herein the term "adaptor" can mean a sequence to facilitate amplification or sequencing of associated nucleic acids. The associated nucleic acids can comprise target nucleic acids. The associated nucleic acids can comprise one or more of sample labels and molecular labels. The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can comprise a universal sequence. A universal sequence can be a region of nucleotide sequence that is common to two or more nucleic acid molecules. The two or more nucleic acid molecules can also have regions of sequence differences. Thus, for example, the 5' adapters can comprise identical or universal nucleic acid sequences and the 3' adapters can comprise identical or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences, the adapters providing sites for hybridization of universal primers. The adaptors at the 5' and 3' ends of the adapter-target-adapters can be the same or different.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some embodiments two or more associated species are "tethered", "attached", or "immobilized" to one another or to a common solid or semisolid surface. An association may refer to covalent or non-covalent means for attaching labels to solid or semisolid supports such as beads. An association may be a covalent bond between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "mRNA" or sometimes refer by "mRNA transcripts" include, but is not limited to pre-mRNA transcript(s), transcript processing intermediates, mature mRNA(s) ready for translation and transcripts of the gene or genes, or nucleic acids derived from the mRNA transcript(s). Transcript processing can include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

As used herein, the term "next generation sequencing" refers to sequencing technologies having increased throughput as compared to the traditional Sanger- and capillary electrophoresis-based approaches, for example with the ability to generate hundreds of thousands or millions of relatively short sequence reads at a time. Examples of next generation sequencing techniques include, but are not limited to, sequencing by synthesis, sequencing by ligation, and sequencing by hybridization. Examples of next generations sequencing methods include, but are not limited to, pyrosequencing as used by the GS Junior and GS FLX Systems (454 Life Sciences, Bradford, Conn.); sequencing by synthesis as used by Miseq and Solexa system (Illumina, Inc., San Diego, Calif.); the SOLiD™ (Sequencing by Oligonucleotide Ligation and Detection) system and Ion Torrent Sequencing systems such as the Personal Genome Machine or the Proton Sequencer (Thermo Fisher Scientific, Waltham, Mass.), and nanopore sequencing systems (Oxford Nanopore Technologies, Oxford, united Kingdom).

As used herein, the term "non-depleting reservoirs" can refer to a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

As used herein, a "nucleic acid" can generally refer to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C≡CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',:4, 5)pyrrolo[2,3-d]pyrimidin-2-one).

As used herein, the term "solid support" can refer to discrete solid or semi-solid surfaces to which a plurality of molecular labels or stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A solid support may be used interchangeably with the term "bead."

As used herein, the term "stochastic barcode" can refer to a polynucleotide sequence comprising labels. A stochastic barcode can be a polynucleotide sequence that can be used for stochastic labeling. Stochastic barcodes can be used to quantify targets within a sample. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets.

As used herein, the term "target" can refer to a composition which can be associated with a stochastic barcode or a molecular identifier label. Exemplary suitable targets for analysis by the disclosed methods, devices, and systems include oligonucleotides, DNA, RNA, mRNA, microRNA, tRNA, and the like. Targets can be single or double stranded.

In some embodiments targets can be proteins. In some embodiments targets are lipids.

The term "reverse transcriptase" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transcriptases, and group II intron reverse transcriptases. Examples of group II intron reverse transcriptases include the Lactococc s lactis L1.LtrB intron reverse transcriptase, the *Thermosynechococcus elongates* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

In the present disclosure, methods for cost-effective, high throughput, cell analysis, such as single-cell analysis, are disclosed. The methods are useful for high-resolution genomic studies, including NGS, qPCR, and microarray analysis. In some embodiments, the methods disclosed herein combine cell sorting and molecular indexing. The methods can also, in some embodiments, include an enrichment step before cell sorting and molecular indexing are performed. In some embodiments, the methods include the use of flow cytometry such as fluorescence-activated cell sorting ("FACS") to isolate cells of interest. Flow cytometers capable of isolating single cells include, but are not limited to BD (Franklin Lakes, N.J.) FACSJazz™ cell sorter and BD FACSSeg™ cell sorter. Molecular indexing techniques include, for example, the Precise™ Molecular Indexing™ technology from Cellular Research, Inc. (Palo Alto, Calif.). The combination of proteomic and genomic analyses as disclosed herein allows comprehensive investigation of cells. For example, molecular indexing techniques can be used to investigate cell activities at transcription level, e.g., quantifying mRNA transcripts in a cell of interest, and cell sorting methods can be used to investigate cell activities at translation level, e.g., determining protein expression by the cell. The knowledge of cell activities at multiple levels can provide different aspects of the cell biology and detect abnormalities in the cell, e.g., a lack of correlation between transcription and translation.

Some embodiments disclosed herein provide methods of polynucleotide sequencing, such as single-cell polynucleotide sequencing. The methods include, in some embodiments, enriching a sample comprising a plurality of cells for cells of interest to produce an enriched cell sample; isolating one or more cells of interest from the enriched cell sample; and obtaining sequence information of one or more polynucleotides from each of the one or more isolated cells. In some embodiments, the methods include: enriching a sample comprising a plurality of cells for cells of interest to produce an enriched cell sample; isolating one or more cells of interest from the enriched cell sample; and obtaining sequence information of one or more polynucleotides from each of the one or more isolated cells, wherein obtaining sequence information includes generating a molecularly indexed polynucleotide library from the one or more isolated cells. In some embodiments, enriching the sample can include, for example, focusing the cells of interest in the sample. Cells of interest can be focused into a core stream of cells using, for example, acoustic focusing.

Figure 1A:
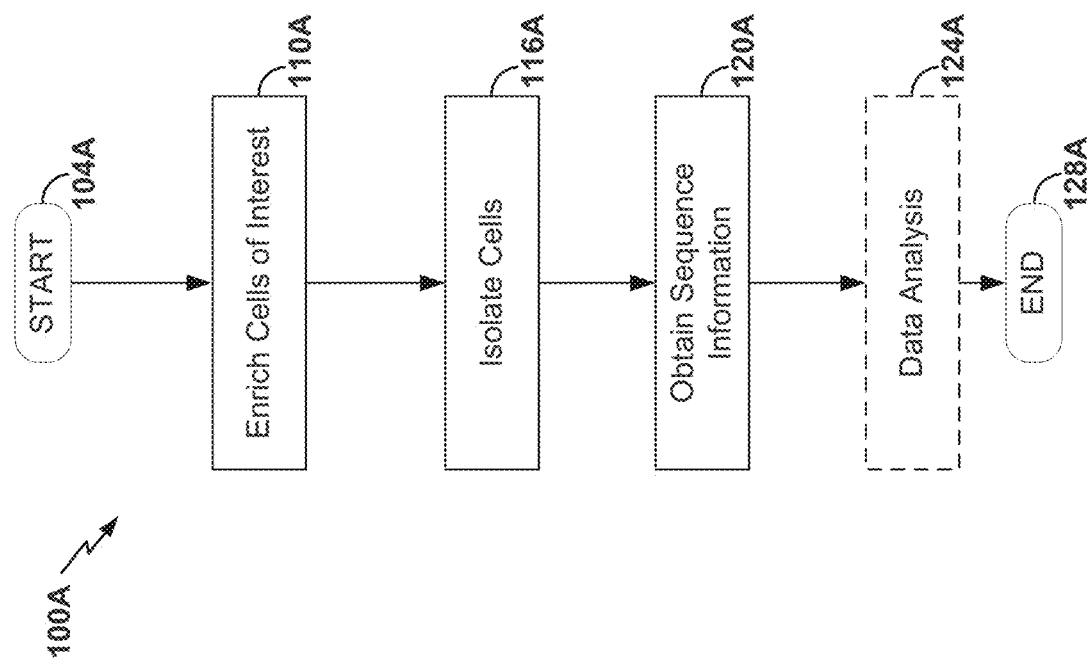

FIG. 1A is a flowchart showing a non-limiting exemplary process 100A combining, the steps of cell enrichment, cell sorting, and obtaining sequence information for the analysis of a sample. The method begins at 104A. At 110A, the method can enrich cells of interest in the sample by, for example, magnetically removing cells not of interest, interfering cells, and debris and acoustically focusing cells of interest in the sample. At 116A, cells of interest are isolated from the enriched cell sample. The isolation can be carried out by, for example, cell sorting including single-cell sorting. The sequence information of the isolated cells can be obtained at 120A by, for example, molecular indexing and sequencing such as NGS. Sequence information from step 120A can optionally be analyzed at 124A before the method completes at 128A. In the method, one or more of the enrichment step 110A and cell sorting step 116A can utilize focusing techniques. Non-limiting examples of focusing techniques include, but are not limited to acoustic focusing, hydrodynamic focusing, magnetic field focusing, electric field focusing, gravitational field focusing, optical field focusing, and any combinations thereof. In some embodiments, the enrichment step 110A can utilize techniques that magnetically deplete interfering cells and debris.

FIG. 1B is a flowchart showing a non-limiting exemplary process 100B from cell enrichment and sorting, molecular indexing, library preparation, sequencing, and data analysis. The process begins at 104B. One or more inline enrichment systems can, for example, magnetically remove cells not of interest, interfering cells, and debris from a sample at 108B. An inline enrichment system can utilize the BD Imag™ magnetic separation beads that bind cells not of interest. Cells can be acoustically focused at 112B to increase the concentration of cells of interest prior to cell sorting at 116B. Cells of interest in the sample can be stained for sorting at 116B using a cell sorter. Examples of cell sorters include, but are not limited to, BD FACSJazz™ cell sorter, a BD FACSseq™ cell sorter, a Bio-Rad Laboratories, Inc. (Hercules, Calif.) S3e™ Cell Sorter, a Sony Biotechnology Inc. (San Jose, Calif.) SH800 cell sorter, a Beckman Coulter Inc. (Brea, Calif.) MoFlo™ XDP cell sorter. After sorting cells at 116B, cells can be lysed for molecular indexing and library preparation at 120B and sequencing at 122B. Sequence information from step 122B can be optionally analyzed at 124B before the method completes at 128B.

In some embodiments, it can be advantageous to have an enrichment step in the method disclosed herein because the step can allow cell sorting to proceed more rapidly with less interference by cells not of interest, interfering cells, and debris. In some embodiments, utilizing acoustic focusing prior to cell sorting enables effective and fast enrichment of cells of interest. This can provide for a reduction of sorting time, for example from hours to minutes and seconds. As would be appreciated by persons of skill in the art, rapid sorting methods can prevent deterioration of cell health, changes in physiological conditions and states of cells, and/or cell death due to long processing time. In some embodiments, populations of live cells can be analyzed at the same point in their life cycles or in their normal physiological conditions and states.

Molecular Indexing and Library Generation

The single-cell sequencing methods disclosed herein can include obtaining sequence information by molecularly indexing the targets from one or more of the isolated cells from the sample. The targets can, for example, be polynucleotides. The polynucleotides can be, for example, DNA or RNA (e.g., mRNA). Molecular indexing (sometimes referred to as molecular barcoding or molecular tagging) can be used, for example, for high-sensitivity single molecular counting. For example, a collection of identical polynucleotide molecules from one or more of the isolated cells can be attached to a diverse set of labels for molecular indexing. Each of the labels can comprise, for example, a molecular label (also known as molecular index). In some embodiments, the method comprises molecularly indexing the polynucleotides from 1, 5, 10, 15, 20, 25, 50, 75, 100, 200, 300, 400, 500, 600, 800, 1000, 2000, 5000, 10000 cells, or a number or a range between any two of these values.

Molecular indexing can, for example, be used to identify the origin of an indexed polynucleotide (e.g., indicating from which tissue, cell and/or container the indexed polynucleotide is from) and/or to inform the identity of the indexed polynucleotide. The container can be a plate, a well, a droplet, a partition, a tube, or like. The indexed polynucleotide can comprise, for example, the polynucleotide to be indexed (e.g., an mRNA, a genomic DNA, or a cDNA) and a label region comprising one or more labels. In some embodiments, the indexed polynucleotide can further comprise one or more of a universal PCR region and an adaptor region. As an example, the indexed polynucleotide can be situated in a container (e.g., a microtiter plate), and the indexed polynucleotide can further include a unique label (e.g., a sample barcode) for identifying the plate in which the index polynucleotide is situated. An example of the region for identifying the plate is a plate index. The label region can, in some embodiments, comprise two or more labels. For example, the label region can include a molecular label (also known as a molecular index) and a sample label (also known as a sample barcode). The length of the labels can vary. For example, the label (e.g., the molecular label or the sample label) can be, or be about, 1, 2, 3, 4, 5, 6, 7, 8, 9, 10, 12, 15, 20 nucleotides in length, or longer. In some embodiments, the molecular label is, or is about, 5 nucleotides in length, and the sample label is, or is about, 5 nucleotides in length. In some embodiments, the molecular label is, or is about, 10 nucleotides in length, and the sample label is, or is about, 10 nucleotides in length.

In some embodiments, molecularly indexing the polynucleotides comprises generating a molecularly indexed polynucleotide library from one or more of the isolated cells. Generating a molecularly indexed polynucleotide library includes generating a plurality of indexed polynucleotides from the one or more of the isolated cells. For example, for a molecularly indexed polynucleotide library comprising a first indexed polynucleotide and a second indexed polynucleotide, the label region of the first indexed polynucleotide can differ from the label region of the second indexed polynucleotide by at least one, two, three, four, or five nucleotides. In some embodiments, generating a molecularly indexed polynucleotide library includes contacting a plurality of mRNA molecules with a plurality of oligonucleotides including a poly(T) region and a label region; and conducting a first strand synthesis using a reverse transcriptase to produce single-strand labeled cDNA molecules each comprising a cDNA region and a label region, wherein the plurality of mRNA molecules includes at least two mRNA molecules of different sequences and the plurality of oligonucleotides includes at least two oligonucleotides of different sequences. Generating a molecularly indexed polynucleotide library can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Molecular indexing uses nucleic acid barcodes or tags to label individual DNA or RNA molecules. In some embodiments, it involves adding DNA barcodes or tags to cDNA molecules as they are generated from mRNA. Nested PCR can be performed to minimize PCR amplification bias. Adaptors can be added for sequencing using, for example, NGS.

Figure 2:
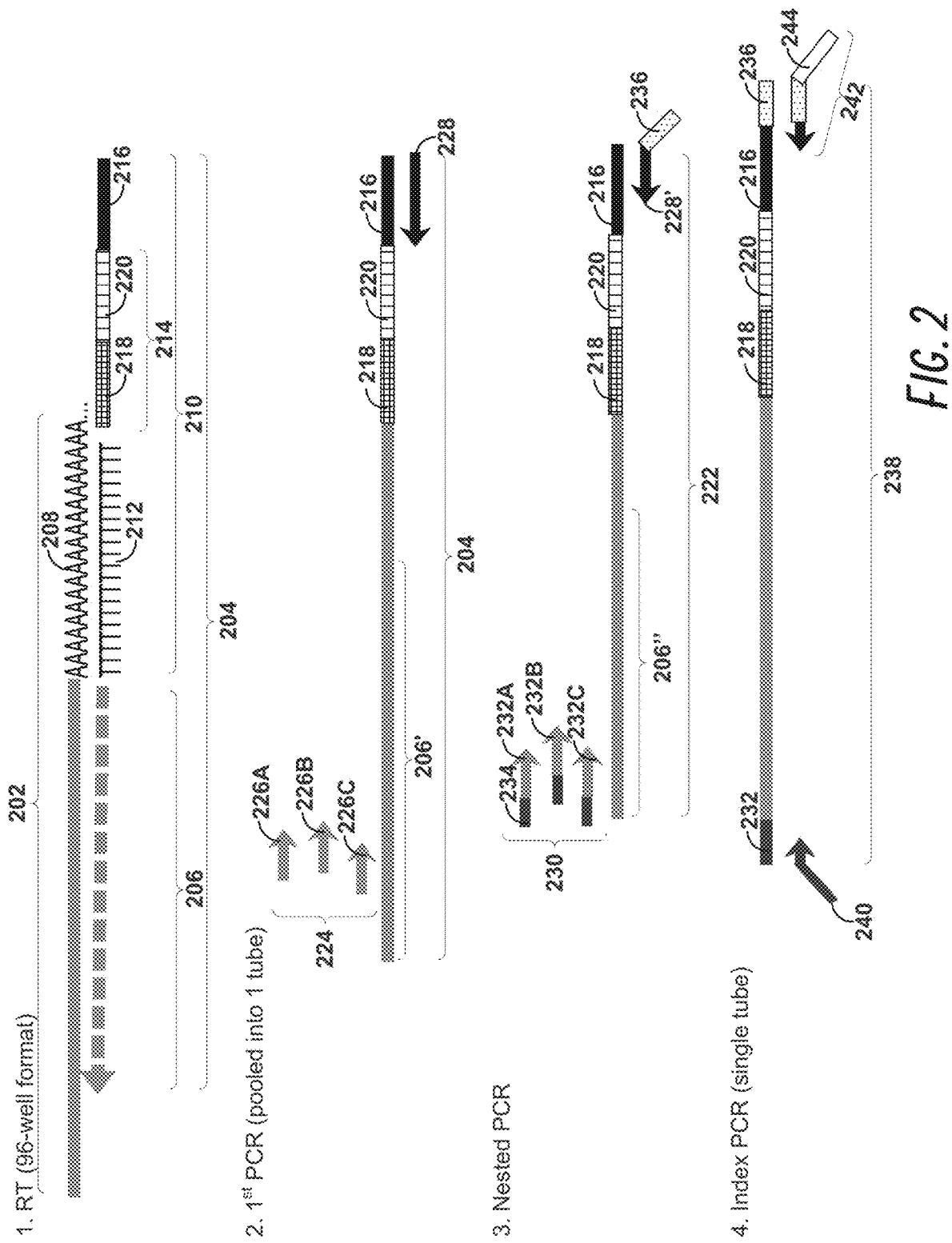
FIG. 2 is a non-limiting schematic illustration showing a non-limiting exemplary process for generating a molecularly indexed polynucleotide library from one or more cells.

FIG. 2 is a schematic illustration showing a non-limiting exemplary process of generating a molecularly indexed polynucleotide library from one or more cells. As shown in step 1, the reverse transcription process can encode each mRNA molecule with a unique molecular label, a sample label, and a universal PCR site. Molecular labels are also known as molecular barcodes and molecular indices. Sample labels are also known as sample barcodes and sample indices. The labels enable all samples in one or more multitier plates in, for example, 96-well format to be pooled together for subsequent steps. In particular, RNA molecules 202 can be reverse transcribed to produce labeled cDNA molecules 204, including a cDNA, by the stochastic hybridization of a set of molecular identifier labels 210 to the poly(A) tail region 208 of the RNA molecules 202. Each of the molecular identifier labels 210 can comprise a poly(dT) region 212, a label region 214, and a universal PCR region 216. In some embodiments, the label region 214 can comprise a molecular label 218 and a sample label 220. The molecular label 218 can be 1, 2, 3, 4, 5, 6, 7, 8, 9, 10, 20, 30, 40, 50, 60, 70, 80, 90, 100, or a number or a range between any of these values, of nucleotides in length. The sample label 220 can be 1, 2, 3, 4, 5, 6, 7, 8, 9, 10, 20, 30, 40, 50, 60, 70, 80, 90, 100, or a number or a range between any of these values, of nucleotides in length. In some embodiments, the label region 214 can comprise 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a molecular label 218 and a sample label 220. Each label can be 1, 2, 3, 4, 5, 6, 7, 8, 9, 10, 20, 30, 40, 50, 60, 70, 80, 90, 100, or a number or a range between any of these values, of nucleotides in length. A set of molecular identifier labels 210 can contain 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or range between any of these values, molecular identifier labels 210. And the set of molecular identifier labels 210 can, for example, each contain a unique label region 214. The labeled cDNA molecules 204 can be purified to remove excess molecular identifier labels 210. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 214. In particular, the labeled cDNA molecules 204 can be amplified to produce nested PCR labeled amplicons 222. Amplification can comprise multiplex PCR amplification. Amplification can comprise a multiplex PCR amplification with 96 multiplex primers in a single reaction volume. In some embodiments, multiplex PCR amplification can utilize 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, between any of these values, multiplex primers in a single reaction volume. Amplification can comprise $1^{st}$ PCR primer pool 224 of custom primers 226A-C targeting specific genes and a universal primer 228. The custom primers 226 can hybridize to a region within the cDNA portion 206' of the labeled cDNA molecule 204. The universal primer 228 can hybridize to the universal PCR region 216 of the labeled cDNA molecule 204.

As shown in step 3, products from PCR amplification in step 2 can be amplified with a nested PCR primers pool and a $2^{nd}$ universal PCR primer. Nested PCR can minimize PCR amplification bias. In particular, the nested PCR labeled amplicons 222 can be further amplified by nested PCR. The nested PCR can comprise multiplex PCR with nested PCR primers pool 230 of nested PCR primers 232A-C and a $2^{nd}$ universal PCR primer 228' in a single reaction volume. The nested PCR primer pool 228 can contain 1, 2, 3, 4, 5, 6, 7, 8, 9, 10, 20, 30, 40, 50, 60, 70, 80, 90, 100, 200, 300, 400, 500, 600, 700, 800, 900, 1000, or a number or range between any of these values, different nested PCR primers 230. The nested PCR primers 232 can contain an adaptor 234 and hybridize to a region within the cDNA portion 206" of the labeled amplicon 222. The universal primer 228' can contain an adaptor 236 and hybridize to the universal PCR region 216 of the labeled amplicon 222. Thus, step 3 produces adaptor-labeled amplicon 238. In some embodiments, nested PCR primers 232 and the $2^{nd}$ universal PCR primer 228' cannot contain the adaptors 234 and 236. The adaptors 234 and 236 can instead be ligated to the products of nested PCR to produce adaptor-labeled amplicon 238.

As shown in step 4, PCR products from step 3 can be PCR amplified for sequencing using library amplification primers. In particular, the adaptors 234 and 236 can be used to conduct one or more additional assays on the adaptor-labeled amplicon 238. The adaptors 234 and 236 can be hybridized to primers 240 and 242. The one or more primers 240 and 242 can be PCR amplification primers. The one or more primers 240 and 242 can be sequencing primers. The one or more adaptors 234 and 236 can be used for further amplification of the adaptor-labeled amplicons 238. The one or more adaptors 234 and 236 can be used for sequencing the adaptor-labeled amplicon 238. The primer 242 can contain a plate index 244 so that amplicons generated using the same set of molecular identifier labels 208 can be sequenced in one sequencing reaction using NGS.

In the methods disclosed herein, stochastic barcoding can be used for molecular indexing. Methods and techniques for stochastic barcoding have been described, for example, in U.S. Patent Pub. No. 20150299784, U.S. Pat. No. 8,835,358, and Fu et al., PNAS, 2001 108(22):9026-9031, the content of which is incorporated herein by reference in its entirety. Non-limiting exemplary methods for performing single molecule digital counting by the stochastic labeling of a collection of identical molecules are illustrated in FIGS. 3 and 4A-B.

Figure 3:
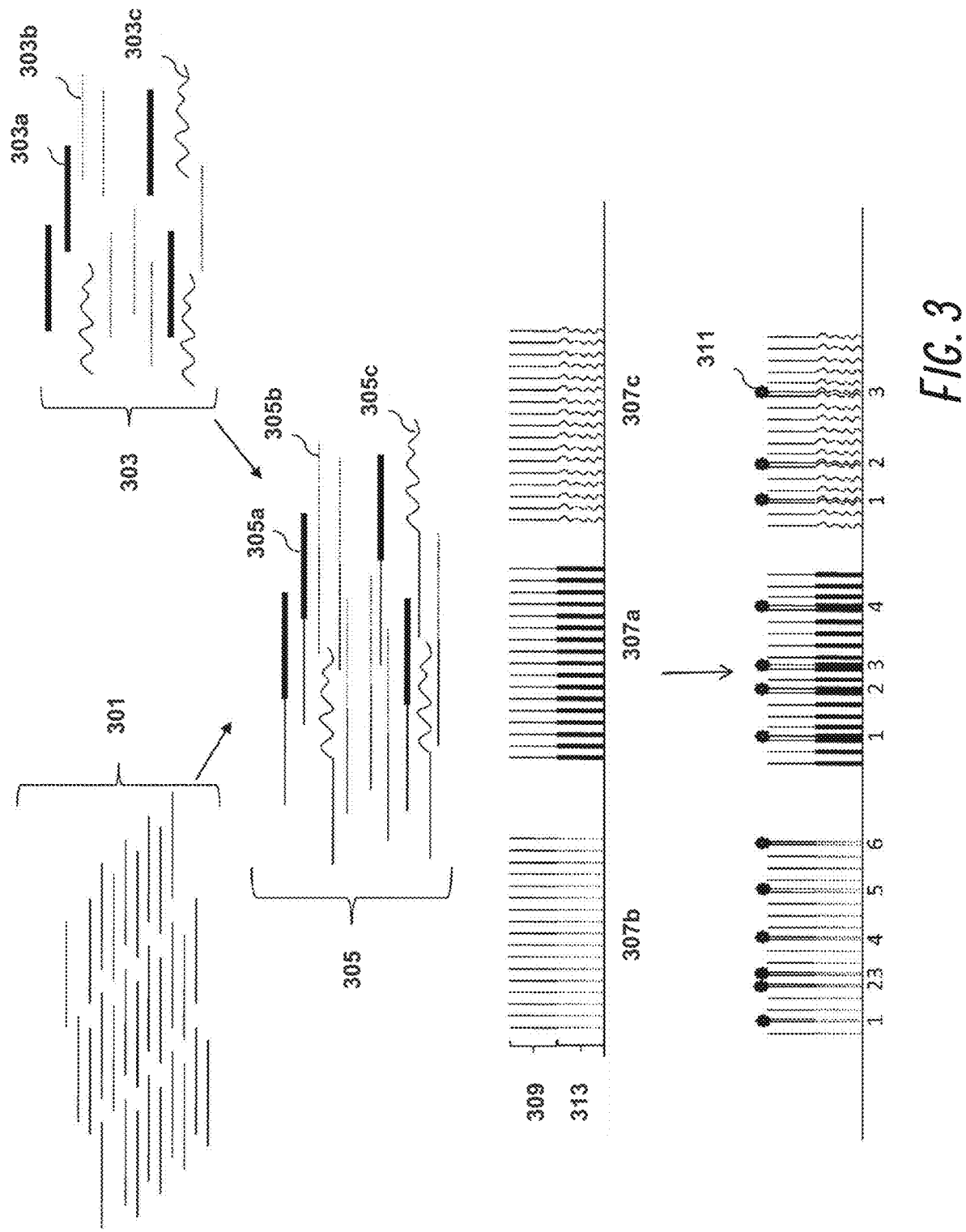
FIG. 3 is a schematic illustration of a non-limiting embodiment of stochastic labeling and counting by hybridization to an array of support bound probes.
Figure 4A:
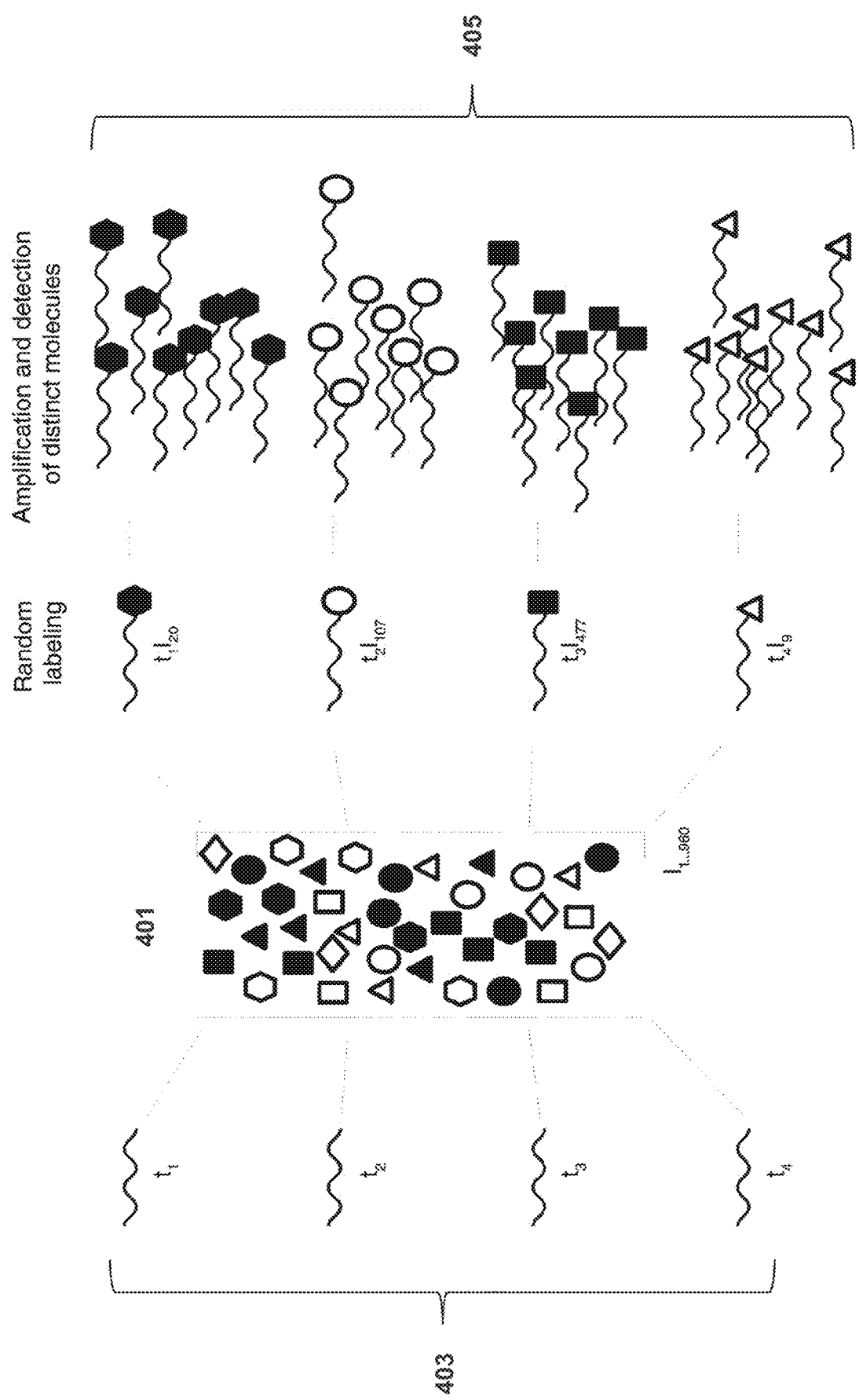
FIGS. 4A-B are non-limiting schematic illustrations of labeling target molecules and detection of labeled targets.
Figure 4B:
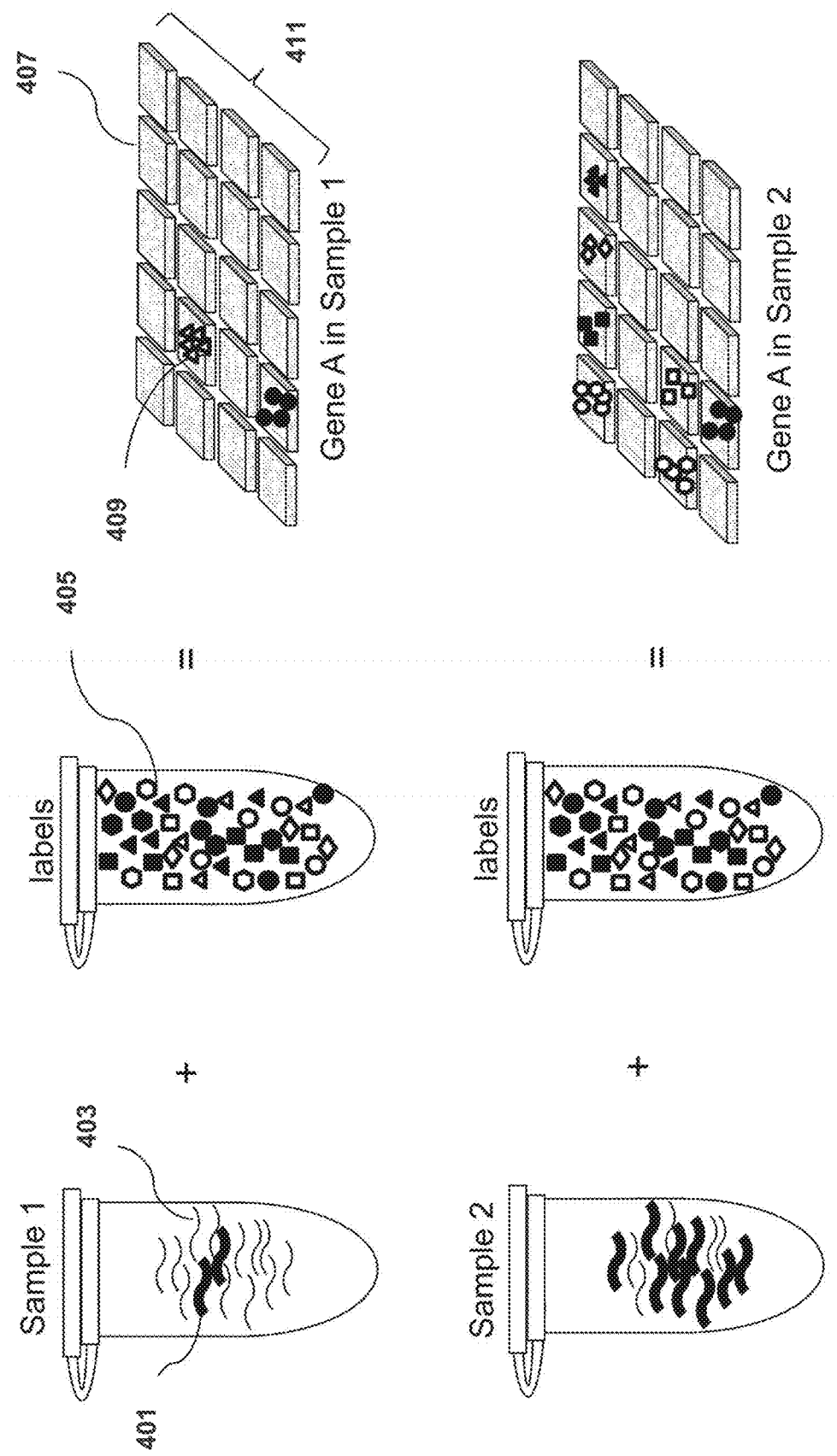

Some embodiments of stochastic barcoding are illustrated schematically in FIG. 3. The library of different label-tag sequences 301 is combined with a sample that includes an unknown number of targets of interest 303. Three different species of target are shown, 303a, 303b and 303c, present at 4, 6 and 3 copies respectively. The individual label-tag oligonucleotides from library 301 are covalently attached to the different targets to form target-label-tag molecules 305. Each target has a collection of different label-tag molecules 305a, 305b and 305c and within each target-specific collection the members differ in the label-tag oligo that is attached. On the array 307, each target is tiled in combination with all possible label-tag combinations represented with each different combination being present at a different known or determinable location on the array. In the figure each different possible combination of target and label-tag is represented by a single probe for illustration purposes, but on the array each different probe is preferably present in a feature having multiple copies of the same probe sequence. The array is divided into subarrays 307a, 307b and 307c for illustrative purposes. The upper portion 309 of the probes varies at each feature according to the different label-tag. The lower portion 313 is the same for all features of each subarray and is complementary to the target. After hybridization individual features of the array are labeled through hybridization of the complementary target-label-tag molecule to the feature. The figure shows a detectable label 311 may be used to detect features where a target-label-tag is hybridized.

Labels or counters 301 are combined with assay targets 303 so that each target is combined with one label to form label-targets 305. The process of combining an individual target with individual label molecules is a stochastic process. The number of labels each target type combines with is directly proportional to the number of individual targets of that target type or the copy number of the target. The number of labels is counted by hybridization to arrays where individual label-targets are detected at different features.

Each copy of a molecule (from a collection of identical target molecules 303) randomly captures a label by choosing from a large, non-depleting reservoir of diverse labels 301. The uniqueness of each labeled molecule is governed by the statistics of random choice, and depends on the number of copies of identical molecules in the collection compared to the diversity of labels. Once the molecules are labeled each has been given a unique identity and can now be separately detected. In some embodiments, it is preferable to first amplify the labeled targets prior to detection so that simple present/absent threshold detection methods can be used. Counting the number of labels is used to determine the original number of molecules in solution. In some embodiments, the molecules to be counted are each members of a class that shares some common feature, for example, they may each be a single copy of a particular gene sequence or nucleic acid sequence. Counting may be applied, for example, to mRNA targets, splice products, alternatively spliced products, structural RNAs, tRNA, miRNA, siRNA, microRNA and the like. Similarly, counting may be applied to DNA, for example, gene copy number, chromosome number, mitochondrial DNA, bacterial genomes, pathogen nucleic acid, viral nucleic acids and the like. Counting may be applied in research of disease in humans or other mammals or agricultural organisms, e.g. cattle, chicken, wheat, rice, fish, etc. Counting may also be applied to counting aspects of microbes, such as environmental measurements, e.g. water quality testing. The methods may be particularly useful where small numbers of items are to be counted and an accurate count is desirable rather than a relative estimate.

The targets are mixed with a collection of label-tag sequences, each label-tag being a different sequence and the collection having a number that is preferably 10 times the number of copies of the most abundant target to be counted. In some embodiments, the label-tags are a collection of known sequences such as a collection of all possible timers ($N_6$). Each of the label-tag sequences is present in multiple copies in the mixture, but all are present at approximately equal amounts. The label-tag sequences are ligated to the targets. Ligation is random so that any given label-tag has about the same probability of ligating to any one target occurrence. So if there are 1000 different targets each could be ligated to a different label-tag sequence and the probability that any two target occurrences will have the same label-tag ligated is low. Because the ligation is a random stochastic process there is a known probability that if there are C copies of a given target and N different label-tags that any two copies of a target T will have the same label.

T1, T2, . . . TN, C1, C2, . . . CX, L1, L2, . . . LY where T are the different targets and there are N different targets, C are the different copies of a target and there are X copies of that target and L are the different label label-tags and there are Y label tags. X varies for each target and determining X is one of the objects of the present invention. The relationship between X and Y determines the probability that two C's will have the same L. In some embodiments, Y is greater than X for each target to be counted. This reduces the probability of undercounting due to double labeling. If C1 and C2 of T1 are both labeled with L3 both copies will be counted as a single occurrence, resulting in under counting. Undercounting can also be adjusted for by estimating the number of copies that are likely to be multiply labeled and adjusting the final count upwards to take those into account. For example, if there is a likelihood that 5 of 1000 copies will be labeled with the same label tag then the final number should be adjusted up by 0.5%.

In some embodiments, the detection is by hybridization to an array of probes. The array has a collection of features for each target that includes a different feature for each label tag. For example, if there are X label tags there are X features for each target, T1L1, T1L2, . . . T1LX and the same for target 2, T2L1, T2L2, . . . T2LX, out to TNL1, TNL2, . . . TNLX. The number of features of the array is on the order of X times N. Each probe has a target complementary sequence and a label tag complementary sequence. Within a set of probes for a given target the target segment of the probe would remain constant and the label tag portion varies from feature to feature so that each label tag sequence is represented by at least one feature for each target.

In some embodiments, the methods may be used to count the number of copies of each of a plurality of targets in a sample. The amount of target containing sample mixed with the label tags may be diluted so that the number of copies of each target to be counted is less than the number of label tags. For example, if the targets to be counted are present at about 1000 copies per cell and there are 10000 label tags you want to have the amount of sample in the mixture to be about the equivalent of one cell's worth of RNA. You can mix that with multiple copies of each label-tag, but you want to keep the absolute number of copies of target below the number of types of label tag sequences. Dilution of the sample and use of an appropriately small amount of starting material may be used. If a target sequence is present at low copy number per cell it is possible to use the nucleic acid from a larger number of cells. For example, to measure the DNA copy number of a chromosomal region relative to other chromosomal regions the expected copy number is low (e.g. 2 for normal) so if there are 10000 different label tags, the number of genomes that can be added to the sample for attachment of label tags can be high, e.g. 500 to 1000.

In some embodiments, the methods are used to identify regions of genomic amplification and chromosomal abnormalities. For example, the methods may be used to detect trisomy. Most of the chromosomal regions will be present in 2 copies per cell and the region of trisomy will be present in 3 copies per cell. You would expect to observe a 3:2 ratio in your count. For example, if you have 500 genomes you would have 1000 copies of most regions and 1500 copies of the trisomy regions. Small errors in the counting, resulting from undercounting, would have little or no effect on the counting. In some embodiments, controls of known copy number may be spiked in to a sample to determine accuracy.

Stochastic labeling of $t_{1,N}$ (collection of essential identical molecules of copy 1, 2 ... N of target 1) by $L_{1,m}$ (effectively an infinite reservoir of diversity m when m is much greater than N). This allows for complete or near complete resolution of members of $t_{1,N}$ by imparting separate identities to the members of the collection of $t_{1,N}$ (provided that m is sufficiently smaller than N in the labeling). This provides for a stochastic or random projection of $t_{1,N}$ onto $L_{1,m}$. In some embodiments $L_{1,m}$ is a library and the members of the library that are associated with $t_{1,N}$ can be counted to determine the number of copies of the target. In some embodiments the methods can be described as indexing the members of the target. This provides a method to follow individual molecules that are members of a type of molecule that would not otherwise be distinguishable one from another.

Because stochastic labeling can impart identifiability to otherwise non-identifiable molecules it can impart identifiability to any two targets that may be very similar, but different. Examples of targets that may be highly similar but could be separately counted using the disclosed methods, include, for example, alternative splice forms of a gene, and sequences that have one or more variations, including a variation in a single base (e.g. SNP or indels (insertion or deletions of short regions, e.g. 1-5 bases). In some embodiments the methods impart a clonal labeling, that allows a single copy to be separately detected and separately isolated from the solution.

Some nucleic acid sequencing reactions use methods that stochastically attach targets to a solid support followed by amplification of the attached target and analysis. The target attaches in an unknown location and the location can be determined by sequencing the amplified target at specific locations. In contrast, the disclosed methods provide for clonal amplification of known targets in a known location. The stochastic nature of the formation of the target-label-tag molecule provides a mechanism for isolating single occurrences of selected targets that can be subsequently amplified and analyzed. In some embodiments the label can be used as a handle for isolating clonal populations of targets. The labeling step generates an indexed library that has a variety of applications. For example, the indexed library could be used for sequencing applications. The method adds distinguishability to any set of molecules, even molecules that are not distinguishable by other mechanisms because they may share common regions or even been identical. The indexed library can be stored and used multiple times to generate samples for analysis. Some applications include, for example, genotyping polymorphisms, studying RNA processing, and selecting clonal representatives to do sequencing.

The methods may be used to convert an analog readout of hybridization signal intensities on arrays into a measurable process that can be scored digitally on the arrays. The method leverages a random process where the tagging of assayed molecules is governed by stochastic behavior. In a random process, the more copies of a given target, the greater the probability of being tagged with multiple labels. A count of the number of incorporated labels for each target can approximate the abundance level of a given target of interest. The ability to count labels on microarrays would be a clear cost-advantage over the other existing techniques.

A stochastic counting assay system as described herein can also be a sub-system within a much larger bio-analysis system. The bio-analysis system could include all the aspects of sample preparation prior to, for example, optical detection, the post processing of data collected in the optical detection phase and finally decision making based on these results. Sample preparation may include steps such as: extraction of the sample from the tested subject (human, animal, plant environment etc.); separation of different parts of the sample to achieve higher concentration and purity of the molecules under investigation; sample amplification (e.g. through PCR); attachment of fluorescence tags or markers to different parts of the sample; and transfer of the sample or a portion of the sample into a reaction vessel or site on a substrate. The post processing of the collected data may include: normalization; background and noise reduction; and statistical analysis such as averaging over repeated tests or correlation between different tests. The decision making may include: testing against a predefined set of rules and comparison to information stored in external data-bases.

The applications and uses of the stochastic labeling and counting methods and systems described herein can produce one or more result useful to diagnose a disease state of an individual, for example, a patient. In some embodiments, a method of diagnosing a disease comprises reviewing or analyzing data relating to the presence and/or the concentration level of a target in a sample. A conclusion based review or analysis of the data can be provided to a patient, a health care provider or a health care manager. In some embodiments the conclusion is based on the review or analysis of data regarding a disease diagnosis. It is envisioned that in another embodiment that providing a conclusion to a patient, a health care provider or a health care manager includes transmission of the data over a network.

Applications for the disclosed methods include diagnosing a cancerous condition or diagnosing viral, bacterial, and other pathological or non-pathological infections. Additional applications of the disclosed methods and systems include, pathogens detection and classification; chemical/biological warfare real-time detection; chemical concentration control; dangerous substance (e.g., gas, liquid) detection and alarm; sugar and insulin levels detection in diabetic patients; pregnancy testing; detection of viral and bacterial infectious diseases (e.g. AIDS, Bird Flu, SARS, West Nile virus); environmental pollution monitoring (e.g., water, air); and quality control in food processing.

Any available mechanism for detection of the labels may be used. While many of the embodiments discussed above use an array readout form, it will be obvious to one of skill in the art that other methods for readout may be used. For example, sequencing may be used for detection of the labels in some embodiments.

In some embodiments the readout is on an array. The array may be a solid support having immobilized nucleic acid probes attached to the surface in an ordered arrangement. The probes may be, for example, synthesized in situ on the support in known locations using photolithography or the probes may be spotted onto the support in an array format. As discussed above, in some embodiments the array includes a probe feature for each possible label-target combination. A feature preferably includes many copies of a single probe sequence. The feature may also have some probes that are not full length, resulting from truncation of synthesis. The photo activation process may not be 100% efficient so some probes are terminated at each step without having subsequent bases added. These truncated probes have the sequence of a portion of the full length probe.

Sequencing readout. After attachment of the labels to the targets in a stochastic manner, the targets may be amplified according to any of the methods disclosed herein and the amplification product may be subjected to any available sequencing method.

A number of alternative sequencing techniques have been developed and many are available commercially. These include the use of microarrays of genetic material that can be manipulated so as to permit parallel detection of the ordering of nucleotides in a multitude of fragments of genetic material. The arrays typically include many sites formed or disposed on a substrate. Additional materials, typically single nucleotides or strands of nucleotides (oligonucleotides) are introduced and permitted or encouraged to bind to the template of genetic material to be sequenced, thereby selectively marking the template in a sequence dependent manner. Sequence information may then be gathered by imaging the sites. In certain current techniques, for example, each nucleotide type is tagged with a fluorescent tag or dye that permits analysis of the nucleotide attached at a particular site to be determined by analysis of image data.

In some embodiments, mass spectrometry analysis may be used to detect the labels and count the targets. The labels can be distinguishable based on size or other property that can be detected. Many of the examples provided herein identify the label based on unique nucleic acid sequence but any distinguishable label may be used, for example, the pool of labels may be labels that are differentially detectable based on fluorescence emission at a unique wavelength.

FIG. 4A illustrates the attachment of different labels from the pool 301 to each of 4 different copies of the same target "t." Label 20 is attached to t1, label 107 to t2, label 477 to t3, and label 9 to t4. The labeled targets are then amplified to generate four unique populations, each population representing a single occurrence of the target in the starting sample.

FIG. 4B illustrates the method for a comparison of two samples, sample 1 and 2. The target 401 Gene A is present in 2 copies in sample 1 and 9 copies in sample 2. Both samples have non-target molecules 403. The labels 405 are combined with the samples and target molecules are attached to individual label-tag molecules in a stochastic manner. The targets with attached label-tags are hybridized to an array 411 having many features, there is a feature for each possible target-label-tag combination. Some of the features are labeled, for example, 409 and others are not, for example, 407. The labeled features indicate the presence of a specific target-label-tag combination and each corresponds to a count. As shown for gene A in sample 1 there are two labeled features so the count is 2. For Gene A in sample 2 there are 9 labeled features so the count is 9.

In some embodiments, the methods disclosed herein can stochastically expand a population of indistinguishable molecules to a population of uniquely identifiable and countable molecules. High-sensitivity threshold detection of single molecules is demonstrated, and the process can be used to count both the absolute and relative number of molecules in a sample. The method should be well suited for determining the absolute number of multiple target molecules in a specified container, for example in high-sensitivity clinical assays, or for determining the number of transcripts in single cells. The approach should also be compatible with other molecular assay systems. For example, antibodies could be stochastically labeled with DNA fragments and those that bind antigen harvested. After amplification, the number of labels detected will reflect the original number of antigens in solutions. In the examples shown here, DNA is used because of the great diversity of sequences available, and because it is easily detectable. In principle, any molecular label could be used, for example fluorescent groups or mass spectroscopy tags, as long as they are easily detected and they have sufficient diversity for the desired application. Although many of the examples refer to populations Methods and compositions for single molecule counting employing the use of stochastic labeling are disclosed herein. In some embodiments, a diverse set of labels is randomly attached to a population of identical molecules is converted into a population of distinct molecules suitable for threshold detection. Random attachment as used herein refers to a process whereby any label can be attached to a given molecule with the same probability. To demonstrate stochastic labeling methods experimentally the absolute and relative number of selected genes were determined after stochastically labeling about 1000, 2000, 3000, 4000, 5000, 6000, 7500, 10000, 20000, 30000, 40000, 50000, 60000, 75000, 100000, 200000, 300000, 400000, 500000, 600000, and 750000 different fragments and more than 1000000 fragments of a genome such as a human genome. The approach does not require the physical separation of molecules and may take advantage of highly parallel methods such as microarray and sequencing technologies to simultaneously count absolute numbers of multiple targets. In some embodiments, stochastic labeling may be used for determining the absolute number of RNA or DNA molecules within single cells.

The methods disclosed herein may be used to take quantitative measurements of copies of identical molecules in a solution by transformation of the information to a digital process for detecting the presence of different labels. The stochastic properties of the method have been measured, and the relative and absolute digital counting of nucleic acid molecules is demonstrated. The method is extremely sensitive, quantitative, and can be multiplexed to high levels. In some embodiments a microarray-based detection method is used, but the method is extendable to many other detection formats.

In some embodiments, the methods are based on probability theory, where the outcome of chemical reactions occurring between a set of labeling molecules and a set of target molecules is modeled and tested. When all of the molecules in a uniform mixture of fixed volume collide and react randomly, the chemical events follow a stochastic process governed in part by the molecule concentration of each species.

Methods for analyzing genomic information often utilize a correlation between a measurement of the amount of material associated with a location. The location can be, for example, a feature of an array that contains a specific sequence that is known or can be determined or any type of solid support such as a bead, particle, membrane, etc. A common aspect to these methods is often hybridization of a target to be measured to a complementary probe attached to the solid support. The probe may be, for example, an oligonucleotide of known or determinable sequence, but may also be BACs, PACs, or PCR amplicons.

Because of the density of different features that can be obtained using synthesis methods such as photolithography, microarrays can be applied to high density applications. For example, at feature sizes of 1 micron square an array can have about $10^8$ features per $cm^2$. Within a feature, depending on the chemistry used for synthesis, the probes are spaced typically at about 10 nm spacing resulting in about $10^4$ moleculesin a $micron^2$. At approximately full saturation about 10% of those probes are hybridized with target. There are then about 640 functional molecules in an array having 1 $micron^2$ spacing between features 0800 $nm^2$ functional area). This relatively small number of functional molecules in a feature limits the dynamic range for estimating relative concentration from hybridization signal intensity.

For example, at feature sizes of 1 micron square an array can have about 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, and $10^{19}$ features and more than $10^{20}$ features per $cm^2$. Within a feature, depending on the chemistry used for synthesis, the probes are spaced at about 0.00001, 0.0001, 0.001, 0.01, 0.1, 0.5, 1, 2, 3, 4, 5, 6, 7, 8, 9, 10, 20, 30, 40, 50, 60, 75 nm spacing and more than 100 nm spacing. There may be about 10, $10^2$, $10^3$, $10^4$, $10^5$, $10^6$, $10^7$, $10^8$, and $10^9$ molecules and more than $10^{10}$ molecules in one $micron^2$.

Methods are disclosed herein to overcome the dynamic range limitations observed with small feature sizes and small numbers of molecules on the array surface, by using a counting or digital readout as a substitute for the typical analog signal resulting from array hybridization.

Methods that use signal intensity to estimate relative concentrations of targets typically label the targets with a detectable label, often after an amplification step, and through hybridization of the labeled target to the probe, the probe and thus the feature is also labeled. The amount of label is detected and correlated with a measurement of the amount of target in the sample. The estimate of amount of a given target in a sample is typically relative to other targets in the sample or to previously obtained measurements and may be based on comparison to targets present in the sample at known or expected levels or to controls within the sample. This type of analysis can and has been used successfully, for example, to estimate genomic copy number to detect copy number variation in individuals or in cell populations.

Correlating intensity of hybridization signal or signal intensity with concentration of target molecules has limitations and can typically provide only an estimate of the absolute amount of a target, and may not be an accurate count of the actual amount of target present. The estimate may be an under or over estimate, particularly when comparing different targets or different samples. This is the result of many different factors, including but not limited to, differences between probes, feature specific effects, sample specific effects, feature size (as it decreases the ability to correlate accurately decreases) and experimental variation. Much of this variation can be addressed by data analysis methods, but the methods do not provide counting of individual molecules or events and are therefore subject to estimation errors.

In some embodiments, methods are disclosed for attaching a different label-tag sequence to each molecule of a particular target sequence or more preferably a collection of target sequences of interest. For example, a sample having 100 molecules of target type 1 is mixed with an excess, for example, 1000 different label-tag sequences, forming a library of label-tag sequences under ligation conditions. Multiple copies of the library of label-tag sequences are added so there are preferably many copies of each label-tag. Different label-tag sequences from the library are appended to each of the 100 target molecules so that each of the 100 molecules of the first target sequence has a unique label-tag sequence appended thereto. This results in 100 different target-label-tag combinations. The target-label-tag molecules may then be amplified to enrich the target-label-tag products relative to other non-targets. Amplification after labeling alters the absolute amount of the target, but because each occurrence in the original sample has been uniquely labeled this will not alter the count. The amplified target-label-tag products, whether amplified or not, can then be labeled with a detectable label, and hybridized to an array of probes. The features of the array that have target-label-tag hybridized thereto can be detected, for example, by labeling the hybridization complex with a fluorescent label and detecting the presence of signal at the features. In this example, because there are 1000 different labels possible and a single target being analyzed, there are 1000 different possible label-target sequences that might be generated so an array having a different feature for each of the 1000 different possibilities can be used. Assuming each target is labeled and no label is used twice, 100 of the 1000 different features should be detectable, indicating the corresponding label has been used.

Once the target molecules are labeled with the counter they can be amplified freely without impacting the counting since the readout is either yes, indicating detection or no indication not detected. In some embodiments, a simple detector having m elements for each target sequence can be constructed. The detector may be an array. An array having $10^8$ features or elements could assay $10^5$ different targets using $10^3$ different labels, for example. Other detection methods do not require individual elements for each counter, for example, sequencing.

In some embodiments, the "counter library" or "label-tag library" has approximately the same number of copies of each label-tag in the library. The label-tag sequences are not target specific, but are like the tags that have been used for other tagging applications, for example, the Affymetrix GENFLEX tag array. Possibly all label-tags in a set of label-tags will have similar hybridization characteristics so that the label-tags of the set can be detected under similar conditions.

For each target there are a series of features on the array, preferably one feature for each label-tag. In each of these features the portion of the probe that hybridizes to the target (or target complement) is the same but the label-tag complement is different in each feature. For example, to detect a first target RNA, "RNA1," there would be a series of features each having a different probe (RNA1-tag1, RNA1-tag2, . . . RNA1-tagN). For each target to be detected there is a similar set of features, e.g. RNA2-tag1, RNA2-tag2, . . . RNA2-tagN. The set of label-tags is N tags and it is the unique combination of the label-tag with the target sequence that creates a novel sequence to be detected, for example, by hybridization.

Label-tag attachment to individual targets is a stochastic process whereby the probability of any given label-tag being attached to any target is stochastic. There is a random selection of label-tags by attaching the label-tags to the end of a known target sequence in a sequence independent manner. The label-tag is attached without requirement for it to hybridize to any portion of the target so there is no or minimal bias as to which label-tag sequence is attached. Individual molecules all look the same for the purpose of attachment of the label-tag.

The label-tag may be attached to the target by any method available. In some embodiments, the label-tag is attached by ligation of the label-tag to one of the ends of the target. In some embodiments, the probes of the array are complementary to a predicted junction between target and label so it is preferable that the labels are attached to all occurrences of a target at the same position. This is facilitated if the termini of each occurrence of a selected target are the same and are known. In some embodiments, target occurrences are fragmented with a restriction enzyme so that defined ends of known sequence are formed.

After label-tag attachment in some embodiments the target-label-tag segment is amplified. Attachment of universal primers to either end followed by PCR amplification is one method for amplifying. The universal primers may be added along with the label or at a subsequent ligation step.

For RNA targets an RNA ligase, such as T4 RNA ligase may be used. T4 RNA ligase 1 catalyzes the ligation of a 5' phosphryl-terminated nucleic acid donor to a 3' hydroxyl-terminated nucleic acid acceptor. Substrates include single-stranded RNA and DNA. RNA targets may also be circularized and used as template for rolling circle amplification using an enzyme having reverse transcriptase activity. T4 RNA ligase 1 may be used for circularization of RNA by ligating the ends of the molecule together. T4 RNA ligase 1 can also be used to ligate RNA to DNA.

Full-length mRNA can be selected by treating total or poly(A) RNA with calf intestinal phosphatase (CIP) to remove the 5' phosphate from all molecules which contain free 5' phosphates (e.g. ribosomal RNA, fragmented mRNA, tRNA and genomic DNA). Full-length mRNAs are not affected. The RNA can them be treated with tobacco acid pyrophosphatase (TAP) to remove the cap structure from the full-length mRNA leaving a 5'-monophosphate. A synthetic RNA adapter can be ligated to the RNA population. Only molecules containing a 5'-phosphate, (i.e. the uncapped, full-length mRNAs) will ligate to the adapters. Preferably the adapter has a variable label sequence, and may also have a constant sequence for priming. Preferably, the constant sequence is 5' of the variable sequence. In some embodiments, the adapter ligated mRNA may then be copied to form a first strand cDNA by, for example, random priming or priming using oligo dT. The cDNA may subsequently be amplified by, for example, PCR. T4 RNA ligase may also be used for ligation of a DNA oligo to single stranded DNA.

In some embodiments, the ligated target-label-tag molecule may be enriched in the sample relative to other nucleic acids or other molecules. This enrichment may be, for example, by preferentially amplifying the target-label-tag methods, using for example, a DNA or RNA polymerase, or by degrading non target-label-tag molecules preferentially.

In some embodiments, the target-label-tag molecule may be nuclease resistant while the unligated target and unligated label molecules may be nuclease sensitive. A nuclease can be added to the sample after ligation so that ligated target-label-tag molecules are not digested but non-ligated molecules are digested. For example, the targets may be resistant to a 5' exonuclease (but not a 3' exonuclease) while the labels are resistant to a 3' exonuclease but not a 5' exonuclease. Ligating target to label generates a molecule that is resistant to 5' and 3' exonuclease activity. After ligation the sample may be treated with a 5' exonuclease activity, a 3' exonuclease activity or both 5' and 3' exonuclease activities. Exo VII, for example degrades single stranded DNA from both the 5' and 3' ends so the sample could be treated with Exo VII after ligation to degrade molecules that are not ligation products.

In some embodiments, amplification may include a rolling circle amplification (RCA) step. The targets may be ligated so that they have a label and a universal priming (UP) sequence attached to the 5' end of the targets. The UP-label-target is then ligated to form a circle. A primer complementary to the UP is then hybridized to the circles and extended using a strand displacing polymerase. The resulting amplification product contains multiple copies of the complement of the circle, UP-target-L.

In some embodiments, targets may be labeled in a copying step. For example, a primer having a 3' target specific region and a 5' variable label region may be hybridized to the targets, either RNA or DNA, and extended to create a single complimentary copy of the target. Each extension product will have a different label and the junction between the label and the target specific region is known. The extension may be performed in the presence of nuclease resistant nucleotides so that the extension product is resistant to nuclease but the unextended primers are not. After extension the reaction is treated with a 3'-5' exonuclease activity to digest unextended primer. Exonuclease I, for example, removes nucleotides from single stranded DNA in the 3' to 5' direction and Exo III removes nucleotides from the 3' termini of duplex DNA. Exonuclease T (or RNase T) is a single-stranded RNA or DNA specific nuclease that requires a free 3' terminus and removes nucleotides in the 3' to 5' direction. The extension products are then detected by hybridization to probes that are complementary to the primers and include the unique label portion and the constant target specific portion. If the target is RNA it can be digested with RNase H after extension. The extension product may also be amplified before hybridization.

In some embodiments, the probability that any two targets are labeled with the same label may be decreased by using two or more labeling steps. For example, a first labeling step where each target has a label selected from a set of labels followed by a second labeling set using the same set of labels. The first labeling event will be independent of the second so the probability that the first and second labeling events will both be the same in two independent targets is the product of the probability of two targets having the same label in either step. If there are N possible labels, and the first target is labeled first with label N1 and then with label N4, the probability that a second target will be labeled also with N1 and then N4 is $1/N^2$. So if there are 100 different labels, the probability that two targets will be labeled with the same label in the first round and the same label in the second round is $1/10000$.

In some embodiments, a first round of labeling may be done with 16 probes (for example, all possible 2 base combinations) and then a second round of labeling is done using the same 16 probes. The chance of any one probe attaching to a given target occurrence in the first round is 1 out of 16, the chance that the same probe will attach to the second target is $1/16$ and the chance that the same two probes will attach is $1/16 \times 1/16$ or $1/256$.

In some embodiments, reversible terminators are used to add a sequence to the end of each target being counted. For example, a 6 base sequence may be added and the chance of two being the same is 1 in $4^6$ or 1 in 4096.

The methods disclosed herein can be used to measure random cell-to-cell variations in gene expression within an isogenic population of cells. Such variation can lead to transitions between alternative states for individual cells. For example, cell-to-cell variation in the expression of comK in *B. subtilis* has been shown to select cells for transition to the competent state in which genes encoding for DNA uptake proteins are expressed.

Focusing Methods

Methods disclosed herein can, in some embodiments, include enriching a sample comprising a plurality of cells for cells of interest to produce an enriched cell sample, wherein enriching the sample comprises focusing cells of interest in the sample; isolating one or more cells of interest in the enriched cell sample with a flow cytometer; and obtaining sequence information of one or more polynucleotides from each of the one or more isolated cells. Various focusing methods and techniques can be used, for example, hydrodynamic focusing, magnetic field focusing, electric field focusing, gravitational field focusing, optical field focusing, and any combination thereof.

In some embodiments, enriching the sample includes focusing cells of interest in the sample, for example, into a core stream of cells. Focusing cells of interest can, in some embodiments, include acoustic focusing. Acoustic focusing uses acoustic waves to control the movement of particles (e.g., cells) during analysis, for example uses ultrasonic radiation pressure (e.g., >2 MHz) to transport particles into the center of a sample stream. In some embodiments, it is advantageous to combine acoustic focusing and hydrodynamic focusing to narrow core stream and uniform laser illumination. In some embodiments, acoustic focusing includes: suspending the plurality of cells in the sample in an elongated fluid-filled channel; and exposing said channel to an axial acoustic standing wave field parallel to the direction of flow, wherein said axial acoustic standing wave field drives the plurality of cells to positions of force minimum along the center axis of said channel to result in uniformly spaced cells.

Acoustic radiation pressure can manipulate cells. Applying an acoustic wave field generates a quasi-one-dimensional force field that focuses cells, for example, cells of interest. Acoustic focusing, alone or in combination with hydrodynamic focusing, can focus cells into a core stream of cells, for example, at positions of force potential minimum along the center axis of an elongated fluid-filled channel. Acoustic focusing thus increases the concentration of cells within the core stream. After discarding some or all of the fluid not within the core stream, the concentration of cells increases. Thus, acoustic focusing increases sample throughput of dilute samples with low concentration of cells of interest by increasing concentration of cells of interest.

Figure 5:
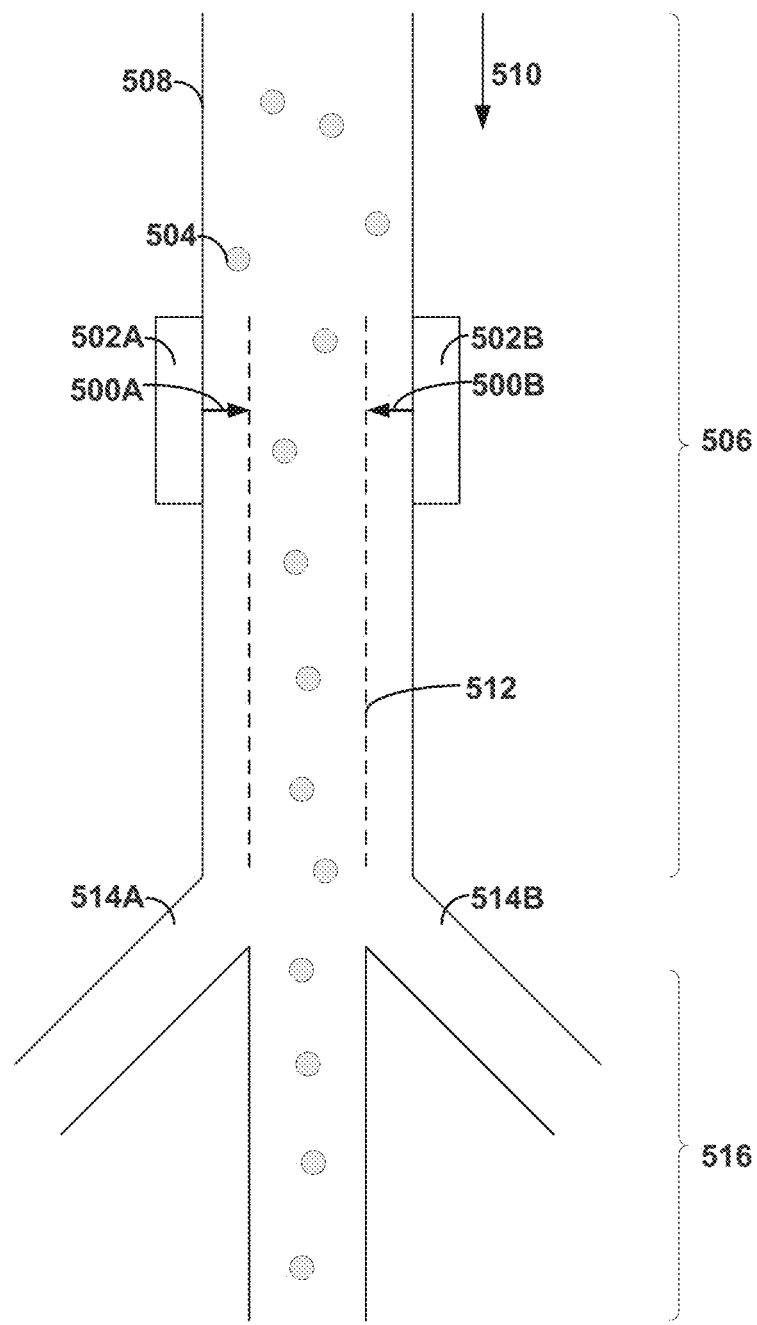
FIG. 5 is a non-limiting schematic illustration of acoustic focusing.
Figure 6A:
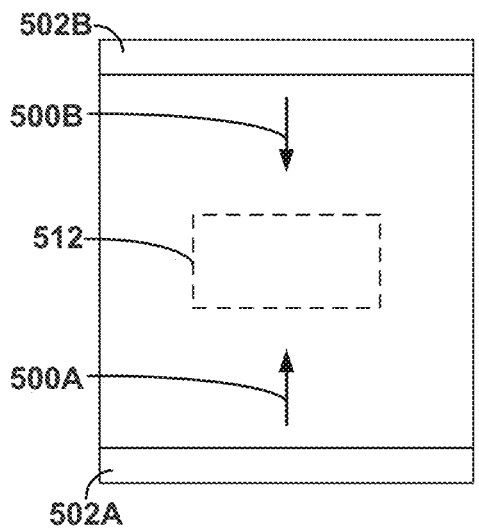
FIGS. 6A-C are non-limiting schematic illustrations of acoustic focusing.

FIGS. 5 and 6A-C illustrate non-limiting embodiments of the present disclosure that focus particles, such as cells of interest in a sample, into a core stream prior to isolating one or more cells of interest. Methods that can be used to focus the particles include acoustic focusing. As shown in FIGS. 5 and 6A, by applying acoustic forces 500A-B generated by an acoustic force generator, such as ultrasonic transducers 502A-B, to cells of interest 504 in a first section 506 of a channel 508, the cells of interest 504 are focused into a core stream 510. The channel 508 can be elongated and fluid-filled.

The cells of interest 504 can be focused into the core stream 510 at positions of force potential minimum along the center axis of the channel to result in uniformly spaced cells. The acoustic forces can comprise an axial acoustic standing wave field parallel to the direction of flow 510 within the channel 508. The ultrasonic transducers 502A-B create a standing wave field in the channel 508. Ultrasonic radiation pressure forces the cells of interest 504 into the core stream 512. After the cells of interest 504 are focused into the core stream 512, some or all of fluid not within the core stream 512 can be discarded through exits 514A-B. So the concentration of cells in the second section 516 of the channel 508 is higher than the concentration of cells in the first section 506 of the channel 508. In some embodiments of the present disclosure, it is advantageous to focus the cells into the core stream 512. In other embodiments of the present disclosure, it is advantageous to focus the cells to positions of force potential minimum in the core stream 510 along the center axis of the channel to result in uniformly spaced cells.

Figure 7:
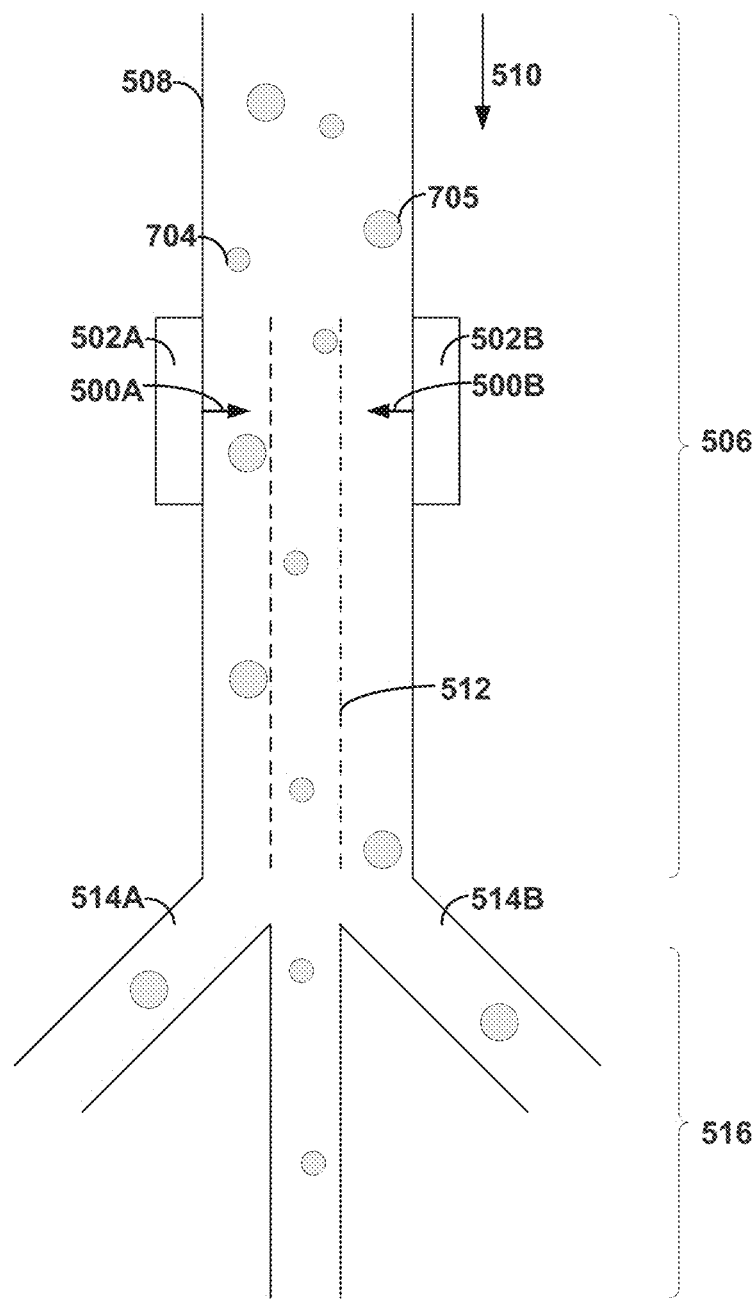
FIG. 7 is a non-limiting schematic illustration of acoustic focusing.

FIG. 7 illustrates embodiments of the present disclosure that focus particles each having a size within a predetermined range in a sample, such as cells of interest each having a size within a predetermined range in a sample, into a core stream prior to isolating one or more cells of interest. Methods that can be used to focus the particles with sizes within a predetermined range include acoustic focusing. As described in connection with FIGS. 5 and 6A, by applying acoustic forces 500A-B generated by an acoustic force generator, such as ultrasonic transducers 502A-B, to the cells of interest each having a size within a predetermined range 704 in a first section 506 of a channel 508, the cells of interest each having a size within a predetermined range 704 are focused into a core stream 510. By adjusting parameters of the acoustic forces 500A-B, for example the frequency, magnitude, and waveform of the acoustic forces 500A-B, only cells of interest each having a size within a predetermined range 704 are focused into the core stream 512. Cells not of interest each having a size not within a predetermined range 705 are not focused into the core stream 512. The channel 508 can be elongated and fluid-filled.

The cells of interest having sizes within a predetermined range 704 can be focused into the core stream 510 at positions of force potential minimum along the center axis of the channel to result in uniformly spaced cells. The acoustic forces can comprise an axial acoustic standing wave field parallel to the direction of flow 510 within the channel 508. The ultrasonic transducers 502A-B create a standing wave field in the channel 508. Ultrasonic radiation pressure forces the cells of interest having sizes within a predetermined range 704 into the core stream 512. After the cells of interest that have certain sizes 704 are focused into the core stream 512, some or all of fluid not within the core stream 512 and cells not of interest having sizes not within a predetermined range 705 can be discarded through exits 514A-B. So the concentration of cells of interest that have sizes within a predetermined range 704 in the second section 516 of the channel 508 is higher than the concentration of cells of interest that have sizes within a predetermined range 704 in the first section 506 of the channel 508. In some embodiments of the present disclosure, it is advantageous to focus the cells of interest that have sizes within a predetermined range 704 into the core stream 512. In other embodiments of the present disclosure, it is advantageous to focus the cells of interest that have sizes within a predetermined range to positions of force potential minimum in the core stream 510 along the center axis of the channel to result in uniformly spaced cells.

Figure 6B:
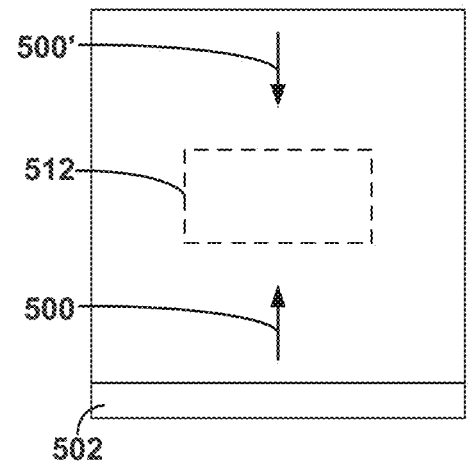
Figure 6C:
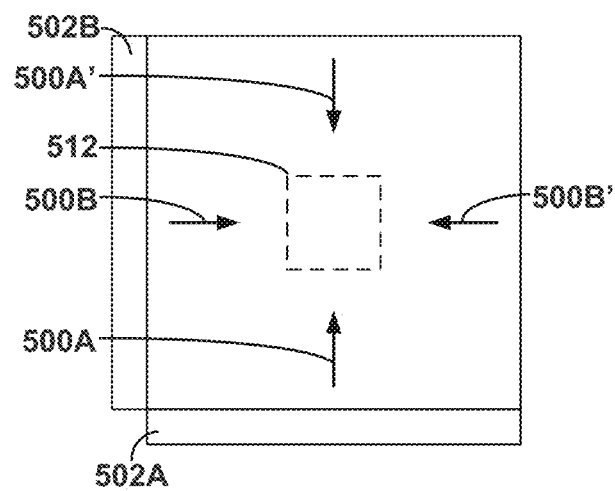

There are many different arrangements where acoustic focusing can be advantageous. Referring to FIGS. 5 and 7, the acoustic field can be used in the channel 508 that can be circular, square, or any other geometry. One exemplary transducer is shown in FIG. 6B. In FIG. 6B, acoustic force 500 is reflected by the wall of the channel 508 shown as acoustic force 500'. Two transducers opposite of each other are shown in FIGS. 5, 6A, and 7. Two transducers orthogonal of each other are shown in FIG. 6C. Acoustic force 500A is reflected by the wall of the channel 508 shown as acoustic force 500A'. Acoustic force 500B is reflected by the wall of the channel 508 shown as acoustic force 500B'. There can be 1, 2, 3, 4, 5, 6, 7, 8, 9, 10, 20, 30, 40, 50, 60, 70, 80, 90, 100, or a number or range between any of these values, transducers 500. Using two transducers opposite of each other can provide feedback to monitor the acoustic field within the elongated fluid-filled channel 506. Additionally transducers can be attached in orthogonal directions to create force fields, for example axial acoustic standing wave fields, that are optimized for focusing cells of different types, sizes, and shapes. In some embodiments, serial acoustic focusing in one or more channels 508 focus the cells of interest 504 into a narrower core stream 512.

The numbers of exits shown in FIGS. 5 and 7 are two, including exits 514A and 514B. There can be 1, 2, 3, 4, 5, 6, 7, 8, 9, 10, 20, 30, 40, 50, 60, 70, 80, 90, 100, or a number or a range between any of these values, exits. The second section 516 shown in FIGS. 5 and 7 is narrower than the first section 506. In some embodiments, the second section 516 can be wider than the first section 506, or the two sections can have the same size. The two sections 506 and 516 can have the same shape or of different shapes. The two sections 506 and 516 can be made of the same materials or of different materials.

Figure 8:
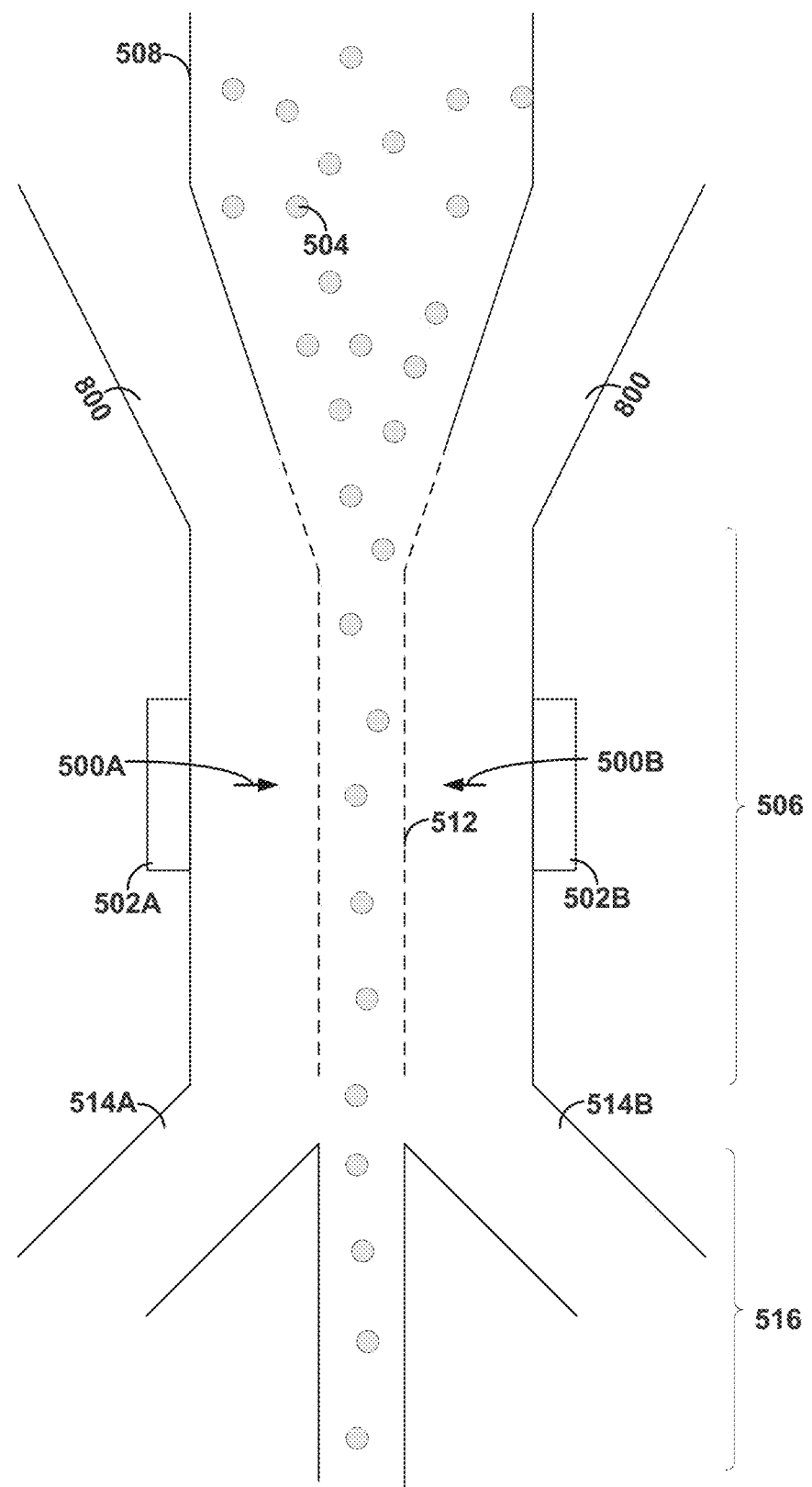
FIG. 8 is a non-limiting schematic illustration of combining acoustic focusing and hydrodynamic focusing.

FIG. 8 illustrates embodiments of the present disclosure capable of combining acoustic focusing and hydrodynamic focusing to concentrate cells according to one embodiment of the present invention. A sample of cells 504 flow through a channel 508 that can be elongated and fluid-field. Sheath fluid 800 hydrodynamically focuses cells 504 to the central core stream 512 initially. Transducers 500A and 500B utilizes acoustic focusing to further focus cells 504 within the central core stream 512. After the cells 504 are focused into the core stream 512 by both hydrodynamic focusing and acoustic focusing, some or all of fluid not within the core stream 512 can be discarded through exits 514A-B. Consequently the concentration of cells in the second section 516 of the channel 508 is higher than the concentration of cells in the first section 506 of the channel 508.

In some embodiments, acoustic focusing, alone or in combination with hydrodynamic focusing, of the cells of interest at 112B increase the concentration of cells of interest by at least 10%, 20%, 30%, 40%, 50%, 60%, 70%, 80%, 90%, $10^2$%, $10^3$%, $10^4$%, $10^5$%, $10^6$%, $10^7$%, $10^8$%, $10^9$%, $10^{10}$%, $10^{11}$% $10^{12}$%, $10^{13}$%, $10^{15}$%, $10^{20}$%, or a number or range between any two of these values. Acoustic focusing, alone or in combination with hydrodynamic focusing, of the cells of interest at 112B increases the speed of sorting at 116B by at least 10-folds, 20-folds, 30-folds, 40-folds, 50-folds, 60-folds, 70-folds, 80-folds, 90-folds, $10^2$-folds, $10^3$-folds, $10^4$-folds, $10^5$-folds, $10^6$-folds, $10^7$-folds, $10^8$-folds, $10^9$-folds, $10^{10}$-folds, $10^{11}$-folds, $10^{12}$-folds, $10^{13}$-folds, $10^{15}$-folds, $10^{20}$-folds, or a number or a range between any two of these values.

Depletion of Cells not of Interest, Interfering Cells and Debris

In some embodiments, enriching the sample includes depleting cells not of interest in the sample. In some embodiments, enriching the sample includes both acoustic focusing and depleting cells not of interest in the sample. In some embodiments, one or more of cells not of interest, interfering cells and debris in the sample can be depleted, for example using magnetic depletion. According to some embodiments, depletion of cells not of interest, interfering cells, and debris (e.g., using magnetic depletion at 108B of FIG. 1B) can remove at least 1%, 2%, 3%, 4%, 5%, 6%, 7%, 8%, 9%, 10%, 20%, 30%, 40%, 50%, 60%, 70%, 80%, 90%, 95%, 99%, 99.5%, 99.9%, or a number or a range between any two of these values, of the cells not of interest, interfering cells, and/or debris originally present in the sample. In some embodiments, at least 10%, 20%, 30%, 40%, 50%, 60%, 70%, 80%, 90%, 91%, 92%, 93%, 94%, 95%, 96%, 97%, 98%, 99%, 99.5%, 99.9%, 99.95%, 99.99%, 99.995%, 99.999%, or a number or a range between any two of these values, of the solid mass in the sample after depletion is the cells of interest. In some embodiments, 10%, 20%, 30%, 40%, 50%, 60%, 70%, 80%, 90%, 91%, 92%, 93%, 94%, 95%, 96%, 97%, 98%, 99%, 99.5%, 99.9%, 99.95%, 99.99%, 99.995%, 99.999%, or a number or a range between any two of these values, of the solid mass in the sample after depletion is the cells of interest. In some embodiments, the concentration of the cell of interest in the sample is increased by at least, or at least about 2-folds, 3-folds, 4-folds, 5-folds, 6-folds, 7-folds, 8-folds, 9-folds, 10-folds, 50-folds, 100-folds, 250-folds, 500-folds, 750-folds, 1000-folds, 5000-folds, 10000-folds, 50000-folds, 100000-folds, 500000-folds, 1000000-folds, or a number or a range between any two of these values, after depletion. In some embodiments, the concentration of the cell of interest in the sample is increased by, or by about, 2-folds, 3-folds, 4-folds, 5-folds, 6-folds, 7-folds, 8-folds, 9-folds, 10-folds, 50-folds, 100-folds, 250-folds, 500-folds, 750-folds, 1000-folds, 5000-folds, 10000-folds, 50000-folds, 100000-folds, 500000-folds, 1000000-folds, or a number or a range between any these two values, after depletion.

Cells of interest can be acoustically focused prior or subsequent to depleting cells not of interest in the sample. In some embodiments, the depletion is carried out by magnetic depletion. Magnetic depletion can, for example, utilize magnetic beads with antibodies, for example monoclonal antibodies and polyclonal antibodies, conjugated to the surfaces of the magnetic beads. The antibodies target detectable markers, for example cell surface markers, on cells not of interest and interfering cells. Examples of such magnetic beads include BD IMag™ particles. When a sample containing cells labeled with these magnetic beads is placed in a magnetic field created by a magnetic, for example BD IMagnet™, the magnetic field attracts the cells not of interest which are labeled to the magnet, allowing passage of cells of interest which are not unlabeled. Magnetic depletion allows rapid and effective negative selection of cells of interest. Cells not of interest which are labeled migrate toward the magnet creating the magnetic field, allowing cells of interest which are not labeled in suspension to pass through. Magnetic depletion can be repeated multiple times to increase the purity and concentration of the cells of interest. Magnetic depletion can utilize different types of magnetic beads that target different detectable markers to remove different types of cells not of interest, interfering cells, and debris.

To remove leukocytes, magnetic beads with monoclonal antibody conjugated to their surfaces can be used. These beads are optimized for the depletion of CD4-bearing leukocytes. The CD4 (L3T4) differentiation antigen can be expressed on most thymocytes, a subpopulation of mature T lymphocytes (i.e., MHC class II-restricted T cells, including most T helper cells), and a subset of nature killer T (NK-T) cells. In addition, CD4 can be expressed on pluripotent hematopoietic stem cells, bone marrow myeloid and B-lymphocyte precursors, intrathymic lymphoid precursors, and a subset of splenic dendritic cells.

Flow Cytometry

In some embodiments, isolating one or more cells of interest in the enriched cell sample can be performed with a flow cytometer. In some embodiments, the flow cytometer utilizes fluorescence-activated cell sorting.

Flow cytometry is a valuable method for the analysis and isolation of cells. As such it has a wide range of diagnostic and therapeutic applications. Flow cytometry utilizes a fluid stream to linearly segregate cells such that they can pass, single file, through a detection apparatus. Individual cells can be distinguished according to their location in the fluid stream and the presence of detectable markers. Cells flow through the focused interrogation point where at least one laser directs a laser beam to a focused point within the channel. The sample fluid containing cells is hydrodynamically focused to a very small core diameter by flowing sheath fluid around the sample stream at a very high volumetric rate. The small core diameter can be fewer than 10, 20, 30, 40, 50, 60, 70, 80, 90, 100, 110, 120, 130, 140, 150, 160, 170, 180, 190, 200 micrometers, or a number or a range between any two of these values. The volumetric rate of the sheath fluid can be on the order of at least 10, 20, 30, 40, 50, 60, 70, 80, 90, 100, 200, 300, 400, 500, 600, 700, 800, 900, or 1000 times, or a number or a range between any two of these values, the volumetric rate of the sample. This results in very fast linear velocities for the focused cells on the order of meters per second. So each cell spends a very limited time in the excitation spot, for example fewer than 1, 2, 3, 4, 5, 6, 7, 8, 9, 10, 20, 30, 40, 50, 60, 70, 80, 90, 100 microseconds, or a number or a range between any two of these values. Once the cells pass the interrogation point the cells cannot be redirected to the interrogation point again because the linear flow velocity cannot be reversed.

Flow cytometers are analytical tools that enable the characterization of cells on the basis of optical parameters such as light scatter and fluorescence. In a flow cytometer, cells in a fluid suspension are passed by a detection region in which the cells are exposed to an excitation light, typically from one or more lasers, and the light scattering and fluorescence properties of the cells are measured. Cells or components thereof typically are labeled with fluorescent dyes to facilitate detection. A multiplicity of different cells or components can be simultaneously detected by using spectrally distinct fluorescent dyes to label the different cells or components. In some implementations, a multiplicity of photodetectors, one for each of the scatter parameters to be measured, and one for each of the distinct dyes to be detected are included in the analyzer. The data obtained comprise the signals measured for each of the light scatter parameters and the fluorescence emissions.

Isolation of biological cells has been achieved by adding a sorting or collection capability to flow cytometers. Cells in a segregated stream, detected as having one or more desired characteristics, are individually isolated from the sample stream by mechanical or electrical removal. This method of flow sorting has been used to sort cells of different types, to separate sperms bearing X and Y chromosomes for breeding, to sort chromosomes for genetic analysis, and to isolate particular organisms from complex biological populations.

A common flow sorting technique utilizes drop sorting in which a fluid stream containing linearly segregated cells is broken into drops and the drops containing cells of interest are electrically charged and deflected into a collection tube by passage through an electric field. Drop sorting systems are capable of forming drops at a rate of about 100, 500, 1000, 2000, 3000, 4000, 5000, 6000, 7500, 10000, 20000, 30000, 40000, 50000, 60000, 75000, 100000, 200000, 300000, 400000, 500000, 600000, 750000, 1000000 drops/second, or a number or a range between any two of these values, in a fluid stream that is passed through a nozzle having a diameter less than 1000, 750, 600, 500, 400, 300, 200, 100, 75, 60, 50, 40, 30, 20, 10, 5, 2, 1 micrometers, or a number or a range between any two of these values. Drop sorting requires that the drops break off from the stream at a fixed distance from the nozzle tip. The distance is normally on the order of a few millimeters from the nozzle tip and can be maintained for an unperturbed fluid stream by oscillating the nozzle tip at a predefined frequency.

The linearly segregated cells in the stream can be characterized as they pass through an observation point situated just below the nozzle tip. Once a cell is identified as meeting about 1, 2, 3, 4, 5, 6, 7, 8, 9, 10, 20, 30, 40, 50, 60, 75, 100, 200, 300, 400, 500, 600, 750 criteria, or a number or a range between any two of these values, or more than 1000 criteria, the time at which it will reach the drop break-off point and break from the stream in a drop can be predicted. Possibly, a brief charge is applied to the fluid stream just before the drop containing the selected cell breaks from the stream and then grounded immediately after the drop breaks off. The drop to be sorted maintains an electrical charge as it breaks off from the fluid stream, and all other drops are left uncharged. The charged drop is deflected sideways from the downward trajectory of the other drops by an electrical field and collected in a sample tube. The uncharged drops fall directly into a drain.

Cytometers can further comprise means for recording the measured data and analyzing the data. For example, data storage and analysis can be carried out using a computer connected to the detection electronics. For example, the data can be stored in tabular form, where each row corresponds to data for one cell, and the columns correspond to each of the measured parameters. The use of standard file formats, such as an "FCS" file format, for storing data from a flow cytometer facilitates analyzing data using separate programs and/or machines. Using current analysis methods, the data typically are displayed in 2-dimensional ("2D") plots for ease of visualization, but other methods can be used to visualize multidimensional data.

The parameters measured using a flow cytometer typically include the excitation light that is scattered by the cell along a mostly forward direction, referred to as forward scatter ("FSC"), the excitation light that is scattered by the cell in a mostly sideways direction, referred to as side scatter ("SSC"), and the light emitted from fluorescent molecules in one or more channels (range of frequencies) of the spectrum, referred to as FL1, FL2, etc., or by the fluorescent dye that is primarily detected in that channel. Different cell types can be identified by the scatter parameters and the fluorescence emissions resulting from labeling various cell proteins with dye-labeled antibodies.

Fluorescence-activated cell sorting or is a specialized type of flow cytometry. It provides a method for sorting a heterogeneous mixture of cells into two or more containers or wells of a microtiter plate, one cell at a time, based upon the specific light scattering and fluorescent characteristics of each cell. It records fluorescent signals from individual cells, and physically separates cells of particular interest. The acronym FACS is trademarked and owned by Becton Dickinson.

The cell suspension is placed near the center of a narrow, rapidly flowing stream of liquid. The flow is arranged so that on the average (Poisson distribution) there is a large separation between cells relative to their diameter. A vibrating mechanism causes the stream of cells to break into individual droplets. The system is adjusted so that there is a low probability of more than one cell being in a droplet. Just before the stream breaks into droplets the flow passes through one or more laser intersects where the fluorescent character of interest of each cells are measured. If a cell is to be collected, a charge is applied to the flow cell during the period of time one or more drops form and break off from the stream. These charged droplets then fall through an electrostatic deflection system that diverts droplets into target containers based upon the charge applied to the droplet.

Figure 9:
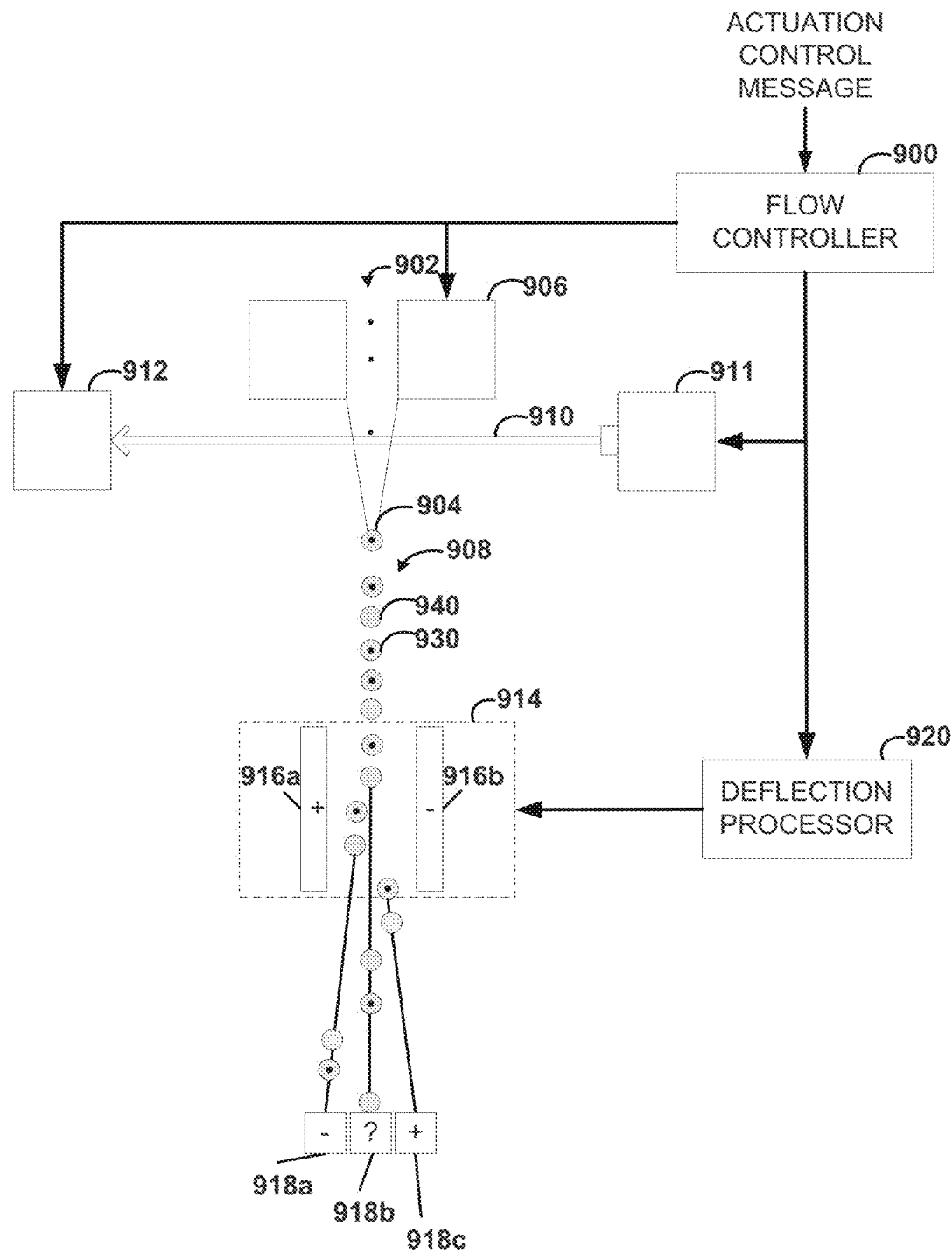
FIG. 9 is a non-limiting schematic illustration of a cell sorter system.

FIG. 9 shows a functional block diagram for one example of a sorting device, for example a flow cytometer, suitable to use for cell sorting, for example at 116B of FIG. 1B. The sorting device illustrated in FIG. 9 can be referred to as stream-in-air sorting system. Cells in sample stream 902 are shown. The sample stream 902 passes through an orifice 904 of a nozzle 906. The sample stream 902, upon exiting the nozzle 906 forms a jet 908. A laser beam 910 is generated by a laser 911 to illuminate the cells that can be included in the jet 908. The light is detected by a detection station 912 to generate multiple signals that are processed to generate a multi-parameter event data point. The generated event data can be provided to a sample behavior analyzer. The providing can be direct, via communication intermediaries (e.g., network/cloud), via memory, or a hybrid configuration.

Based on the values of the multiple signals, prior to droplets leaving jet 908, they are positively charged, negatively charged, or left neutral. Some droplets will include a cell of the sample as shown by a droplet 930 while other droplets will not include a cell of the sample as shown by a droplet 940. Droplets pass through a deflection field 914. The deflection field 914 includes two oppositely charged deflection plates 916a and 916b. The deflection plates 916a and 916b are configured to steer charged droplets in the jet 908 to their respective collection vessels 918a, 918b, or 918c. As shown, vessel 918b collects negatively charged droplets because the positive deflection plate 916a will attract negatively charged droplets. Similarly, vessel 918c will collect positively charged droplets because the negatively charged deflection plate 916b will attract positively charged droplets. Each collection vessel can be a microtiter plate or a well of a microtiter plate.

In one collection scheme, the flow system identifies all cells of interest as they pass the detection station 912 based on the values of their signals, and then causes jet 908 to be charged or neutral at the instant the cell of interest leaves jet 908 as a droplet. In this way, cells of interest are caused to have the same charge. This allows collection of the cells in the same collection vessel, including the same or different wells of a multitier plate.

Non-limiting examples of the sorting device illustrated in FIG. 9 suitable to use for cell sorting, for example at 116B of FIG. 1B, include a BD FACSJazz™ cell sorter, a BD FACSseq™ cell sorter, or any other cell sorters including a Bio-Rad Laboratories, Inc. (Hercules, Calif.) S3e™ Cell Sorter, a Sony Biotechnology Inc. (San Jose, Calif.) SH800 cell sorter, a Beckman Coulter Inc. (Brea, Calif.) MoFlo™ XDP cell sorter.

Sorting Speed

In some embodiments, cells of interest can be sorted into one or more microtiter plates (i.e., isolated from the cell sample) (e.g., at 116B of FIG. 1B) in less than about 15 minutes, allowing time course data to be collected. Cells of interest in a sample can also be sorted in less than 0.01, 0.05, 0.1, 0.5, 1, 2, 3, 4, 5, 6, 7, 8, 9, 10, 15, 20, 25, 30, 45, 50, 55, 60, 70, 80, 90, 100, 110, 120, 130, 140, 150, 175, 200, 250, 300, 400, 500, 600, 750, 1000 minutes, or a duration or range between any of these two values.

The low-cost, high-throughput, single-cell genomic sequencing methods disclosed herein are fast and have high success rate. For example, the method can sort cells to obtain 96, 324, 946, or more cells of interest in less than about 0.1, 0.5, 1, 2, 3, 4, 5, 6, 7, 8, 9, 10, 15, 20, 25, 30, 45, 50, 55, 60, 70, 80, 90, 100, 110, 120, 130, 140, 150, 175, 200, 250, 300, 400, 500, 600, 750, 1000 minutes, or a duration or range between any of these two values. In some embodiments $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ cells, or a number or range between any of these two values, can be sorted per second.

Cell Surface Markers

In some embodiments, the methods utilize the tagging and staining of cell surface markers for cell sorting. In some embodiments, the methods utilize the tagging of cell surface markers for magnetic depletion of cells not of interest, interfering cells, and debris. In some embodiments, the methods include one or more of determining genotype of the patient based on the obtained sequence information; determining phenotype of the patient based on the obtained sequence information; determining one or more genetic mutation of the patient based on the sequence information; and predicting susceptibility of a patient to one or more diseases. At least one of the one or more diseases is cancer or a hereditary disease.

FACS can sort cells based on the tagging and staining of cell surface markers using antibodies that target detectable cell markers. The antibodies include monoclonal and polyclonal antibodies that are coupled to fluorophores. Detectable cell markers include cell surface markers on cells of interest. In some embodiments, magnetic depletion can be based on the tagging of cell surface markers with magnetic beads with antibodies, including monoclonal antibodies and polyclonal antibodies, conjugated to their surfaces targeting cells not of interest, interfering cells, and/or debris. Non-limiting examples of cells surface markers include CD surface markers, growth factor/cytokine, chemokine receptors, nuclear receptors, and other receptors. Examples of cell surface markers include, but are not limited to, ALCAM; CD166; ASGR1; BCAM; BSG; CD147; CD14; CD19; CD2; CD200; CD127 BV421; CD25 BB515; CD161 PE; CD45RA PerCP-Cy™5.5; CD15S AF647; CD4 APC-H; CD4; CD25; CD127; CD45RA; CD15S; CD161; CD3; EpCAM; CD44; and Her2/Neu. Examples of growth factors/cytokines, chemokine receptors include ACVR 1B; ALK4; ACVR2A; ACVR2B; BMPR1A; BMPR2; CSF1R; MCSFR; CSF2RB; EGFR; EPHA2; EPHA4; EPHB2; EPHB4; and ERBB2. Examples of nuclear receptors include androgen receptor; CAR; ER Alpha; ER Beta; ESRRA; ESRRB; ESRRG; FXR; Glucocorticoid Receptor; LXR-a; LXR-b; PPARA; PPARD; PPARG; PXR; SXR; Estrogen Receptor Beta; Progesterone Receptor; RARA; RARE; RARG; RORA; RXRA; RXRB; THRA; THRB; and Vitamin D3 Receptor. Examples of other receptors include AGER; APP; CLEC12A; MICL; CTLA4; FOLR1; FZD1; FRIZZLED-1; KLRB1A; LRPAP1; NCR3; NKP30; OLR1; PROCR; PTPN1; SOX9; SCARB2; TACSTD2; TREM1; TREM2; TREML1; and VDR.

Microtiter Plates

In some embodiments, the methods include enriching a sample comprising a plurality of cells for cells of interest to produce an enriched cell sample, wherein enriching the sample comprises focusing cells of interest in the sample; isolating one or more cells of interest in the enriched cell sample with a flow cytometer and depositing the one or more cells of interest into one or more microtiter plates; and obtaining sequence information of one or more polynucleotides from each of the one or more isolated cells. In some embodiments, a microtiter plate can have at least 96 wells.

In some embodiments, sorting cells of interest (e.g., at 116B of FIG. 1B) from the enriched cell sample includes depositing the one or more cells of interest into one or more microtiter plates. Time course data can be collected while the cells are in the one or more microtiter plates. The size of the microtiter plate can vary. For example, the microtiter plate can have at least 96 cells. In some embodiments, the microtiter plate has, or has about, 96 wells, 384 wells, 1536 wells, 3456 cells, 9600 wells, or a number or a range between any two of these values. In some embodiments, cells of interest can be sorted into 384-well and 1536-well microtiter plates and microtiter plates with higher well density, for example, about 2000, 2500, 3000, 3500, 4000, 5000, 6000, 7500, 10000, 12500, 15000, 20000, 30000, 40000, 50000, 60000, 75000, 100000 wells per microtiter plate.

Cell Lysis

Each well of the one or more microtiter plates can contain a cell lysis buffer, for example a detergent-based single-cell lysis buffer. Each well can also contain RNA stabilizers, molecular labels, cell-specific labels, or a combination thereof. The plates with sorted cells can be kept frozen at −80° C. before further processing.

In certain embodiments, preferential lysis results in lysis of at least 1%, 2%, 3%, 4%, 5%, 6%, 7%, 8%, 9%, 10%, 20%, 30%, 40%, 50%, 60%, 70%, 80%, 90%, 95%, 99%, or a number or range between any two of these values, of cells of interest, e.g., red blood cells or fetal nucleated red blood cells, and lysis of less than 50%, 40%, 30%, 20%, 10%, 5%, 1%, or a number or range between any two of these values, of cells not of interest, e.g. maternal white blood cells or maternal nucleated red blood cells.

Each cell can be lysed, and the mRNA content indexed with a unique sample and molecular index during a reverse transcription step. The identification of cellular composition can utilize 10, 20, 30, 40, 50, 60, 70, 80, 90, 100, 200, 300, 400, 500, 600, 700, 800, 900, 1000, 2000, 3000, 4000, 5000, 6000, 7500, 10000 or a number or a range between any two of these values, genes. One sequencing library can be generated and run on a sequencing instrument. In some embodiments, prior to generating the sequencing library, products can be pooled from about 2, 3, 4, 5, 6, 7, 9, 10, 11, 12, 13, 14, 15, 16, 17, 18, 19, 20, 25, 30, 40, 50, 60, 75, 100, 200, 300, 400, 500, 600, 760, 1000, 2000, 3000, 4000, 5000, 6000, 7500, 10000, or a number or a range between any two of these values, microtiter plates, or a number of microtiter plates between any two of these values. More than one sequencing library can be generated. For example, about 2, 3, 4, 5, 6, 7, 9, 10, 11, 12, 13, 14, 15, 16, 17, 18, 19, 20, 25, 30, 40, 50, 60, 76, 100, 200, 300, 400, 500, 600, 760, 1000, 2000, 3000, 4000, 5000, 6000, 7500, 10000, or a number or a range between any two of these values, sequencing libraries can be generated. Any number of sequencing libraries between two of these values can be generated.

Polynucleotide Targets

In some embodiments, the methods include enriching a sample comprising a plurality of cells for cells of interest to produce an enriched cell sample, wherein enriching the sample comprises focusing cells of interest in the sample; isolating one or more cells of interest in the enriched cell sample; and obtaining sequence information of one or more polynucleotides from each of the one or more isolated cells, wherein the one or more polynucleotides include RNA or mRNA. In some embodiments, the sequence information includes transcript counts of at least 10 genes. The RNA can be obtained from exosome.

Non-limiting examples of polynucleotide targets, for example gene targets and mRNA targets, include CD4, FOX01, CD45RO, MYC, IL1R2, PRF1, GZMK, LGALS1, IL17F, IL23R, LYNX1, PRDM1, SELL, SMAD4, ICOS, IKZF5, RORC, AHRR, CTLA4, ITGB7, ENTPD1, CCR8, TSHR, TGFB2, IL12A, IL7R, HLA-DMA, CCR5, TIAF1, BCL6, BHLHE40, CXCR4, and CD307c. Other non-limiting examples of polynucleotide targets include CD3D, GSTP1, TCF7, CD3E, RNB6, RB1, MYB, CD3G, KRT8, CDH1, ERBB3, ERBB2, TCTN1, ESR1, CDKN1A, and TFF3. Other non-limiting examples of polynucleotide targets include ABCB1, ABCG2, ADAM23, AKT1, APC, AR, ATM, BAD, BCL2, BIRC5, BRCA1, BRCA2, C4A, CAI2, CCNA1, CCND1, CCND2, CCNE1, CDH1, CDH13, CDK2, CD326, CDKN1A, CDKN1C, CDKN2A, CSF1, CST6, CTNNB1, CTSD, EGF, EGFR, EMAP-2, ERBB2, ERBB3, ESR1, ESR2, FOXA1, GATA3, GLI1, GPI, GRB7, GSTP1, HIC1, HPRT1, ID1, IGF1, IGF1R, IGFBP3, IL6, JUN, KRT18, KRT19, KRT5, KRT8, LAMP1, MAPK1, MAPK3, MAPK8, MGMT, MKI67, MLH1, MMP2, MMP9, MUC1, MYB, MYC, NME1, NOTCH1, NR3C1, PGR, PLAU, PRDM2, PSMB2, PSMB4, PTEN, PTGS2, PYCARD, RAB7A, RARA, RARB, RASSF1, RB1, REEP5, RNB6, SERPINE1, SFN, SFRP1, SLC39A6, SLIT2, SNAI2, SRC, TBC1D9. TCTN1, TFF3, TGEB1, THBS1, TP73, TWIST1, VEGFA, XBP1, CD3E, CD3G, CD3G, TCF7, ALCAM, CD25, ITGA6, THY1, PROM1, and CXCR4. Other non-limiting examples of polynucleotide targets include BRCA1, BRCA2, TP53, PTEN, MSH2, MLH1, MSH6, PMS2, EPCAM, APC, RB1, MEN1, RET, and VHL.

The polynucleotide targets can be related to blood and lymph diseases; cancers; the digestive system; ear, nose, and throat; diseases of the eye; female-specific diseases; male-specific diseases; glands and hormones; heart and blood vessels; diseases of the immune system; male-specific diseases; muscle and bone; neonatal diseases; the nervous system; nutritional and metabolic diseases; respiratory diseases; and/or skin and connective tissue.

Sample and Cells of Interest

In some embodiments, the methods include enriching a sample comprising a plurality of cells for cells of interest to produce an enriched cell sample, wherein enriching the sample comprises focusing cells of interest in the sample; isolating one or more cells of interest in the enriched cell sample; and obtaining sequence information of one or more polynucleotides from each of the one or more isolated cells. The type of the sample is not limited. For example the sample can be, or comprise, a clinical sample, a biological sample, an environmental sample, or a combination thereof. For example, the sample can include one or more of a biological fluid, tissue and cell from a patient. In some embodiments, the sample can include blood, urine, cerebrospinal fluid, pleural fluid, amniotic fluid, semen, saliva, bone marrow, a biopsy sample, or a combination thereof. In some embodiments, the cells of interest can include stem cells, cancer cells, blood cells, peripheral blood mononuclear cells, circulating tumor cells (CTCs), breast cancer cells, cells at a cell cycle phase of desire, or a combination thereof. In some embodiments, cells of interest in the sample are, or are about 0.0001%, 0.0005%, 0.001%, 0.005%, 0.01%, 0.1%, 0.5%, 1%, 10%, or a number or a range between any two of these values, of total number of cells in the sample. In some embodiments, fewer than 1000, 500, 250, 100, 50, 25, 10, 5, or a number or a range between any two of these values, cells of interest can be isolated from the enriched cell sample.

As used herein, the term "cells of interest" refer to cells being studied. Because cells of interest can be rare and the concentration of cells of interest in the sample can be low, the enrichment of cells of interest can be advantageous in order to speed up the isolation of cells of interest using, for example, cell sorting. Cells of interest can be enriched using focusing, such as acoustic focusing, and magnetic depletion of cells not of interest and interfering cells and debris. Non-limiting examples of cells of interest in samples include cells expressing a malignant phenotype; tumor cells, such as tumor cells which have been shed from tumor into blood or other bodily fluids or bone marrow; benign tumor cells; cancer cells; cancer cells in peripheral blood; thyroid cancer cells; breast cancer cells; circulating tumor cells ("CTCs"); leukemia cells; cancer stem cells; single cells from different cell cycle phases (G0/G1, S, G2); sperms bearing X and Y chromosomes; stem cells; fetal or adult stem cells; multipotent stem cells; nucleated red blood cells ("NRBC") in Thalassemia patients; fetal cells, such as fetal cells in maternal peripheral blood; fetal nucleated red blood cells ("FNRBC") in the maternal circulation; and cells characterized by CD71, CD8, CD34, or CD133. Samples can comprise cells from a mixed cancer cell sample.

Other examples of cells of interest include, but are not limited to, the following cells: circulating endothelial cells; cells infected with a virus, such as cells infected by HIV, cells transfected with a gene of interest; and aberrant subtypes of T-cells or B-cells present in the peripheral blood of subjects afflicted with autoimmune or autoreactive disorders; activated lymphocytes; antigen presenting cells such as monocytes and dendritic cells; pathogenic or parasitic organisms, cells containing intracellular parasites; and cells or microorganisms in dilute fluids like urine.

Non-limiting examples of cell lines include: Jurkat cells, a T-leukemia cell line; SKBR3, an adenocarcinoma derived breast cancer cell line known for overexpression of Her2/neu; T47D, a ductal carcinoma derived breast cancer cell line that demonstrates low to intermediate Her2/neu expression; and HeLa.

The methods disclosed herein can be applicable to samples with low concentration of cells of interest, for example samples with cells of interest. Cells of interest can be rare. In some embodiments, cells of interest are cells that account for less than 0.0001%, 0.0005%, 0.001%, 0.005%, 0.01%, 0.1%, 0.5%, 1%, 2%, 3%, 4%, 5%, 6%, 7%, 8%, 9%, 10%, or a number or a range between any two of these values, of the total number of cells in a sample. In some embodiments, the sample is a fluid sample having no more than 1, 2, 3, 4, 5, 6, 7, 8, 9, 10, 15, 20, 25, 50, 100, 250, 500, 1000, or a number or a range between any two of these values, cells of interest per milliliter of the sample. The fluid sample can comprise, or be, blood (e.g., whole blood, serum, or plasma), urine, saliva, cerebrospinal fluid, pleural fluid, amniotic fluid, semen, or any combination thereof. In some embodiments, cells of interest are, or are about 1 in 10, $10^2$, $10^3$, $10^4$, $10^5$, $10^6$, $10^7$, $10^8$, $10^9$, $10^{10}$, $10^{11}$, $10^{12}$, $10^{13}$, $10^{15}$, $10^{20}$, or a number or a range between any two of these values, of total cells in the sample or per milliliter of the fluid sample. The size of cells of interest can vary. For example, the diameter of the cells of interest can be about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 micrometers, or a number or a range between any two of these values.

According to some embodiments, removal of cells not of interest (e.g., at 108B of FIG. 1B) removes at least 1%, 2%, 3%, 4%, 5%, 6%, 7%, 8%, 9%, 10%, 15%, 20%, 30%, 40%, 50%, 60%, 70%, 80%, 90%, 95%, 99%, or a number or a range between any two of these values, of the cells not of interest and/or debris originally present in the sample. In some embodiments, focusing the cells of interest (e.g., acoustic focusing at 112B of FIG. 1B) increases the concentration of cells of interest in the sample by at least 10%, 20%, 30%, 40%, 50%, 60%, 70%, 80%, 90%, $10^2$%, $10^3$%, $10^4$%, $10^5$%, $10^6$%, $10^7$%, $10^8$%, $10^9$%, $10^{10}$%, $10^{11}$%, $10^{12}$%, $10^{13}$%, $10^{15}$%, $10^{20}$%, or a number or a range between any two of these values. For example, focusing of the cells of interest (e.g., via acoustic focusing at 112B of FIG. 1B) can increases the speed of cell sorting (e.g., at 116B of FIG. 1B) by at least 10-folds, 20-folds, 30-folds, 40-folds, 50-folds, 60-folds, 70-folds, 80-folds, 90-folds, $10^2$-folds, $10^3$-folds, $10^4$-folds, $10^5$-folds, $10^6$-folds, $10^7$-folds, $10^8$-folds, $10^9$-folds, $10^{10}$-folds, $10^{11}$-folds, $10^{12}$-folds, $10^{13}$-folds, $10^{15}$-folds, $10^{20}$-folds, or a range or a number between any two of these values.

Sequencer

Many methods, devices and systems are available for sequencing polynucleotides, and can be used for obtaining sequence information of the polynucleotides from the isolated cells in the methods disclosed herein. For example, non-limiting examples of sequencing instruments include GS FLX Titanium, GS Junior, and GS FLX+ systems (454 Life Sciences, Bradford, Conn.), Solexa system, Genome Analyzer IIx, MiSeq, HiSeq, and HiScanSQ (Illumina, Inc., San Diego, Calif.), the SOLiD™ (Sequencing by Oligonucleotide Ligation and Detection) system and Sanger-based DNA sequencers such as the 3500 Genetic Analyzer and Ion Torrent Sequencing systems such as the Personal Genome Machine or the Proton Sequencer (Thermo Fisher Scientific, Waltham, Mass.), and nanopore sequencing systems (Oxford Nanopore Technologies, Oxford, united Kingdom).

Data Analysis

In some embodiments, the methods include enriching a sample comprising a plurality of cells for cells of interest to produce an enriched cell sample, wherein enriching the sample comprises focusing cells of interest in the sample; isolating one or more cells of interest in the enriched cell sample; and obtaining sequence information of one or more polynucleotides from each of the one or more isolated cells by sequencing the molecularly indexed polynucleotide library. Sequencing the molecularly indexed polynucleotide library can, in some embodiments, include deconvoluting the sequencing result from sequencing the library, possibly using a software-as-a-service platform.

Figure 10:
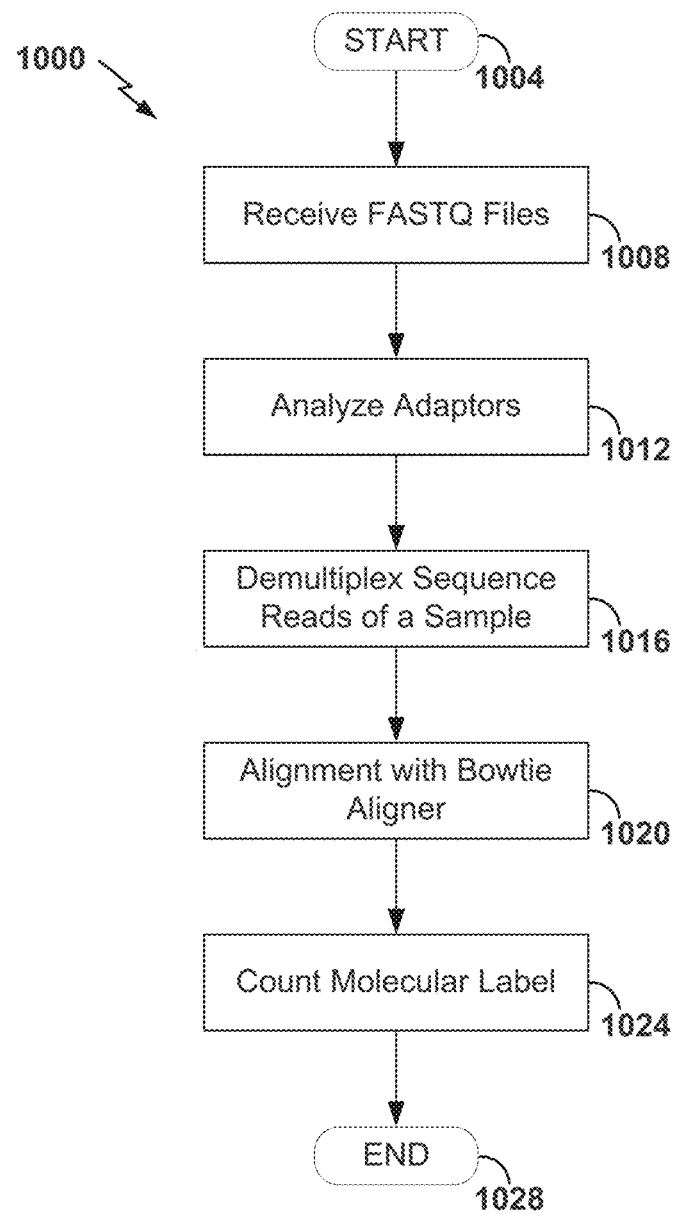
FIG. 10 is a flowchart showing non-limiting exemplary steps of data analysis.
Figure 11:
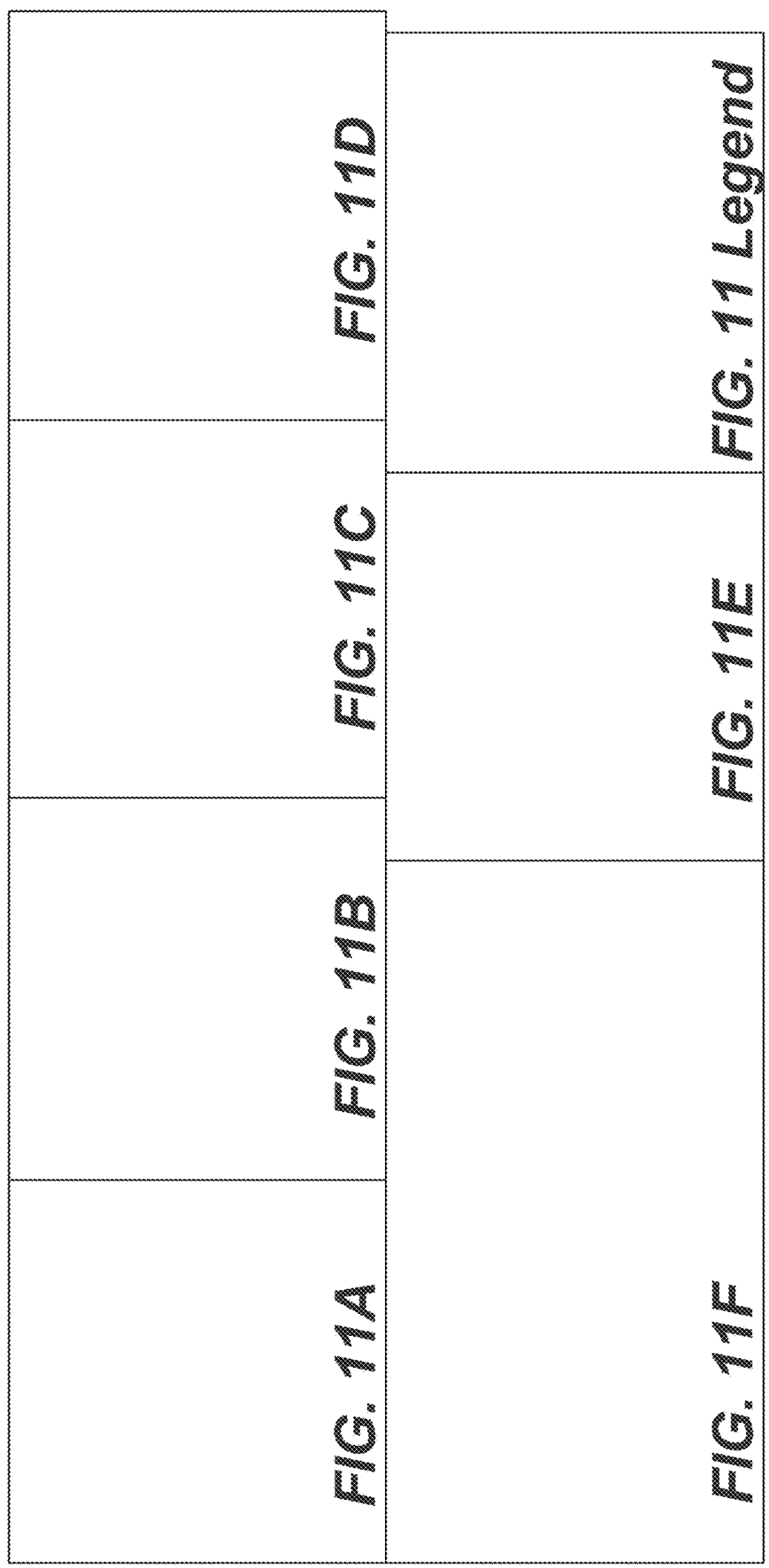
FIGS. 11A-G show gating of single cells for next generation sequencing.
Figure 11A:
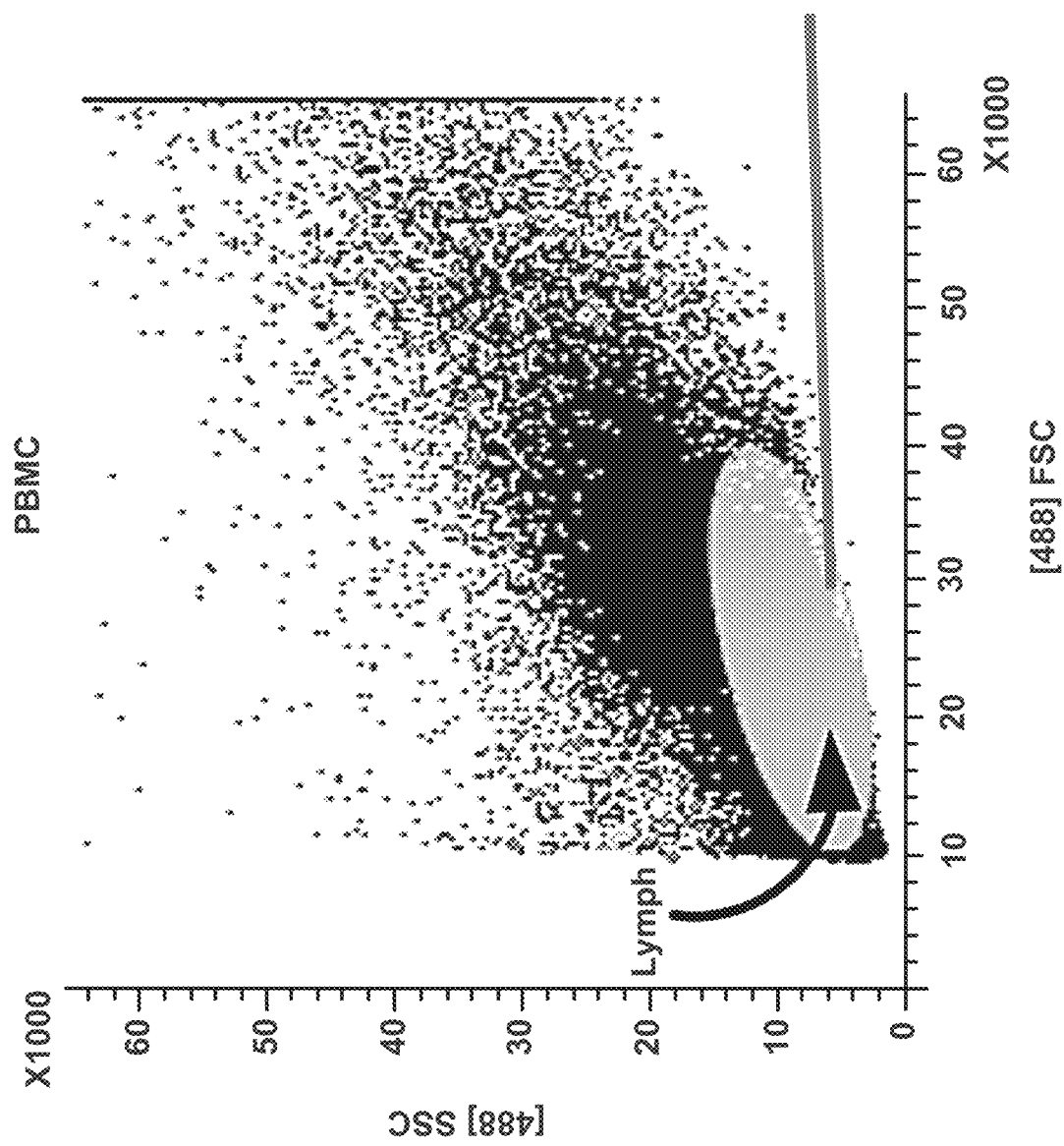
Figure 11B:
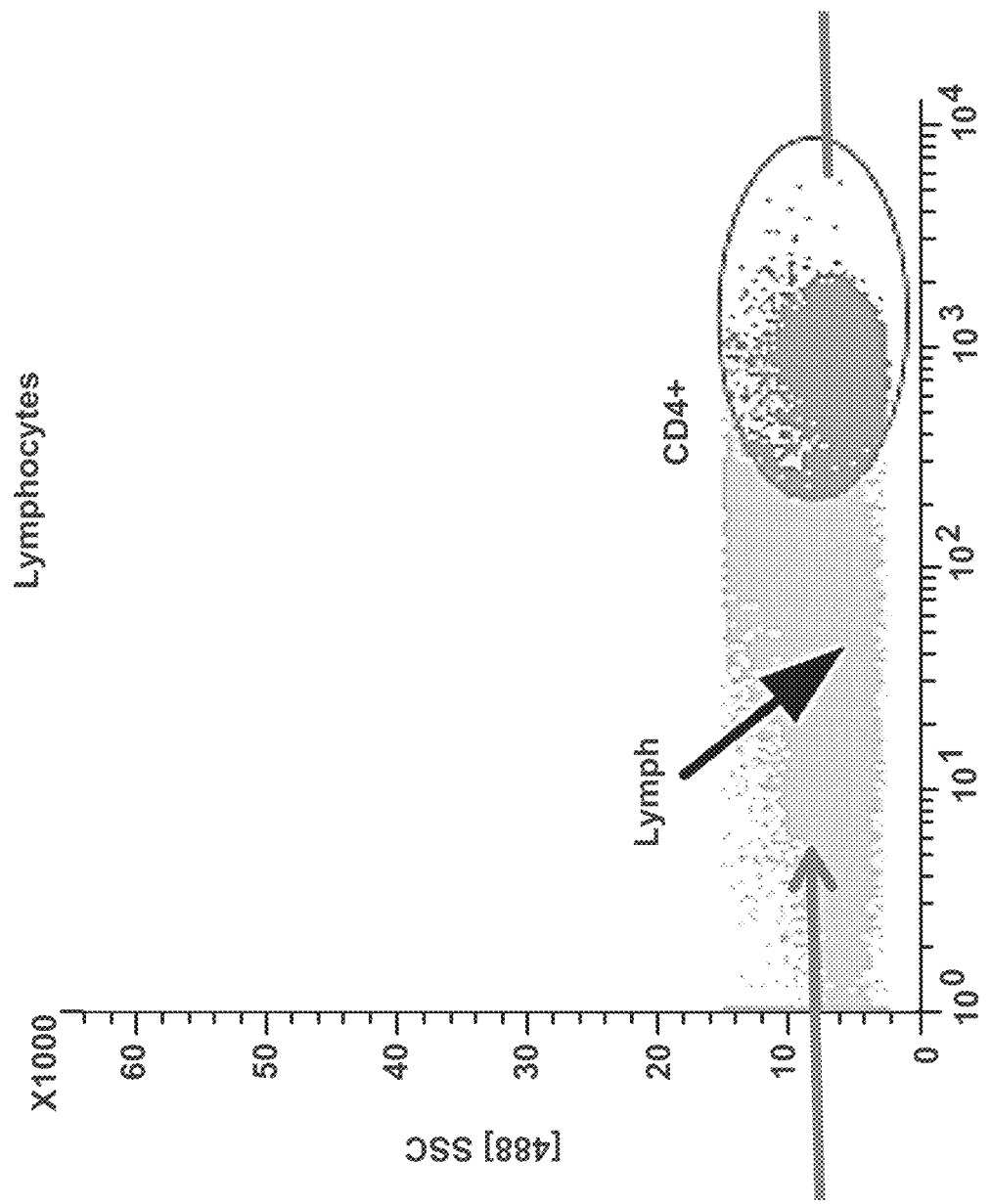
Figure 11D:
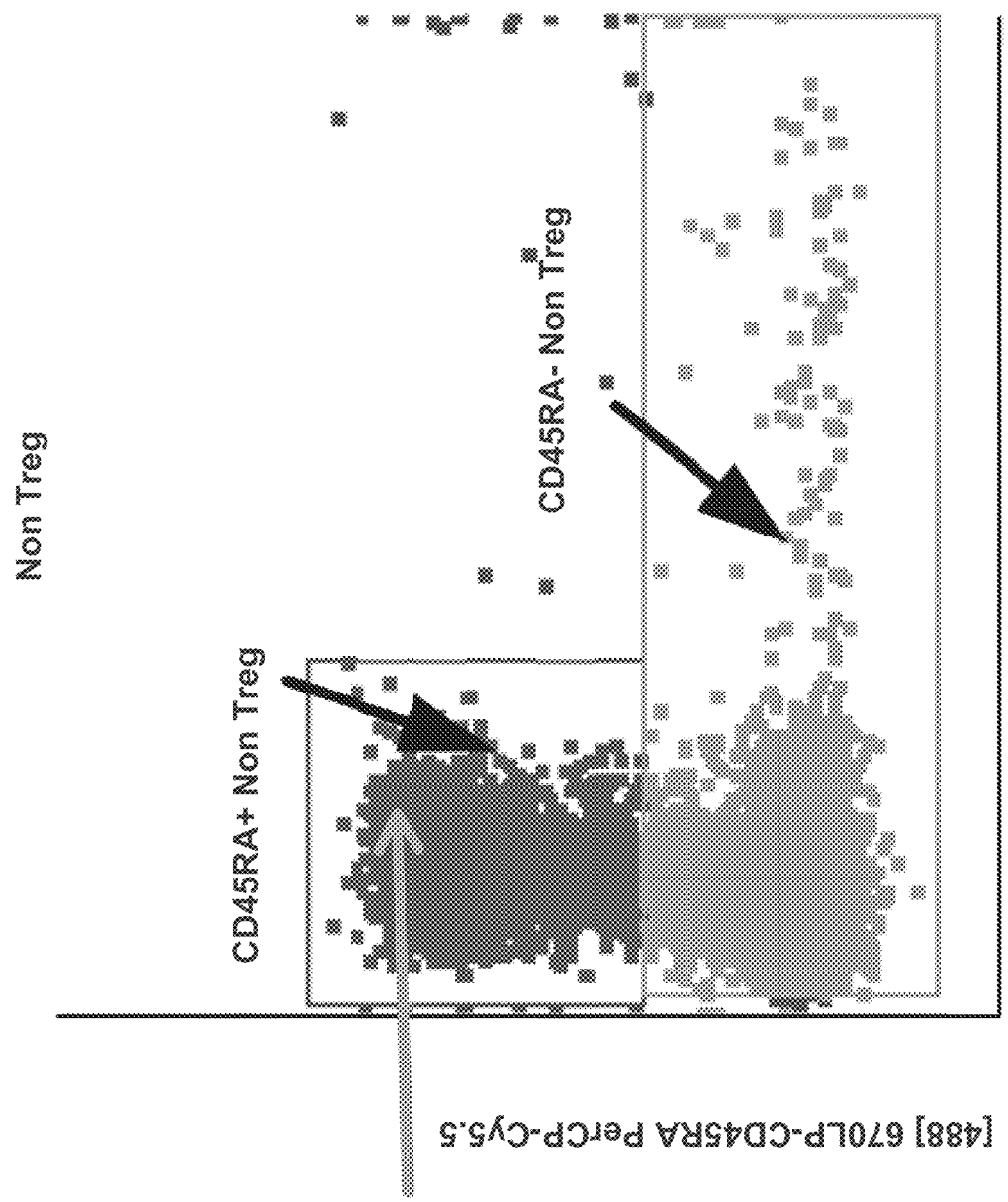
Figure 11G:
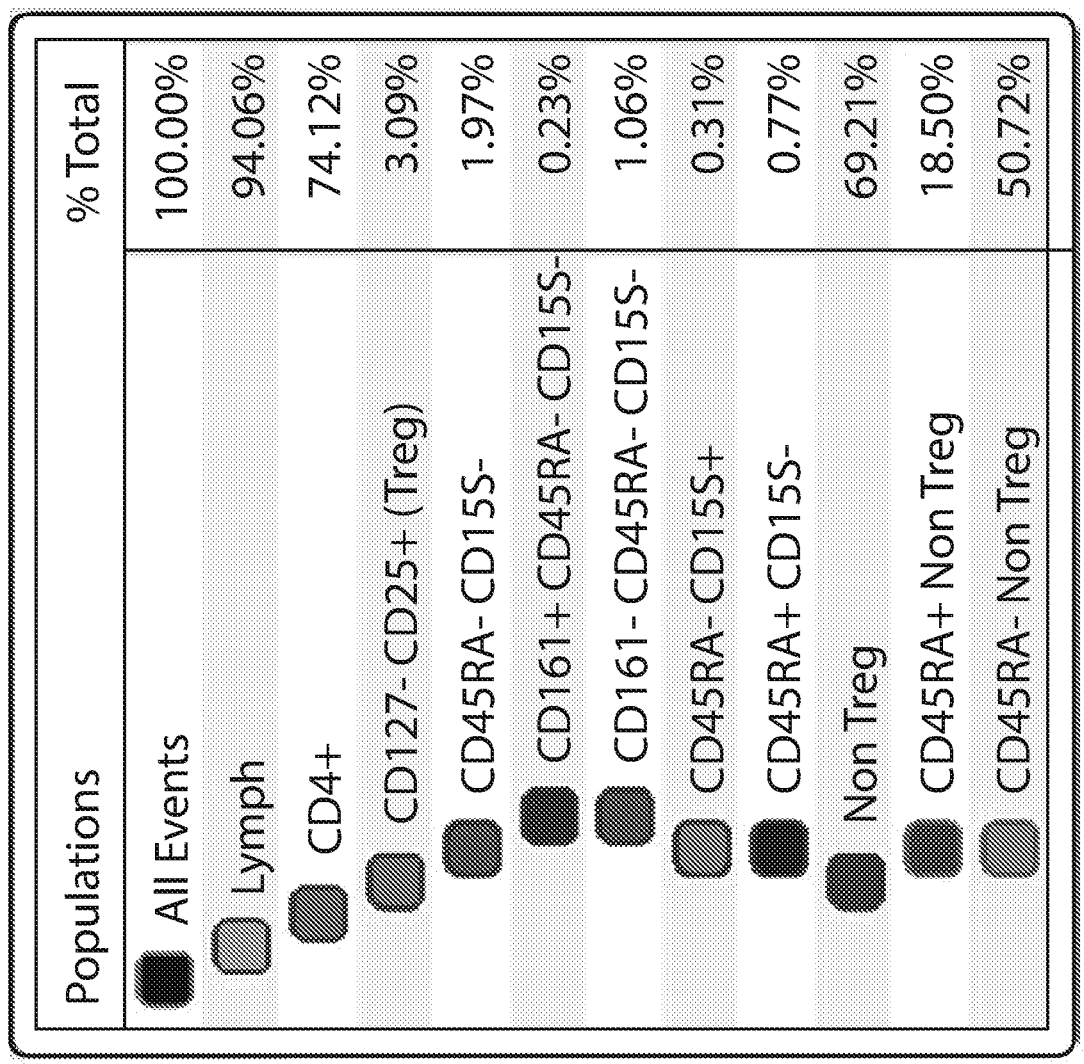

FIG. 10 is a flowchart showing non-limiting exemplary steps of data analysis 1000 for use, for example, at 124B of FIG. 1B. Data analysis can be provided in a secure online cloud environment. In some embodiments, data analysis can be performed using a software-as-a-service platform. Non-limiting examples of secure online cloud environments include the Seven Bridges Genomics platform. The Seven Bridges Genomics platform is a non-limiting example of a software-as-a-service platform.

As shown in FIG. 10, data analysis 1000 starts at 1004. At 1008, a sequencing result is received from, for example, 122B of FIG. 1B. Non-limiting examples of the formats of the sequencing result received from 122B of FIG. 1B include EMBL, FASTA, and FASTQ format. The sequencing result can include sequence reads of a molecularly indexed polynucleotide library. The molecularly indexed polynucleotide library can include sequence information of a plurality of single cells. Sequence information of multiple single cells can be deconvoluted by the following steps. At 1012 the sequences of the adaptors used for sequencing at 122B are determined, analyzed, and discarded for subsequent analysis. The one or more adaptors can include the adaptor 234 and 236 in FIG. 2.

At 1016, the sequencing result of a molecularly indexed polynucleotide library is demultiplexed. Demultiplexing can include classifying the sequence reads as belonging to one of a plurality of single cells. Classifying the sequence reads as belonging to one of a plurality of single cells can be based on the label region 214, for example the sample label 220. The sequence reads belonging to one mRNA can be distinguished from those belonging to another mRNA based on the label region 214, for example the molecular label 218. At 1020, sequence reads can be aligned to mRNA sequences using an aligner. Non-limiting examples of the aligner used at 1020 include the Bowtie aligner, ClustalW, BLAST, ExPASy, and T-COFFEE. At 1024, the digital gene expression profile for each cell is reconstructed by counting, for each mRNA sequence, the number of different molecular labels 218 associated with the mRNA sequence for the cell. Consequently, digital counting of mRNAs in a single cell is achieved. The output of data analysis 1000 can include a spreadsheet of read alignment summaries and molecular label counts for each gene in each cell. Data analysis 1000 ends at 1028.

EXAMPLES

Some aspects of the embodiments discussed above are disclosed in further detail in the following examples, which are not in any way intended to limit the scope of the present disclosure.

Example 1

Comprehensive High-Throughput Single-Cell Analysis Combining Proteomic and Genomic Information: Flow Sorting, Cell & mRNA Indexing, and Sequencing Analysis This example demonstrates comprehensive high-throughput single-cell analysis combining proteomic and genomic information.

Peripheral blood cells were stained with cell surface markers to identify rare regulatory T cell subpopulations including naïve, effector, and non-suppressive regulatory T cells. Cells sampled at various time points were individually sorted into 96-well Precise™ encoding plates using a BD FACSJazz™ cell sorter after sample enrichment with BD Imag™ magnetic separation, thereby increasing sort speed and quality. Each cell was lysed, and the mRNA content was molecularly indexed with a unique sample and molecular index during the reverse transcription step. We interrogated approximately 100 genes that were carefully selected for the identification of cellular composition. After pooling the products from eight 96-well Precise™ encoding plates, three sequencing libraries were generated and run on an Illumina® MiSeq instrument. A streamlined computation pipeline was created, and automated data analysis was performed on the Seven Bridges™ Genomics Platform. These results demonstrate simple and unambiguous de-convolution of cellular subtypes using a high-throughput single-cell genomic sequencing approach combined with the powerful single-cell sorting capabilities of BD FACS analysis Instrumentation.

FIGS. 11A-G are plots showing gating of single cells for next generation sequencing and a legend therefore. Peripheral blood mononuclear cells ("PBMCs") were collected by CPT tube (Cat. No. 362761). The PBMCs were stained with an antibody cocktail containing white blood cell surface markers: CD127 BV421, CD25 BB515, CD161 PE, CD45RA PerCP-CyTM5.5, CD15S AF647, CD4 APC-H (BD), along with the BD Imag™ CD4 T Lymphocyte Enrichment Kit (Cat. No. 557939). The regulatory T cells were identified by CD4+CD25+CD127-staining. The Treg cell populations were further subdivided by two cell surface markers CD45RA and CD15S into naive Tregs (nTregs CD45RA+CD15S−), effector Tregs (eTregs CD45-CD15S+), and non-suppressive Tregs (CD45RA−CD15S−). The non-suppressive Tregs were further divided into CD161+ and CD161− subpopulations. Non-Tregs cells were also collected into CD45RA+ and CD45RA− subpopulations.

Figure 12A:
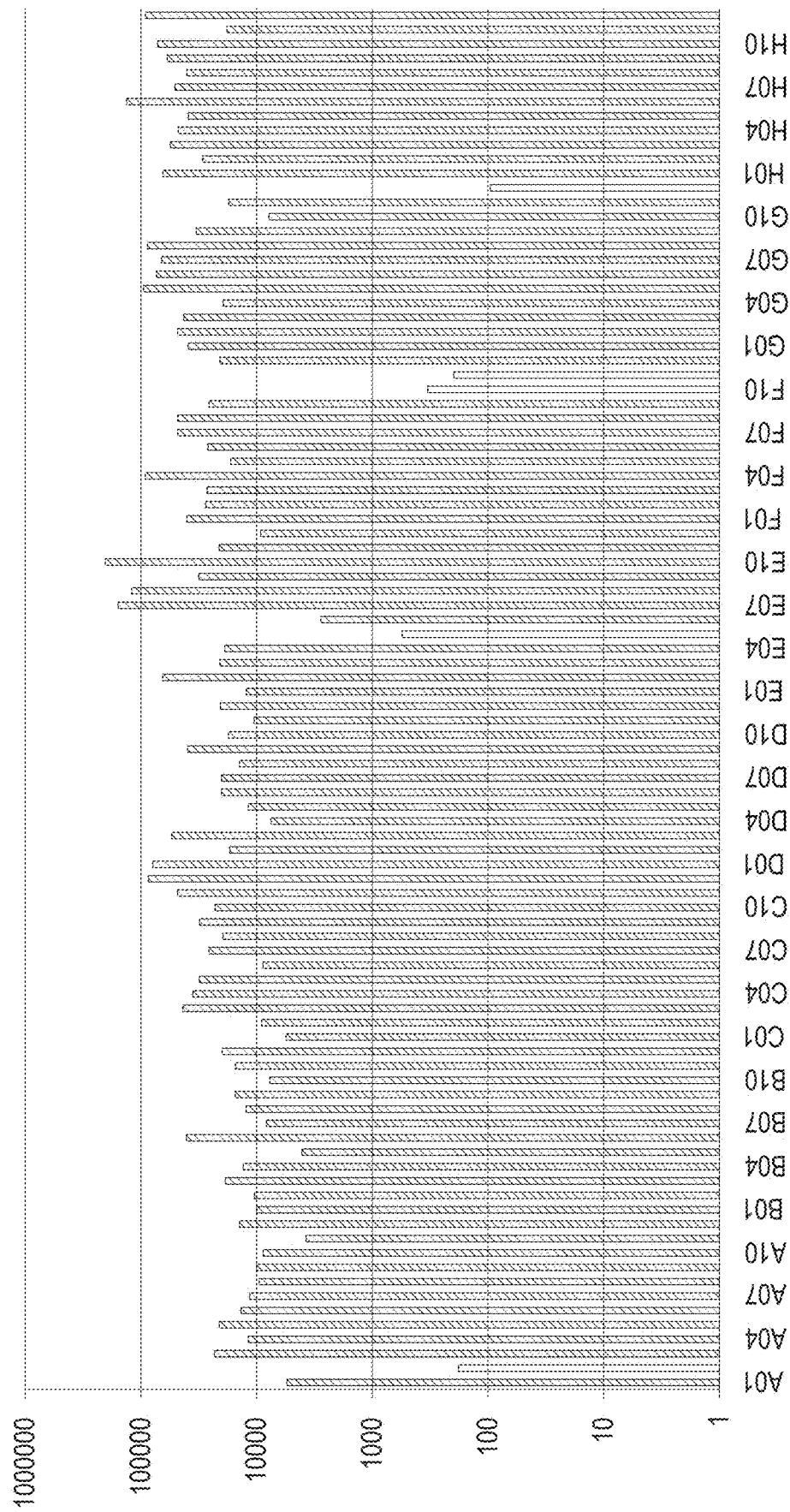
FIGS. 12A-B are bar graphs showing the number of reads and transcripts obtained from single cells.
Figure 12B:
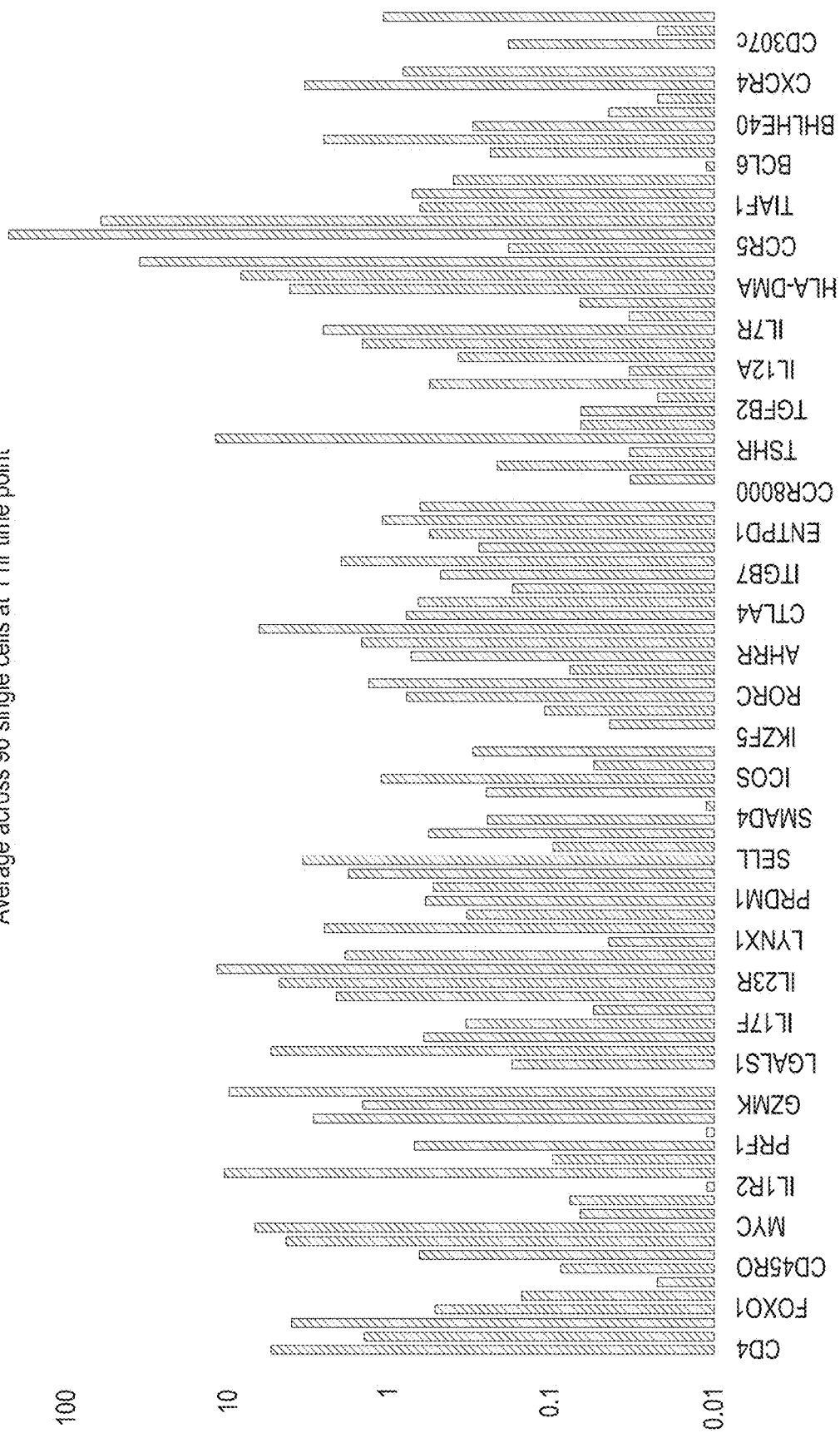

FIGS. 12A-B are bar graphs showing the number of reads and transcripts obtained from single cells. FIG. 12A is a plot showing high sequencing success starting from individual cells sorted into a Precise™ plate. Grey bars indicate possible failures based on significantly lower total read counts. Plate indexing allows multiple plates, up to 4,000 cells, to be pooled into a single MiSeq run if desired. FIG. 12B is a plot showing average transcript count across 96 single cells from the same plate as shown in Panel A after the reads being de-convoluted. Data illustrates absolute mRNA quantitation in single cells across a large measurement range. The success of sorted single-cell sequencing was greater than 95%. Single cells were sorted across a range of time after the samples were stained. 1 hour data point is shown.

Figure 13:
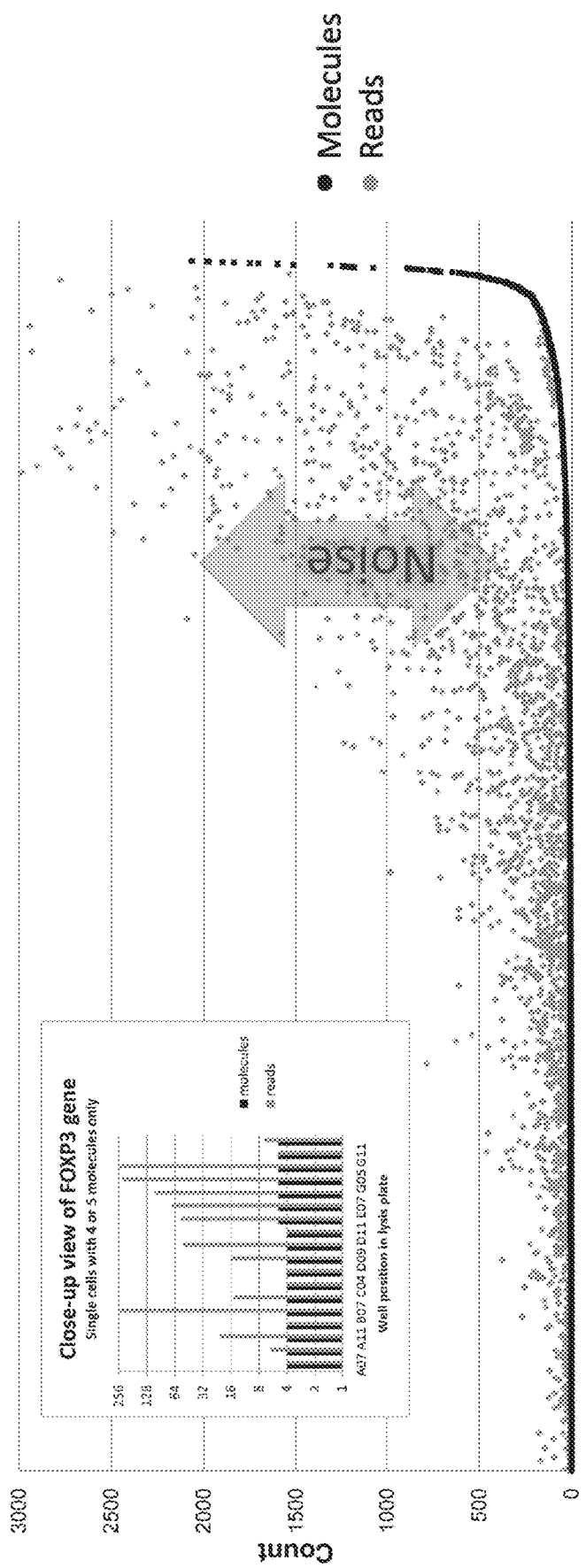
FIG. 13 is a plot of counting reads vs. molecules showing that molecular indexing assay corrects for PCR bias.

FIG. 13 is a plot of counting reads vs. molecules showing that Precise™ assay corrects for PCR bias. The Precise™ assay corrects for PCR amplification bias and allows for absolute counting of transcripts. Counting the number of molecules significantly reduces the noise level associated with counting reads.

Figures 14A, 14B:
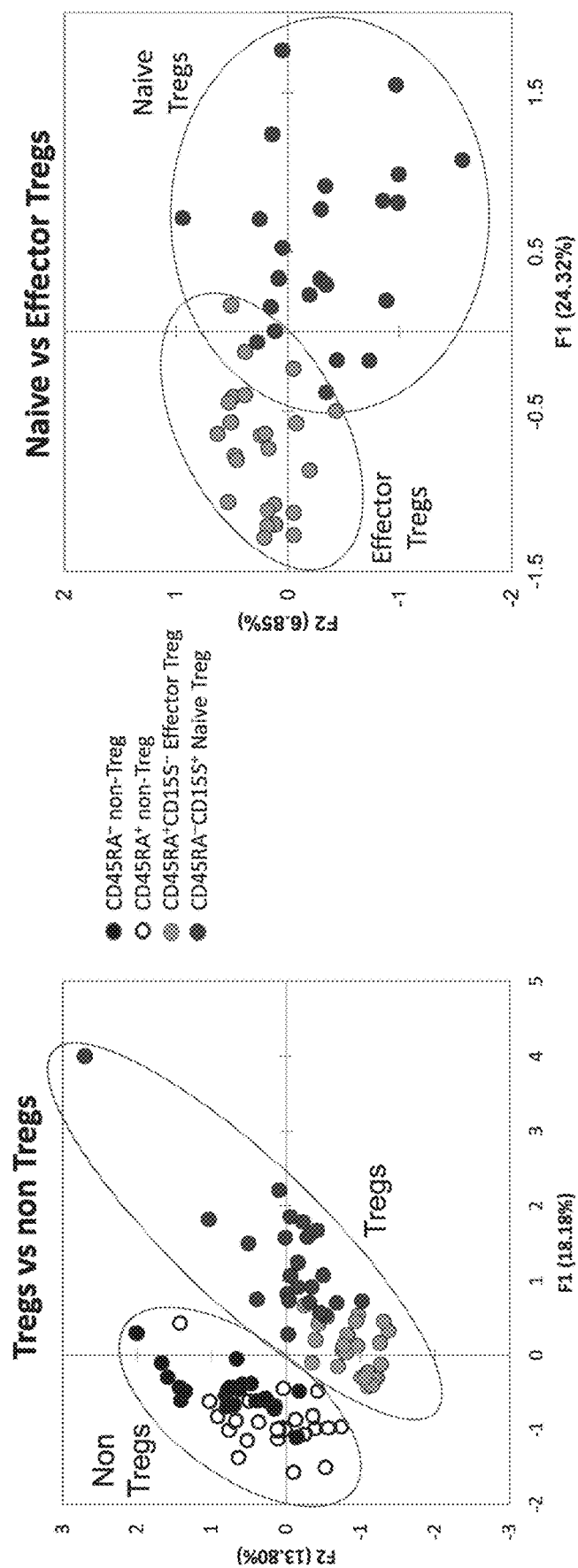
FIGS. 14A-B are principal component analysis ("PCA") plots of Tregs vs. non-Tregs and naïve vs. effector Tregs showing that surface marker phenotypes correlate with molecular profiles.

FIGS. 14A-B are principal component analysis ("PCA") plots of Tregs vs. non-Tregs and naïve vs. effector Tregs showing that surface marker phenotypes correlate with molecular profiles. Principal component analysis was used to cluster the individual cells using their molecular counts for expression across the panel of genes. The identity of each cell was recorded by index sorting on a BD FACSJazz, which was represented by each colored point.

FIGS. 15A-C are PCA single-cell plots of CD45RA− CD15S+, CD161− Non-Suppressive Tregs, and CD45RA+ CD15S− Effector Tregs across time points.

Utilizing the acoustic focusing device in advance of the flow cytometric cell sorting enables the enrichment of cells of interest (less than 1% of the starting population of cells in the sample). This provides for a reduction of sorting time from hours to minutes. This advantageously provides for populations of live cells that can be analyzed at the same point in their life cycle and for a larger population of viable cells.

The example demonstrates low-cost, high-throughput, single-cell genomic sequencing using the BD FACSJazz™ cell sorting instrument in conjunction with the Cellular Research Precise™ workflow. The assay has a high success rate—greater than 95% for single-cell sorting and sequencing. It is fast—one 96-well plate of single cells can be sorted within 15 minutes with enrichment, which minimizes the undesired gene expression changes after sample preparation.

Altogether, these data indicate that the combination of flow single-cell sorting with single-cell barcoding provides a powerful tool for linking cell phenotype with molecular transcript profile.

Example 2

The New BD FACSseg™ Cell Sorter for High-Throughput, High-Precision, Quantitative, Single Cell Gene Expression Profiling This example demonstrates the use of a cell sorter for high-throughput, high-precision, quantitative single cell gene expression profiling. In particular, this example shows simple and unambiguous deconvolution of cellular types using a high-throughput single cell genomic sequencing approach, for example the Cellular Research Precise™ Assay, combined with a single cell sorter, for example the BD FACSseq™ cell sorter.

In this example, complete workflows for single cell sorting for cell cycle analysis and cell surface marker staining applications are disclosed. In particular, this example demonstrates: 1) elimination of dead cells from collection by propidium iodide (PI) staining; 2) isolation of single cells from different cell cycle phases (G0/G1, S, G2) with Hoechst dye staining; 3) accuracy of sorting cells by depositing different numbers of cells (1 cell, 5 cells, 10 cells, 20 cells, and 50 cells) per well in a 96-well plate; and 4) isolation of single cells from a mixed cancer cell sample based on their specific cell surface marker staining. The gene expression profiles of the sorted cells were analyzed and generated using the Precise™ Assay and next generation sequencing.

FIGS. 16A-C are plots showing cell cycle analysis of single cells cells. Jurkat cells, a T-leukemia cell line, were cultured to log phase and stained with Hoechst 34580 dye (5 mg/mL) for half an hour, and PI (Cat. No. 556463, 5 mg/mL) for 10 minutes at room temperature. The cultured Jurkat cells were analyzed using a BD FACSseq™ sorter. FIG. 16A is a plot of trigger pulse width vs. scatter height showing that single cells were identified based on their composite scatters. Propidium iodide (PI) dye is a membrane permeant DNA binding dye that can be excited by a violet laser. FIG. 16B is a plot of PI median fluorescence intensity ("MFI") vs. scatter height showing that cells stained positive with PI are dead or dying and can be excluded from collection. The exclusion of dead cells ensures that only viable, healthy representative cells enter the genomic workflow for analysis. FIG. 16C is a histogram plot of count vs. Hoechst 34580 MFI showing the Hoechst staining signal of live cells. FIG. 16C shows the distribution of G0/G1, S, and G2/M cell cycle phases based on their differential Hoechst dye fluorescence staining intensity.

FIGS. 17A-B are plots showing accurate delivery of single cells and small numbers of cells. The BD FACSseq™ sorter can accurately deliver single cells or a small number of cells of interest. And the phenotype information of the sorted cells can be recorded by the index sorting feature of the BD FACSseq™ sorter. Single or small numbers (5, 10, 20, and 50) of fixed Jurkat cells stained with 4',6-diamidino-2-phenylindole ("DAPI") were sorted in replicates into 96-well plates. FIG. 17A are images of representative wells, as visualized on a fluorescence microscope, and FIG. 17B are plots of DAPI MFI vs. scatter height showing phenotype information of the sorted cells recorded by index sorting.

Figure 18B:
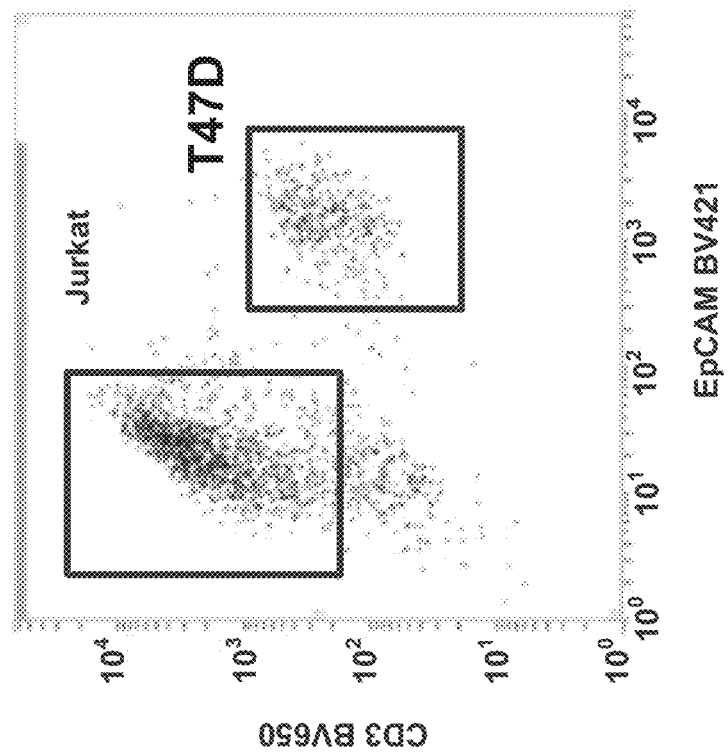
FIGS. 18A-B are plots showing single cell isolation with a cell sorter.
Figure 18A:
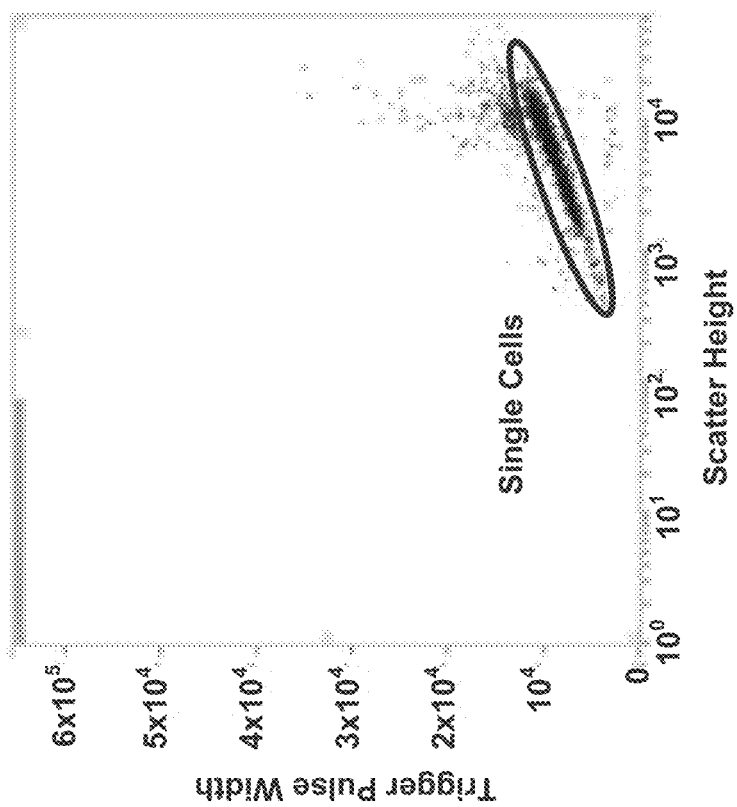

FIGS. 18A-B are plots showing single cell isolation with a BD FACSseq™ cell sorter. A cancer cell sample with Jurkat cells, and T47D cells, a breast cancer cell line, mixed at a 80%:20% ratio, was stained with EpCAM BV421 and CD3 BV650 antibodies and run on a BD FACSseq sorter. FIG. 18A is a plot of trigger pulse width vs. scatter height showing that single cells were gated by composite scatter. FIG. 18B is a plot of CD3 BV650 vs. EpCAM BV421 showing the separation of the two types of cells by their specific surface marker staining. Jurkat cells were only stained positive with CD3, while T47D were only stained with EpCAM. The mixed cells were randomly sorted into each well of a 96-well Cellular Research Precise™ encoded plate, with one single cell in each well.

Figure 19A:
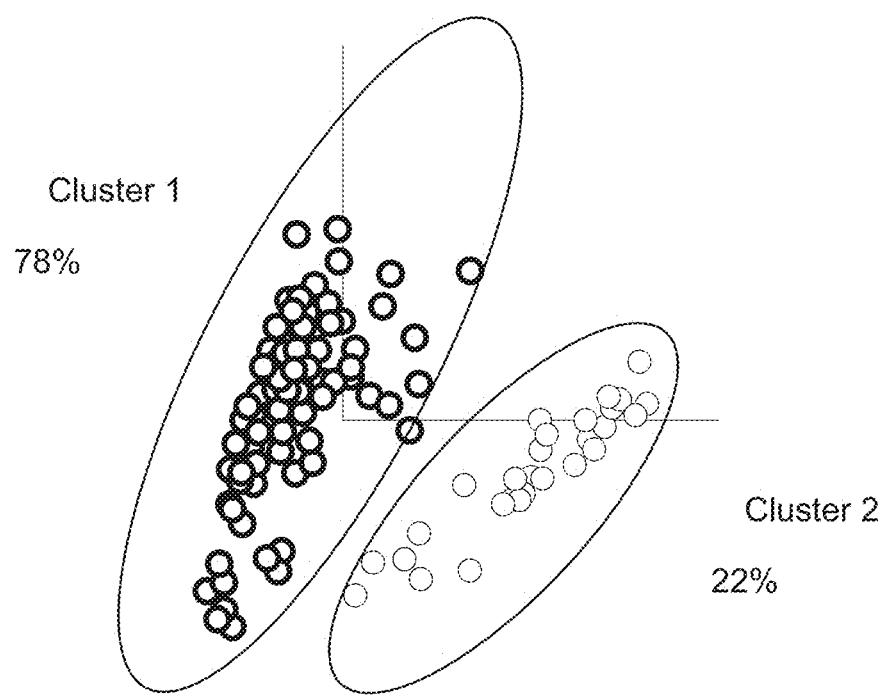
FIGS. 19A-C show PCA clustering and gene expression profiles of Jurkat cells and T47D cells.
Figure 19B:
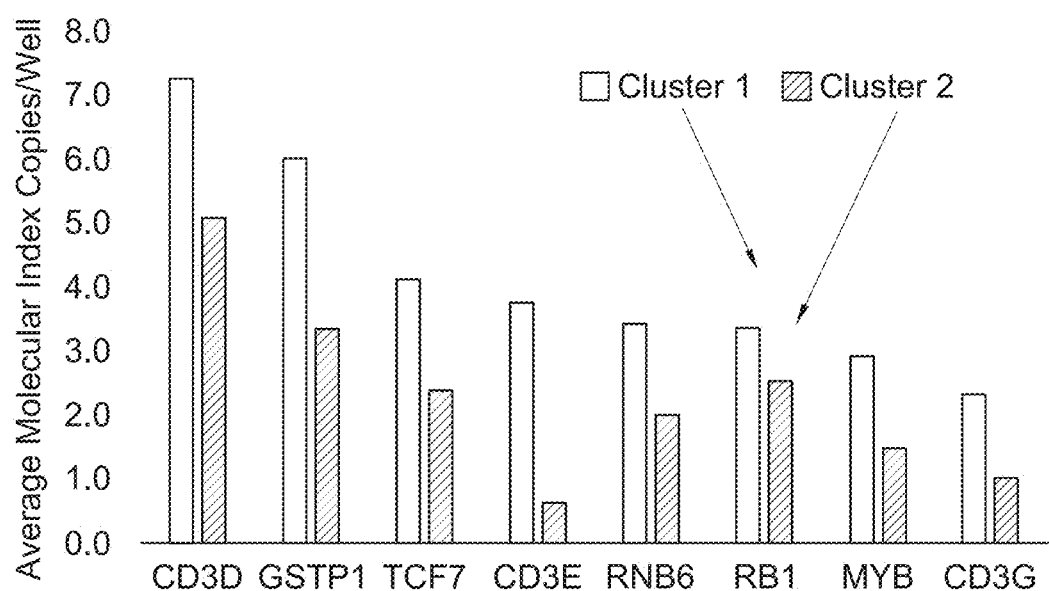
Figure 19C:
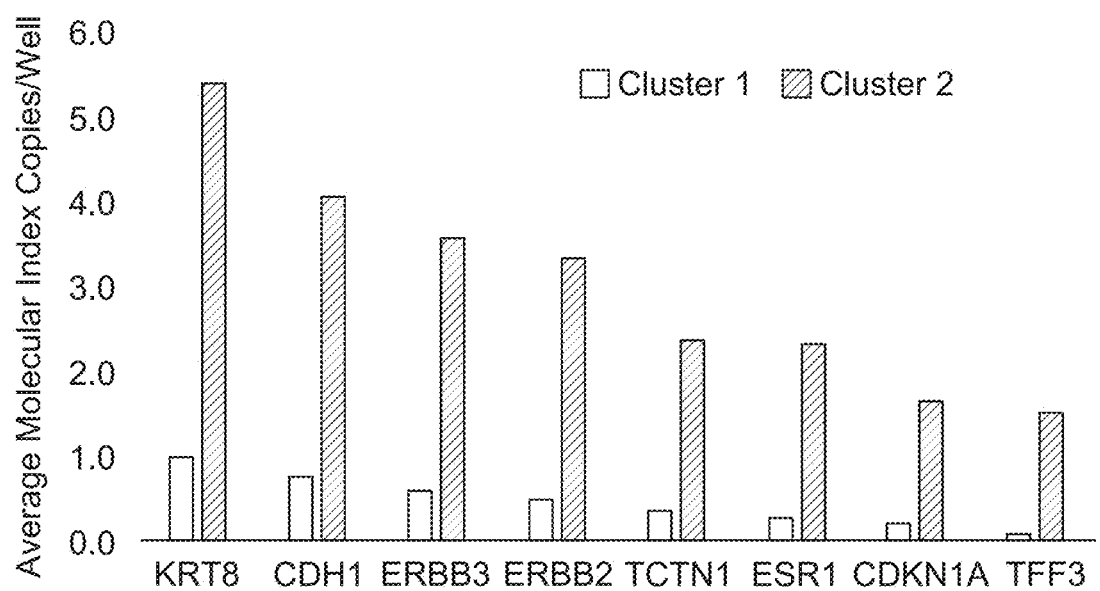

FIGS. 19A-C show PCA clustering and gene expression profiles of Jurkat cells and T47D cells separated by with a BD FACSseq cell sorter shown in FIGS. 18A-B. FIG. 19A is a PCA plot showing clustering of Jurkat cells and T47D cells into two clusters. FIGS. 19B-C are bar graphs showing gene expression profiles in cluster 1 of Jurkat cells and cluster 2 of T47D cells. FIGS. 19B-C show that the genes highly expressed in two clusters corresponded well with Jurkat cells (cluster 1) and T47D cells (cluster 2).

Altogether, these data demonstrate a simple, fast method using a new, easy-to-use sorter to select and isolate single cells for high-resolution genomic studies, including next generation sequencing, qPCR, and microarray analysis. The sorter provides a powerful tool for studying complex samples at the individual cell level.

Example 3

Single Cell Gene Expression Profiles of Her2/Neu-Expressing Cancer Cells Using Molecular Indexing Technology This example demonstrates the determination of single cell gene expression profiles of Her2/neu-expressing cancer cells using molecular indexing technology.

The expression level of Her2/neu (Cerb-B2) in breast cancer is a fundamental classification in the diagnostic process. The overexpression of this oncogene correlates with reduced survival and can be a driving determinant of treatment. However, the mechanisms at work in the aggressive breast cancers associated with Her2/neu overexpression are poorly understood. Conventional gene profile studies utilizing bulk tissue can be hampered by poor signal-to-noise ratios, making it difficult to appreciate changes in gene expression. A single-cell analysis approach can overcome these problems and reveal a more comprehensive data set. The aim of this example was to identify genes that are up-regulated or down-regulated in individual cells that overexpress Her2/neu.

Single cells from a variety of cell lines known to express different levels of Her2/neu were sorted into 96-well plates using the BD FACSseg™ cell sorter. The cell lines used included SKBR3, an adenocarcinoma derived breast cancer cell line known for overexpression of Her2/neu, and T47D, a ductal carcinoma derived breast cancer cell line that demonstrates low to intermediate Her2/neu expression. Negative control cell lines (HeLa and Jurkat) were also included in the screening. These sorted single cells were processed using a molecular indexing technology for breast cancer specific genes. This gene expression panel includes 100 genes associated with breast cancer. The resulting gene profiles were then correlated with Her2/neu expression levels on individual cells.

Cell Culture.

HeLa cells, a cervical epithelial adenocarcinoma cell line, were cultured with minimum essential medium ("MEM"). Jurkat cells, a T-leukemia cell line, were cultured with Roswell Park Memorial Institute medium ("RPMI") 1640 media. SKBR3 cells, a metastatic breast adenocarcinoma cell line, and T47D cells, a ductal breast carcinoma cell line, were both cultured with Dulbecco's minimum essential medium ("DMEM"). All media were supplemented with 10% heat-inactivated fetal bovine serum ("FBS") and 1% Penicillin/Streptomycin solution. In addition, all cell lines were harvested using Gibco StemPro® Accutase® prior to staining.

Flow Cytometry.

HeLa, Jurkat, SKBR3, and T47D human cancer cell lines were cultured to log phase, harvested, and counted. 1×106 cells for each cell line were stained with BD HORIZON™

BV421 Her-2/Neu (BD custom antibody) and BD HORIZON™ BV786 CD44 (BD Biosciences, Cat. No. 564942) for 30 minutes, washed, followed by staining with the cell viability dye Propidium Iodide (BD Biosciences, Cat. No. 51-66211E) for 10 minutes at room temperature. Samples were then analyzed and sorted using a BD FACSseq cell sorter. Based on Her2/Neu protein expression, live single cells were sorted directly into pre-filled Cellular Research Precise™ breast cancer 96-well assay plates.

Sequencing Library Generation and Data Analysis.

Cellular Research Precise™ plates are preloaded with a detergent-based cell lysis buffer along with RNA stabilizers, molecular indices, and sample-specific barcodes. After sorting cells into plates, lysed cells were kept frozen at −80° C. before further processing. These samples were then processed according to the Cellular Research Precise™ assay protocol to pool samples, amplify target genes and generate a sequencing library. The library was then sequenced on an Illumina® MiSeq instrument. A streamlined computation pipeline was created, and automated data analysis was performed on the Seven Bridges Genomics Platform. Data output from Seven Bridges was then analyzed using the Qlucore software package.

Figure 20B:
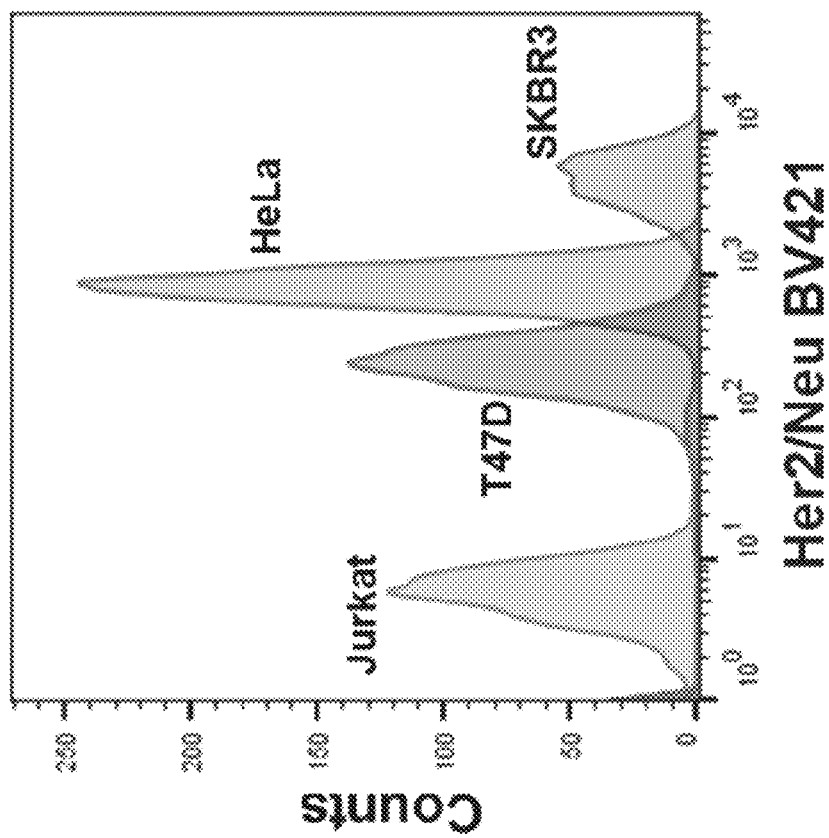
FIGS. 20A-B are plots showing relative protein expression of CD44 and Her2/Neu.
Figure 20A:
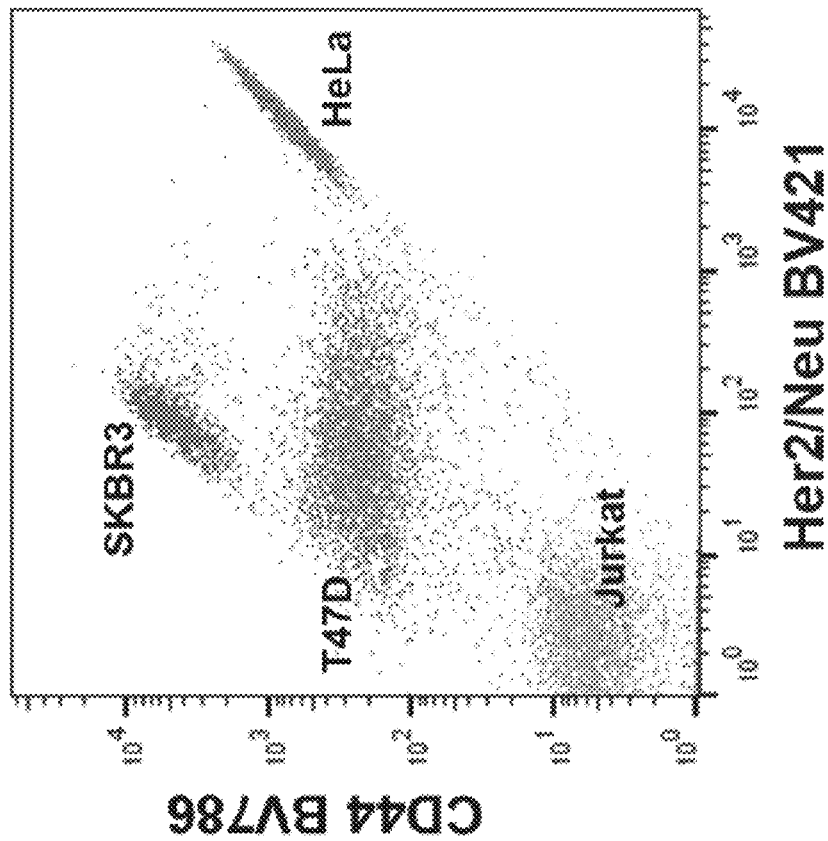

FIGS. 20A-B and 21A-D show relative expressions of CD44 and Her2/Neu. FIGS. 20A-B are plots of CD44 BV786 vs. Her2/Neu BV421 and Counts vs. Her2/Neu BV421 showing that each cell type, Jurkat, T47D, HeLa, and SKBR3, was clearly defined by relative expression of CD44 and Her2/Neu.

Figure 21A:
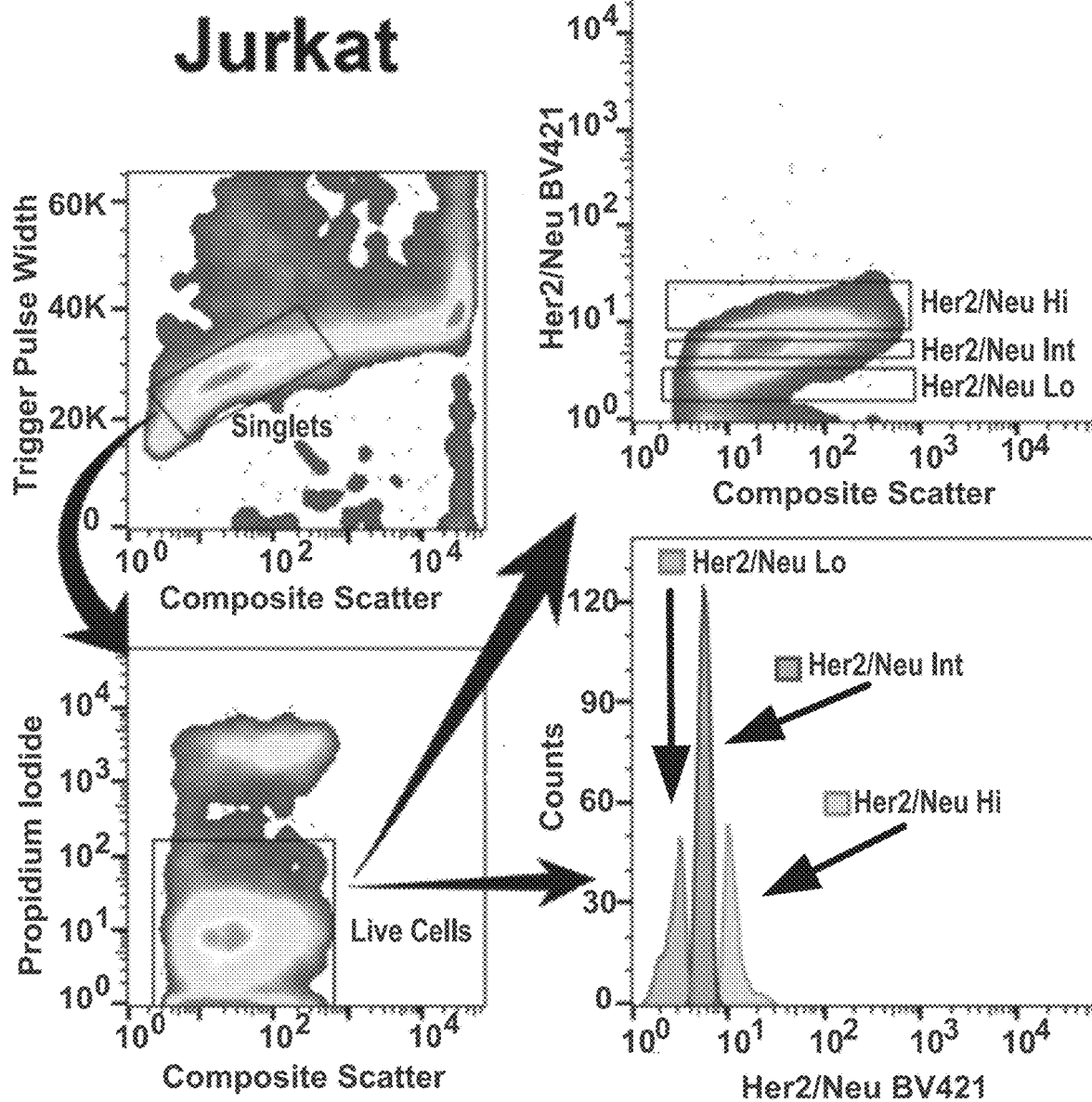
FIGS. 21A-D are plots showing three populations defined by Her2/Neu protein expressions in Jurkat, Hela, T47D, and SKBR3.
Figure 21B:
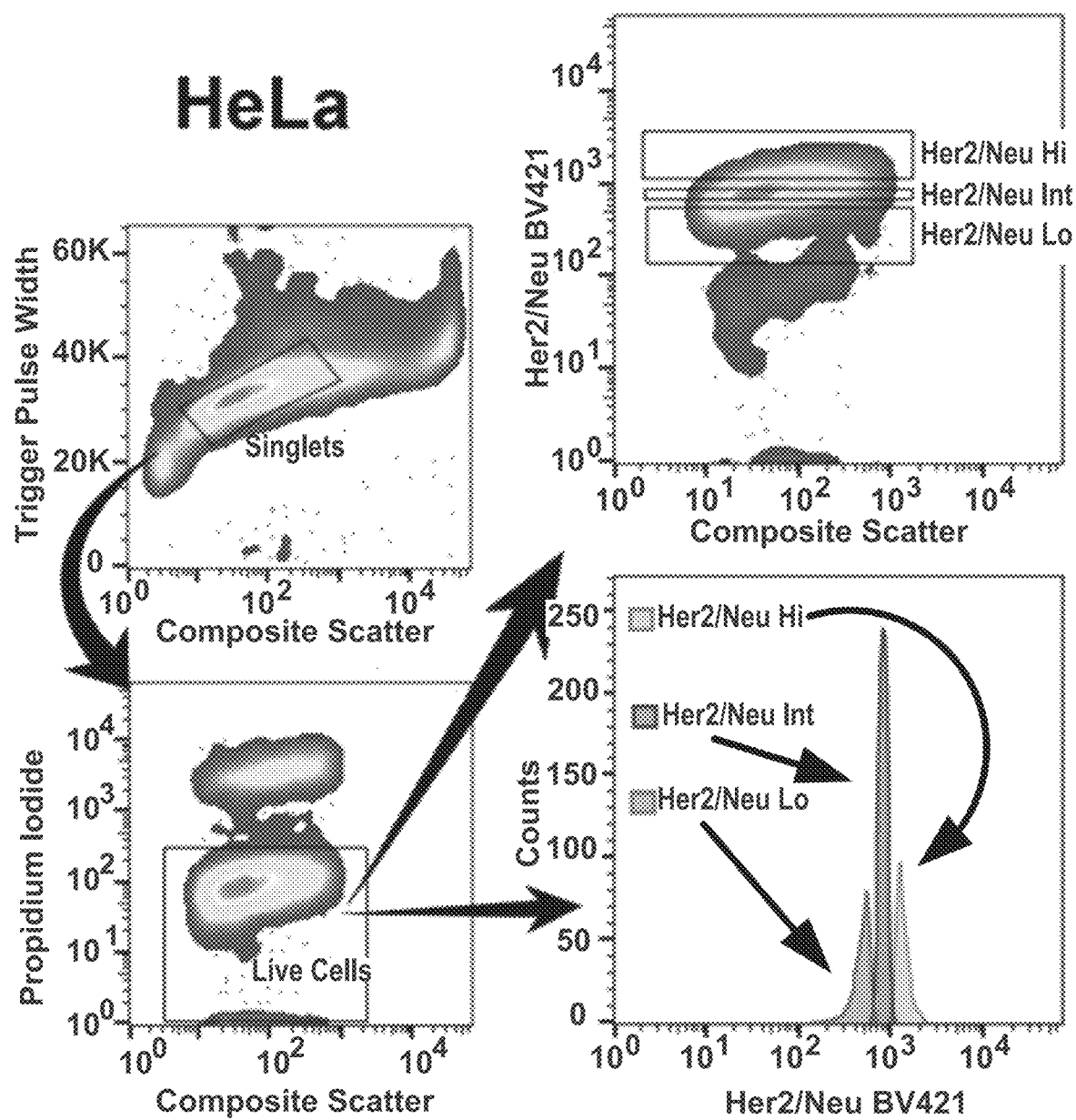
Figure 21C:
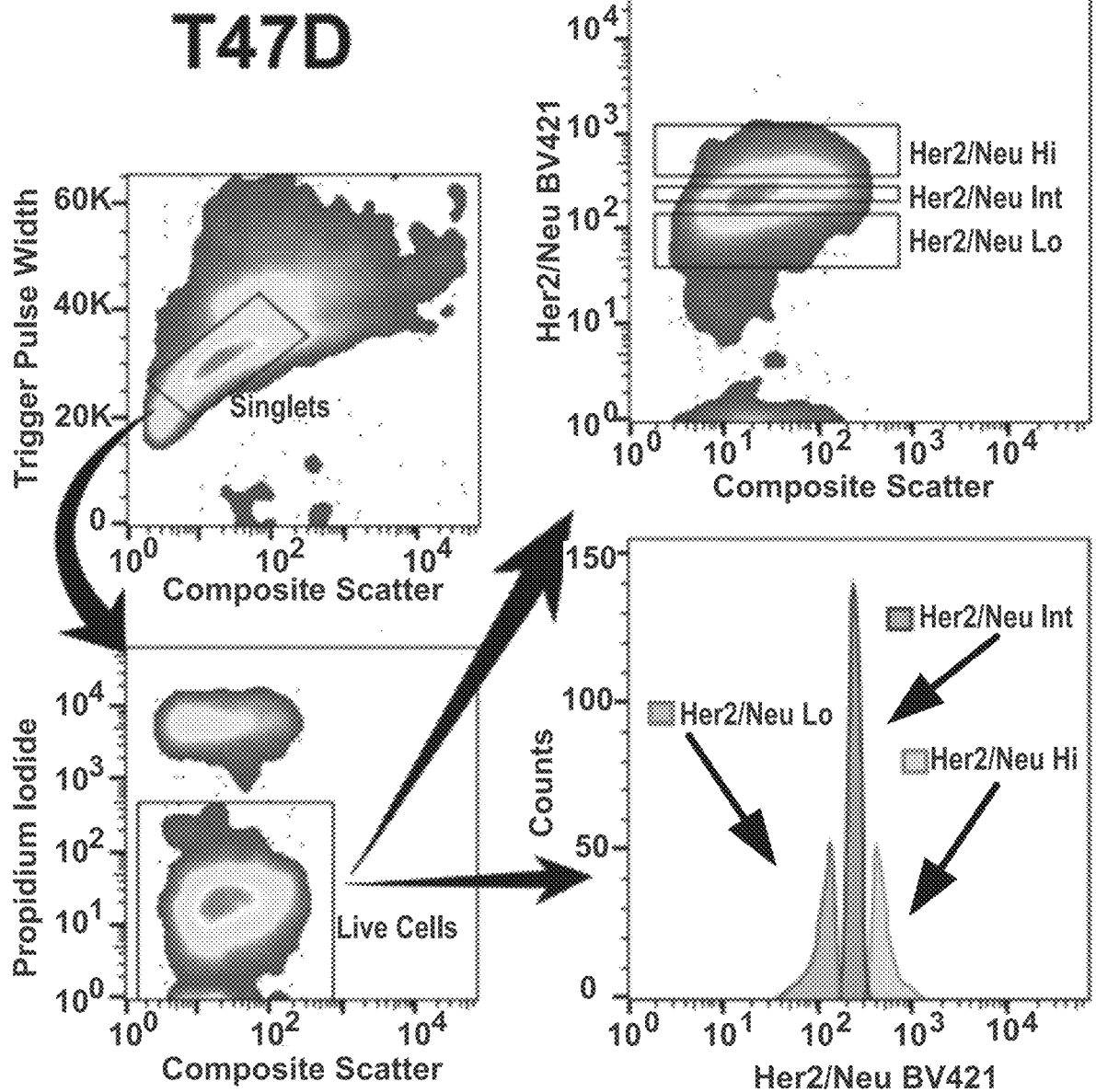
Figure 21D:
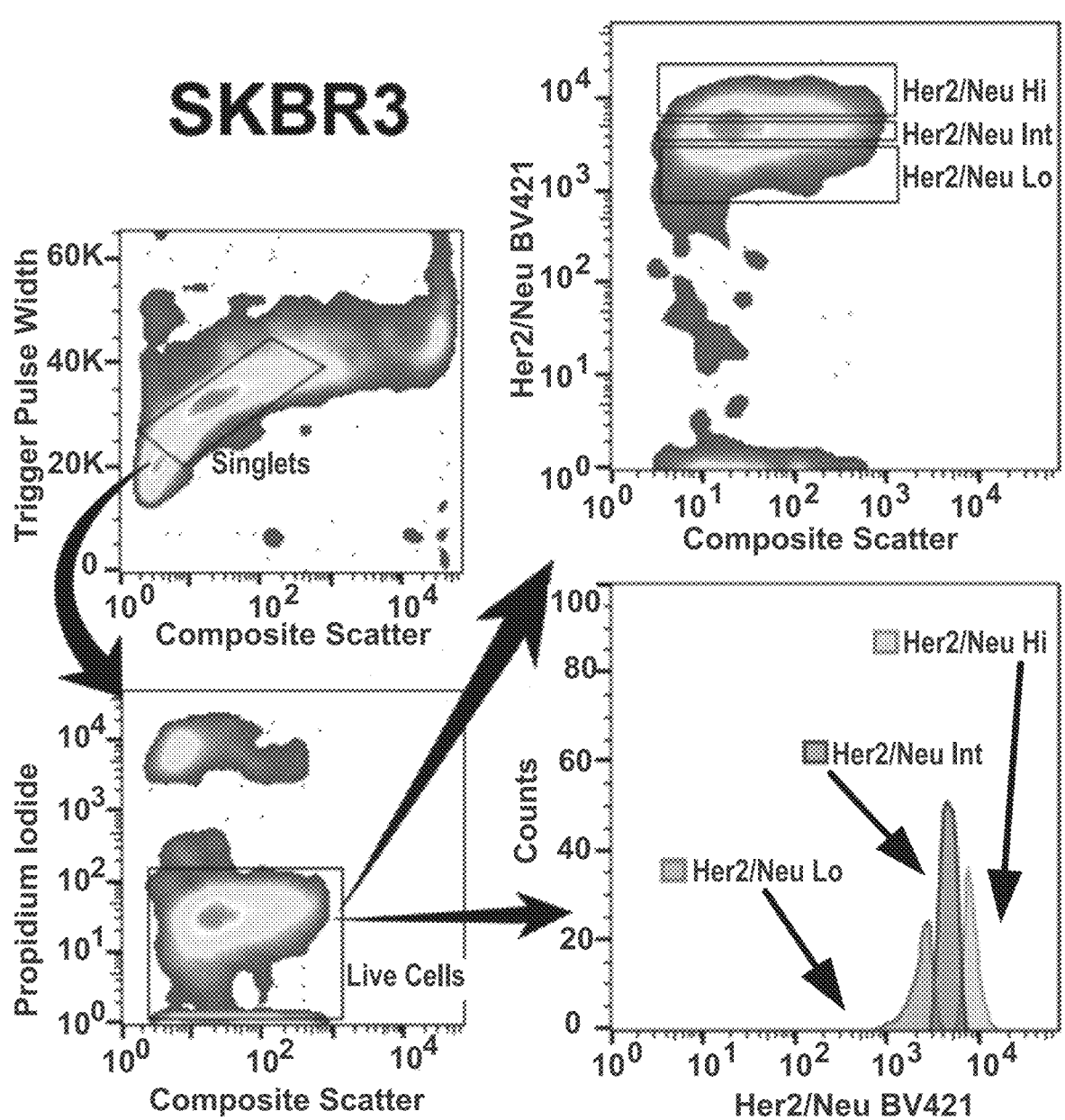

FIGS. 21A-D are plots showing that Jurkat cells in FIG. 21A, HeLa cells in FIG. 21B, T47D cells in FIG. 21C, and SKBR3 in FIG. 21D were sorted based on Her2/Neu expression. Three populations within each cell type were collected: Her2/Neu low, Her2/Neu intermediate, and Her2/Neu high. Single cells were sorted directly into each well of a BD Precise™ breast cancer 96-well assay plate. Each quadrant shows the gating strategy used to ensure that sorted cells were live single cells with the desired Her2/Neu expression profile.

FIG. 22 is a table showing the breast cancer genes analyzed with the Cellular Research Precise™ assay. Using the Cellular Research Precise™ gene library (99 genes) as a base plus 11 additional genes, this example interrogated 110 target genes. The genes that are shaded in light grey designate targets that were included in the final data analysis. The genes that are not shaded were not detected above threshold and thus excluded from the final data analysis. The products from four 96-well BD Precise assay plates (4×96 samples) were pooled, and one sequencing library was generated.

Figure 23:
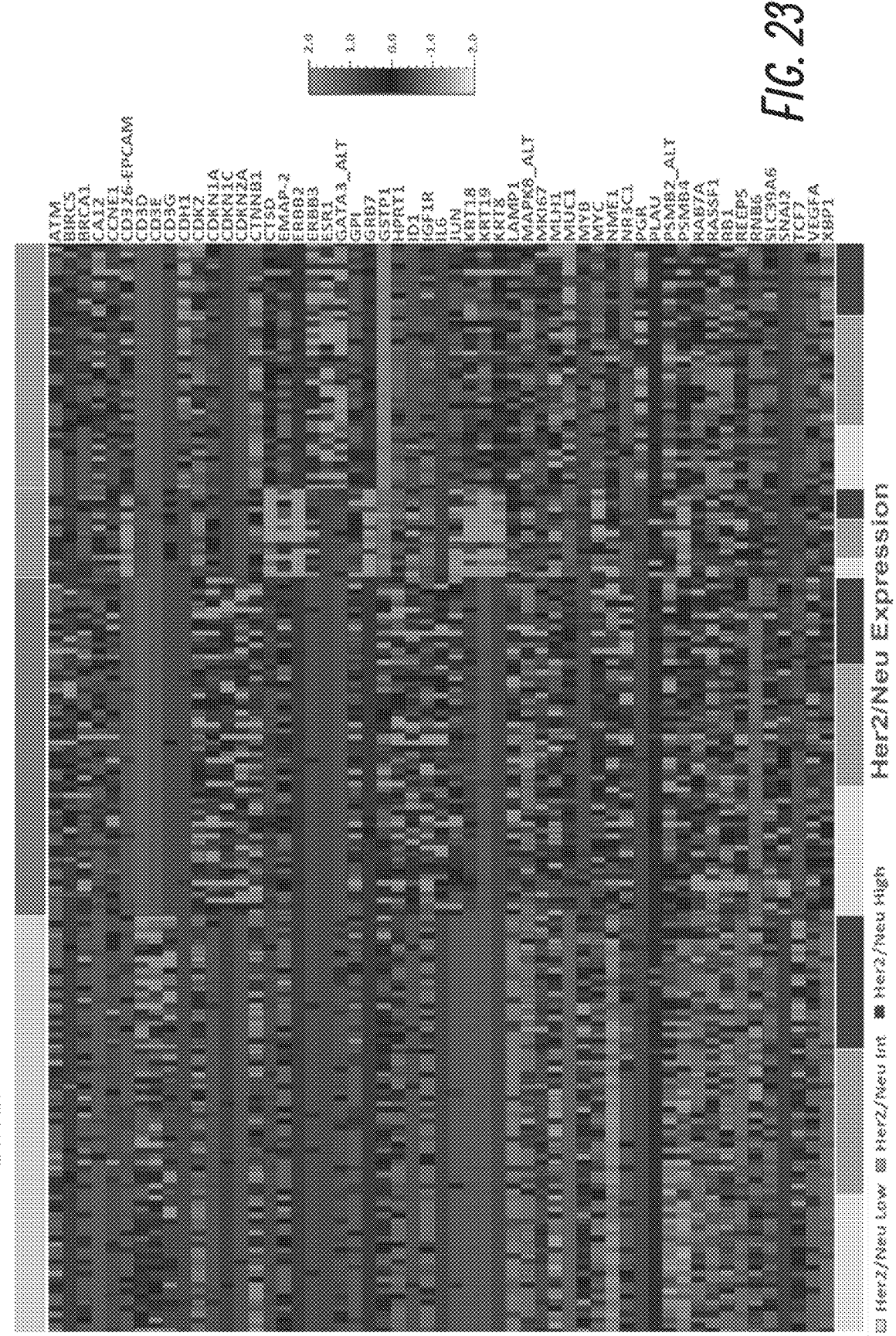
FIG. 23 is a heat map showing the analysis of the expressed target genes demonstrated a clear distinction between the four different cell types.

FIGS. 23, 24A-B, and 25A-G show automated data analysis was performed using the Seven Bridges Genomics Platform. Of 110 target genes, the expression levels of 57 were detectable. FIG. 23 is a heat map showing the analysis of the expressed target genes demonstrated a clear distinction between the four different cell types. Within each cell type, the subpopulations defined by Her2/Neu protein expression levels, did not exhibit significant differences in gene expression patterns.

Figure 24B:
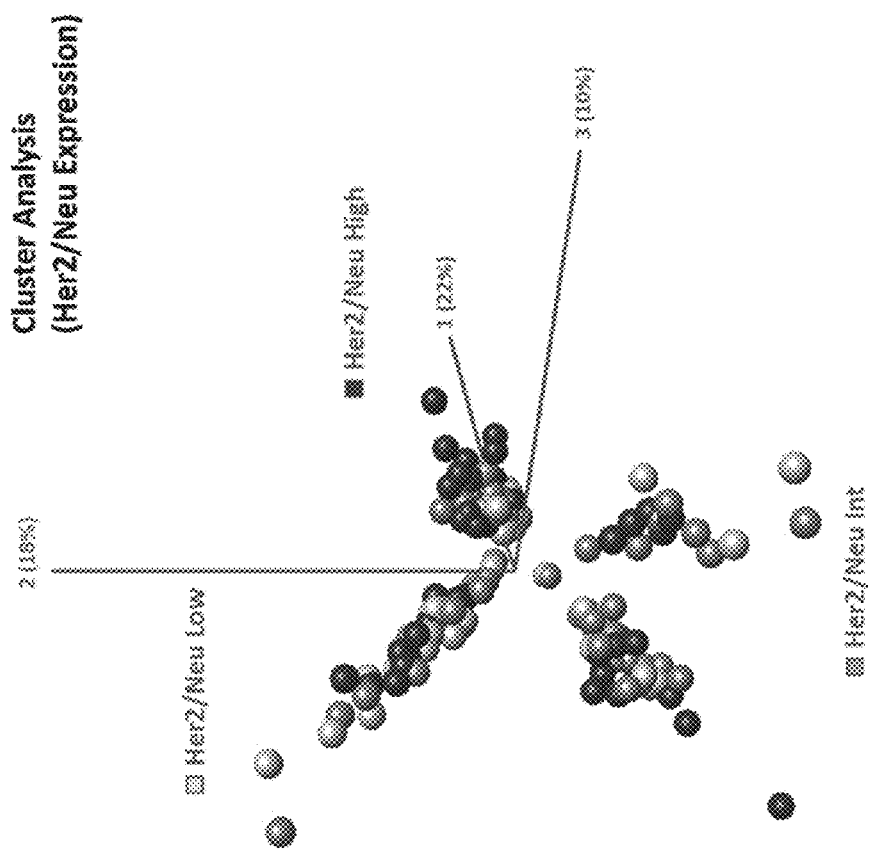
FIGS. 24A-B are PCA plots showing clustering by cell type with random Her2/Neu expressions supporting the heat map results.
Figure 24A:
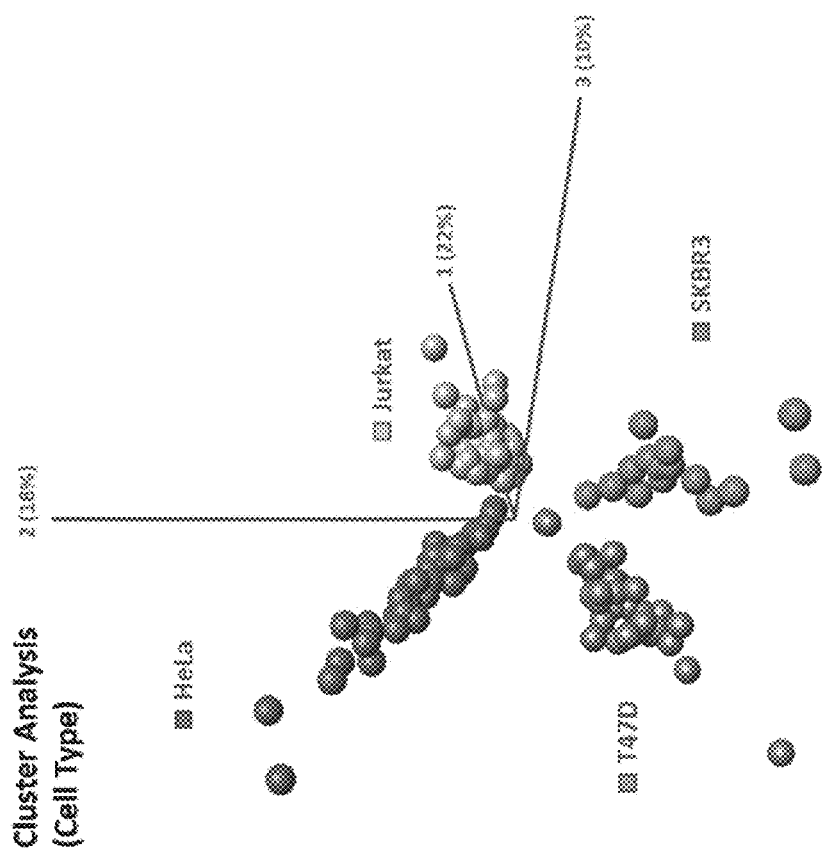

FIGS. 24A-B are PCA plots showing clustering by cell type with random Her2/Neu expressions supporting the heat map results. FIG. 24A is a PCA plot shows clustering analysis by cell type. The clustering analysis shows that the four cell types clearly segregated into four distinct clusters. FIG. 24B is a PCA plot showing that Her2/Neu expression had no discernable pattern within each cell type cluster.

Figure 25A:
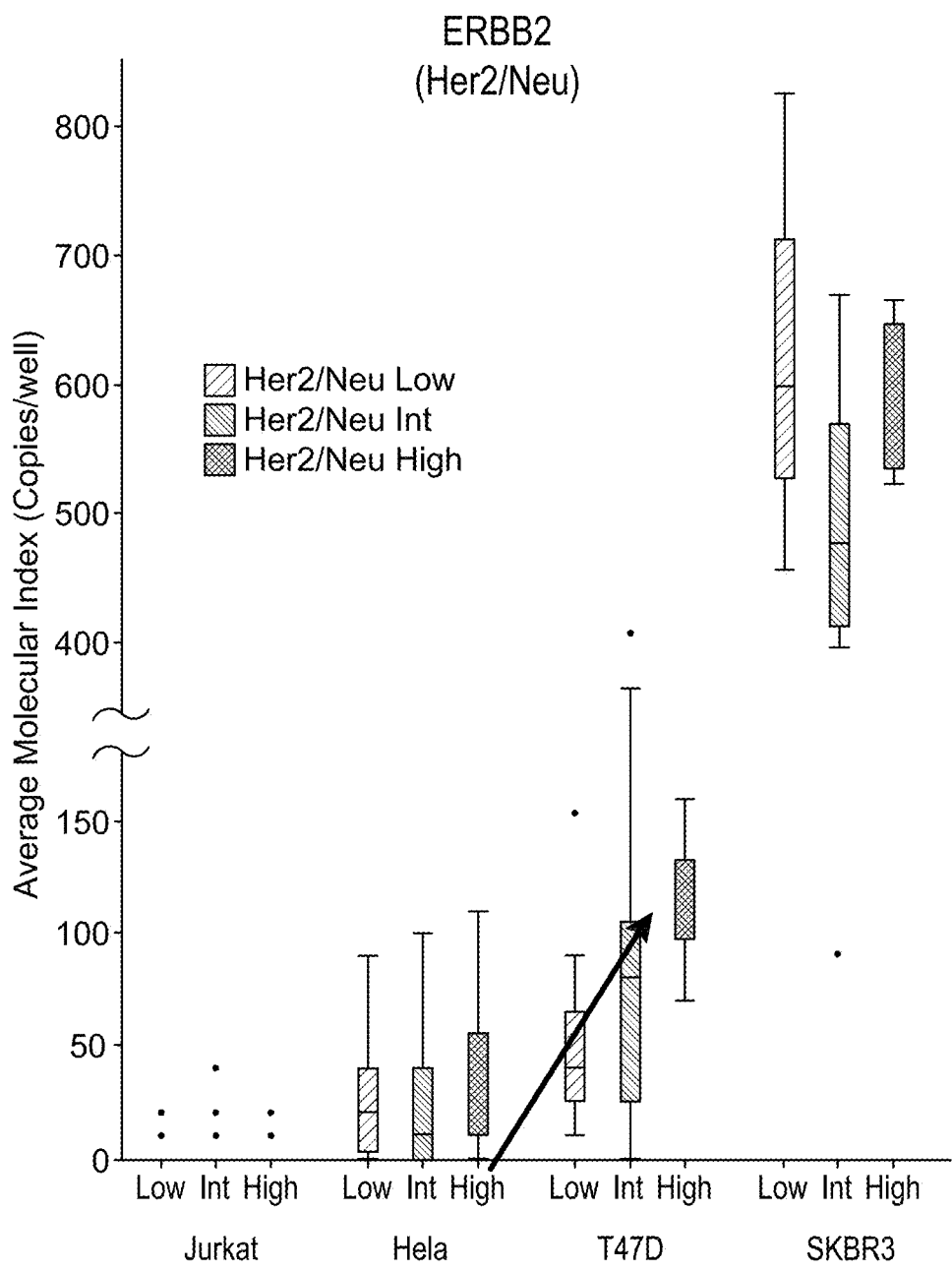
FIGS. 25A-G are expression plots showing that step-wise increases in ERBB2, BRCA1, CDK2, MUC1, CDH1, CTSD, and CTSD.
Figures 25B, 25C:
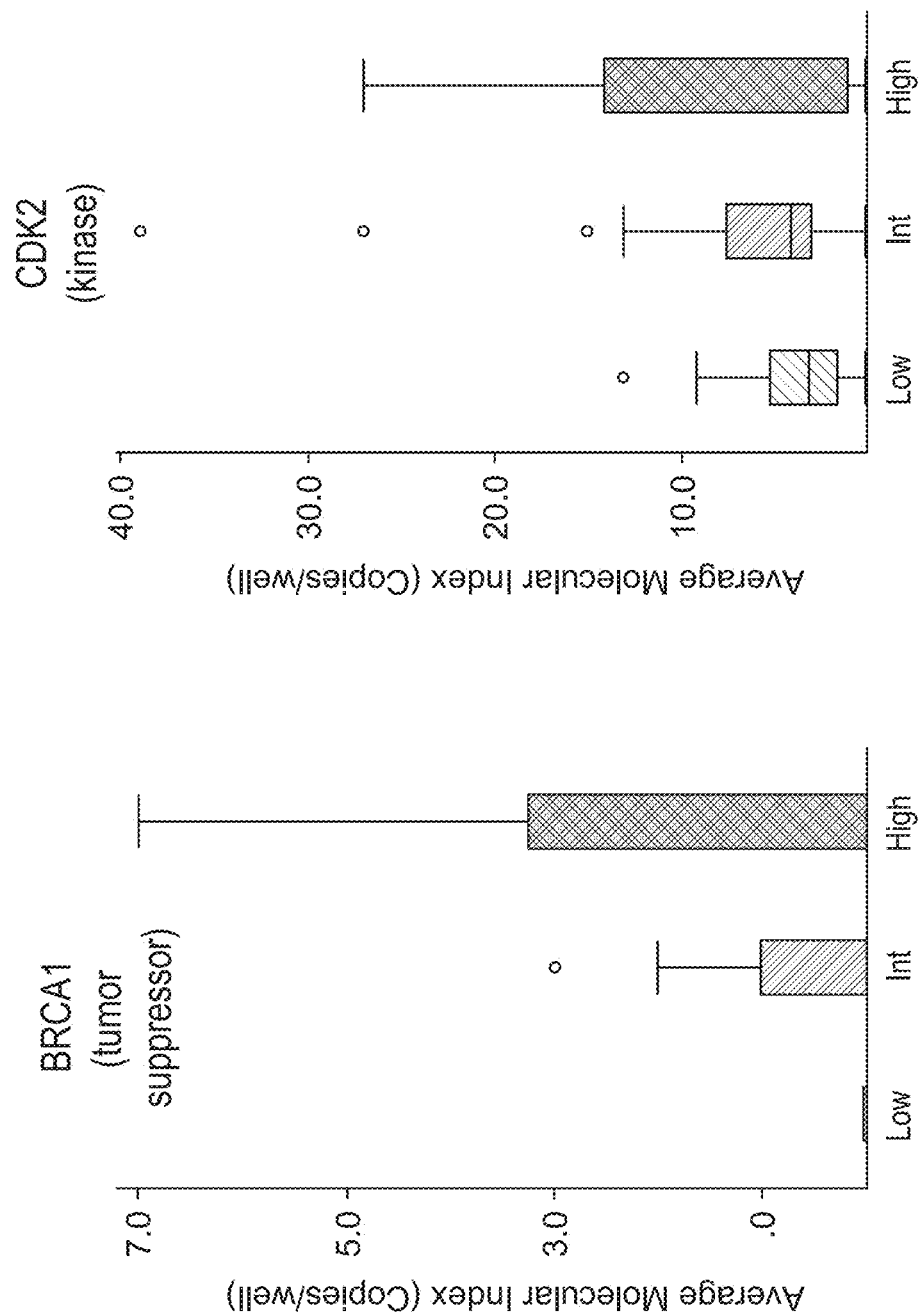
Figure 25E:
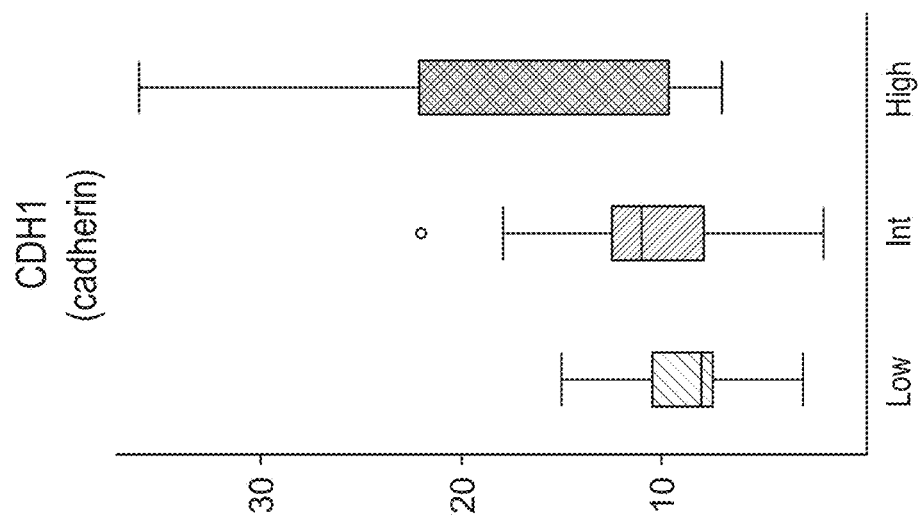
Figure 25D:
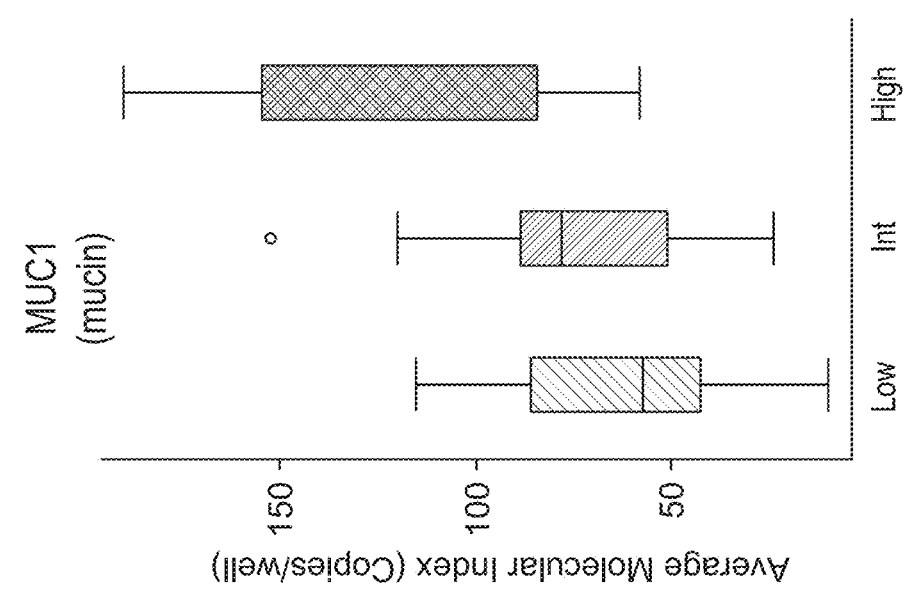
Figures 25F, 25G:
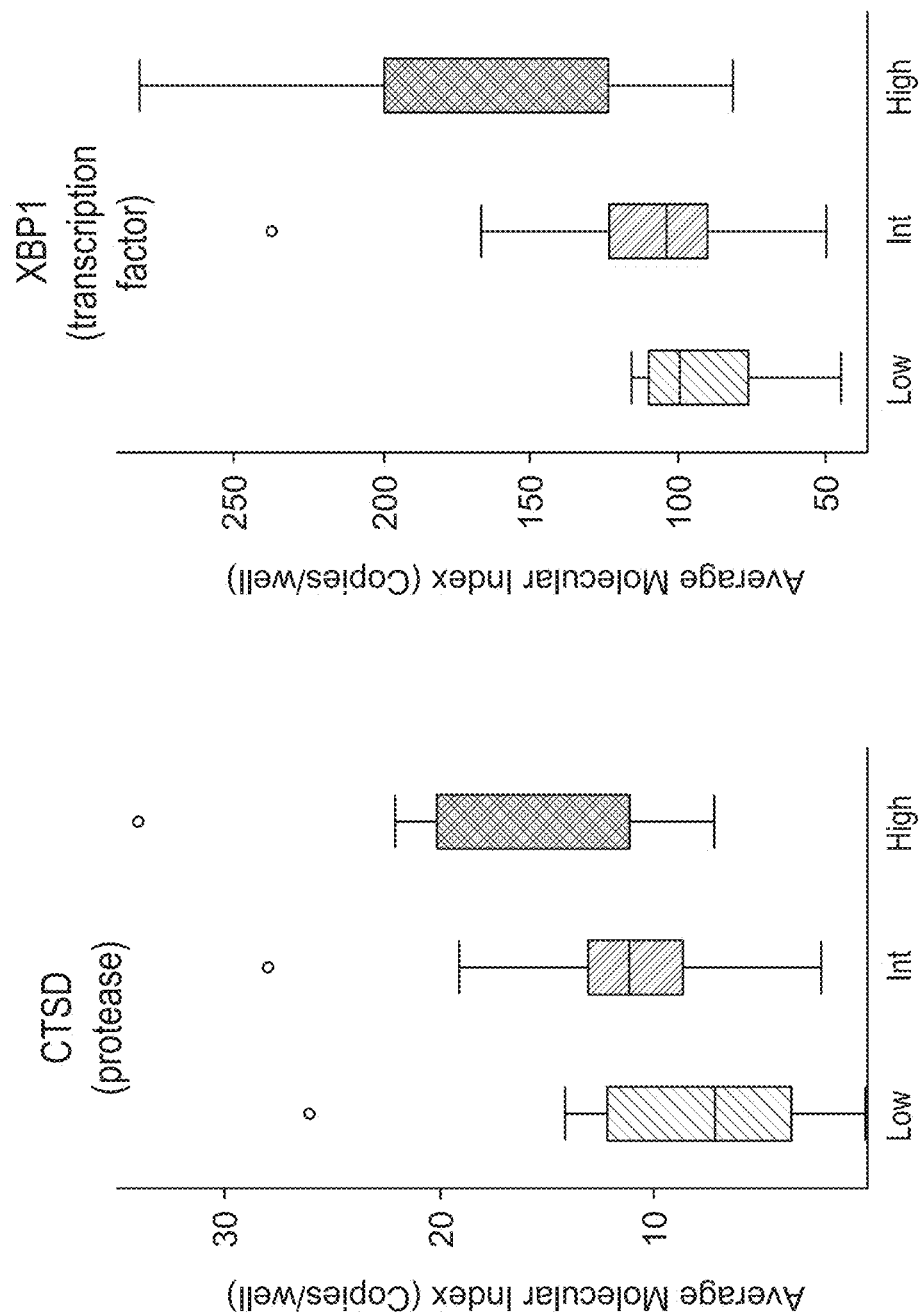

FIGS. 25A-G are expression plots showing that step-wise increases in ERBB2, BRCA1, CDK2, MUC1, CDH1, CTSD, and CTSD. FIG. 25A shows that ERBB2, the mRNA precursor to Her2/Neu, had extreme over-expression in SKBR3, relatively low expression in T47D, and little to no expression in HeLa and Jurkat cells. Closer examination of ERBB2 expression in T47D, shows a step-wise increase that correlates nicely to Her2/Neu protein expression by flow cytometry. Similar step-wise increases in other gene products that seemed to correlate with Her2/Neu expression were detected in BRCA1, a tumor suppressor, shown in FIG. 25B, CDK2, a kinase, shown in FIG. 25C, MUC1, a mucin, shown in FIG. 25D, CDH1, a cadherin, shown in FIG. 25E, CTSD, a protease shown in FIG. 25F, and XBP1, a transcription factor, shown in FIG. 25G.

These data show that differential expression of Her2/Neu among different cancer cell lines can be detected at both the protein level and the mRNA level. T47D cells exhibited an increase in mRNA levels of ERBB2 that demonstrated a modest correlation with the concurrent increase in protein levels of Her2/Neu between sorted populations of Her2/Neu low, Her2/Neu intermediate and Her2/Neu high expressing cells. Similar concurrent increases in mRNA levels of BRCA1, CDK2, MUC1, CDH1, CTSD, and XBP1 also showed a modest correlation to Her2/Neu protein expression levels. The BD FACSseq™ cell sorter coupled with the Cellular Research Precise™ Assay provides a robust and cost-effective workflow from single cell selection and isolation to downstream quantitative mRNA analysis. This workflow is a powerful tool that combines phenotypic and gene expression profiles for studying complex biological samples at the single cell level.

The identification of genes associated with Her2/neu overexpression on a single cell level shed light on the mechanisms at play in these aggressive cancers that are known to comprise up to 30% of all breast cancers. Altogether, these data, generated by combining single-cell sorting and molecular sorting, shed light on the mechanisms at play in these aggressive cancers that are known to comprise up to 30% of all breast cancers.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of single-cell polynucleotide sequencing, the method comprising:
    (a) depleting cells not of interest in a sample comprising a plurality of cells to obtain a plurality of cells of interest at a first concentration;
    (b) focusing the plurality of cells of interest obtained in (a) into a core stream in a channel to increase the concentration of the plurality of cells of interest in the channel from the first concentration to a higher second concentration;
    (c) flow cytometrically isolating the plurality of cells of interest at the higher second concentration obtained from step (b), wherein step (c) comprises tagging/staining of a cell surface marker and flow cytometrically sorting the plurality of cells of interest based on the cell surface marker;
    (d) generating a molecularly indexed polynucleotide library of one or more mRNAs encoding the cell surface marker of one or more of the plurality of cells of interest isolated in (c); and
    (e) obtaining sequence information of the molecularly indexed polynucleotide library generated in (d), thereby determining sequence information of the one or more mRNAs, to obtain an expression level for the cell surface marker.

2. The method of claim 1, wherein focusing the plurality of cells of interest obtained in (a) comprises focusing the plurality of cells of interest based on cell size.

3. The method of claim 1, wherein focusing the plurality of cells of interest obtained in (a) comprises acoustically focusing the plurality of cells of interest.

4. The method of claim 3, wherein acoustically focusing the plurality of cells of interest comprises:
    suspending the plurality of cells in the channel; and
    exposing said channel to an axial acoustic standing wave field parallel to the direction of flow, wherein said axial acoustic standing wave field drives the plurality of cells of interest to positions of potential force minimum along the center axis of said channel to result in uniformly spaced cells.

5. The method of claim 1, wherein the one or more polynucleotides comprise ribonucleic acids (RNAs).

6. The method of claim 5, wherein the RNAs are messenger RNAs (mRNAs).

7. The method of claim 6, wherein the sequence information of the one or more polynucleotides comprises transcript counts of at least 10 genes.

8. The method of claim 7, wherein the transcript counts of the at least 10 genes indicate genotype, phenotype, or one or more genetic mutation of the patient.

9. The method of claim 1, wherein no more than 500 cells of interest of the plurality of cells of interest are flow cytometrically isolated in (c).

10. The method of claim 1, wherein obtaining sequence information comprises sequencing the molecularly indexed polynucleotide library generated in (d).

11. The method of claim 10, wherein obtaining sequence information comprises deconvoluting sequencing result from sequencing the molecularly indexed polynucleotide library generated in (d).

12. The method of claim 1, wherein the sample comprises a biological sample, a clinical sample, an environmental sample, or a biological fluid, tissue or cell from a patient.

13. The method of claim 1, wherein the cells of interest in the sample comprise stem cells, cancer cells, blood cells, peripheral blood mononuclear cells, circulating tumor cells, breast cancer cells, cells at a cell cycle phase of desire, or a combination thereof.

14. The method of claim 1, wherein less than 10% of the plurality of cells comprises the plurality of cells of interest.

15. The method of claim 1, wherein flow cytometrically isolating the plurality of cells of interest at the higher second concentration in (c) comprises flow cytometrically isolating individual cells of the plurality of cells of interest into a plurality of partitions respectively.

16. The method of claim 15, wherein the plurality of partitions comprises a plurality of microwells, a plurality of droplets, or any combination thereof.

17. The method of claim 1, wherein the channel comprises an elongated fluid-filled channel.

18. The method of claim 1, wherein depleting the cells not of interest comprises depleting at least 80% of the cells not of interest in the sample.

19. The method of claim 1, wherein depleting the cells not of interest comprises magnetically depleting the cells not of interest in the sample.

20. The method of claim 1, wherein said generating in (d) comprises generating the molecularly indexed polynucleotide library of the one or more of the plurality of cells of interest isolated in (c) using a plurality of stochastic barcodes, wherein each stochastic barcode comprises an identical first label sequence, a molecular label sequence, and a target specific region, wherein the first label sequence comprises at least 6 nucleotides, wherein the molecular label sequence comprises at least 6 nucleotides, and wherein at least 100 of the plurality of stochastic barcodes comprises different molecular label sequences.

21. The method of claim 20, wherein at least 10000 of the plurality of stochastic barcodes comprises different molecular label sequences.

22. The method of claim 20, wherein said generating in (d) comprises performing a nucleic acid extension reaction on one or more stochastic barcodes hybridized to the one or more polynucleotides of the one or more of the plurality of cells of interest isolated in (c).

23. The method of claim 22, wherein the nucleic acid extension reaction comprises a reverse transcription reaction.

24. The method of claim 20, wherein the target specific region comprises a poly(dT) sequence.

25. The method of claim 20, wherein said generating in (d) comprises generating a molecularly indexed polynucleotide library of one or more polynucleotides of 10 or more cells of interest and 10 or more cells not of interest.

26. The method of claim 25, wherein said generating in (d) comprises generating a molecularly indexed polynucleotide library of one or more polynucleotides of 10 or more cells of interest and 100 or more cells not of interest.

27. The method of claim 1, wherein the plurality of cells of interest at the higher second concentration is at least $10^8$-folds higher than the plurality of cells of interest in the sample.

28. The method of claim 1, wherein flow cytometrically isolating the plurality of cells of interest at the higher second concentration in (c) is 100-fold faster than flow cytometrically isolating the plurality of cells of interest in the sample.

29. The method of claim 1, wherein flow cytometrically isolating the plurality of cells of interest at the higher second concentration in (c) is 100-fold faster than flow cytometrically isolating the plurality of cells of interest at the first concentration obtained in (a).

30. The method of claim 1, wherein flow cytometrically isolating the plurality of cells of interest at the higher second concentration in (c) comprises flow cytometrically isolating the plurality of cells of interest at the higher second concentration using fluorescence-activated cell sorting (FACS).

31. The method according to claim 1, wherein the cell surface marker is selected from the group consisting of: ALCAM; CD166; ASGR1; BCAM; BSG; CD147; CD14; CD19; CD2; CD200; CD127; CD25; CD161; CD45RA; CD15S; CD4; CD3; EpCAM; CD44; and Her2/Neu; and combinations thereof.

* * * * *